US012221655B2

(12) United States Patent
Baillie et al.

(10) Patent No.: US 12,221,655 B2
(45) Date of Patent: Feb. 11, 2025

(54) PRE-SURGICAL RISK STRATIFICATION BASED ON PDE4D7 AND DHX9 EXPRESSION

(71) Applicants: KONINKLIJKE PHILIPS N.V., Eindhoven (NL); THE UNIVERSITY COURT OF THE UNIVERSITY OF GLASGOW, Glasgow (GB)

(72) Inventors: George Baillie, Glasgow (GB); Ralf Dieter Hoffmann, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 863 days.

(21) Appl. No.: 17/273,568

(22) PCT Filed: Oct. 11, 2019

(86) PCT No.: PCT/EP2019/077549
§ 371 (c)(1),
(2) Date: Mar. 4, 2021

(87) PCT Pub. No.: WO2020/074679
PCT Pub. Date: Apr. 16, 2020

(65) Prior Publication Data

US 2021/0355543 A1 Nov. 18, 2021

(30) Foreign Application Priority Data

Oct. 11, 2018 (EP) .................................... 18199784

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

2011/0136683 A1 6/2011 Davicioni

FOREIGN PATENT DOCUMENTS

| | | | |
|---|---|---|---|
| WO | 2010131194 | A1 | 11/2010 |
| WO | 2014028884 | A2 | 2/2014 |
| WO | 2018099884 | A1 | 6/2018 |

OTHER PUBLICATIONS

NCBI GEO GPL29829. Mar. 9, 2021, NCBI Gene Expression Omnibus, National Library of Medicine, NIH, Bethesda, MD, available via URL < ncbi.nlm.nih.gov/geo/query/acc.cgi?acc= GPL29829> (Year: 2021).*

Affymetrix, Package Insert for GeneChip® Human Genome U133 Plus 2.0 array, 2009 (Year: 2009).*

Rijntjes et al J Clinical Oncology. May 30, 2017. 35(15), abstract 5069 (Year: 2017).*

Bettin et al Int J Biol Markers. 2016. 31(2): e153-e162 (Year: 2016).*

Rizzi et al PLoS One. 2008. 3(10): e3617 (Year: 2008).*

Arya et al. Exp Rev Mol Diagn. 2005. 5(2): 209-219 (Year: 2005).*

Quon H. et al., "Dramatic increase in prostate cancer cases by 2021", BJU Intrnational, Abstract, 2011.

Ferlay, J. et al., GLOBOCAN 2012 v 1.0, Cancer Incidence and Mortality Worldwide: IARC CancerBase No. 11 {Internet}, Lyon, France, International Agency for Research on Cancer, 2013.

Bangma C.H. et al., "Overdiagnosis and overtreatment of early detected prostate cancer", World Journal of Urology, vol. 25, No. 1, pp. 3-9, 2007.

Schroeder, F.H. et al., "Screening and Prostate-Cancer Mortality in a Randomized European Study", The New England Journal of Medicine, vol. 360, No. 13, pp. 1320-1328, 2009.

Nam, R.K. et al., "Increasing hospital admission rates for urological complications after transrectal ultrasound guided biopsy", Journal of Urology, vol. 183, No. 3, pp. 963-968, 2010.

Snyder, C.F. et al., "How does initial treatment choice affect short-term and long term costs for clinically localized prostate cancer?", Cancer, vol. 116, No. 23, pp. 5391-5399, 2010.

Cooperberg, M.R. et al., "Contemporary trends in low risk prostate cancer: risk assessment and treatment", Journal of Urology, vol. 173, No. 3, Pt. 2, pp. 14-19, 2007.

Bagma, C.H. et al., "Defining and predicting indolent and low prostate cancer", Critical Reviews in Oncology/Hematology, Abstract, 2012.

Heidenreich, A. et al., "Guidelines on Prostate Cancer", European Association of Urology, 2014.

Heidenreich, A. et al., "Extended pelvic lymphadenectomy in patients undergoing radical prostatectomy: high incidence of lymph node metastasis", Journal of Urology, vol. 167, No. 4, p. 1681-1686, 2002.

Bader, P. et al., "Is a limited lymph node dissection and adequate staging procedure for prostate cancer?", Journal of Urology, vol. 168, No. 2, pp. 514-518, 2002.

Conti, M. et al., "Biochemistry and physiology of cyclic nucleotide phosphodiesterases: essential components in cyclic nucleotide signaling", Annual Review of Biochemistry, Abstract, 2007.

(Continued)

*Primary Examiner* — Carla J Myers

(57) ABSTRACT

The invention relates to a method of pre-surgical risk stratification of a prostate cancer subject, comprising determining a gene expression profile for phosphodiesterase 4D variant 7 (PDE4D7) in a biological sample obtained from the subject, determining a gene expression profile for DExH-box helicase 9 (DHX9) in the same or another biological sample obtained from the subject, and determining a pre-surgical prognostic risk score for the subject based on the gene expression profile for PDE4D7 and the gene expression profile for DHX9. This may allow for an improved stratification of the subject in a pre-surgical setting that may result in better primary treatment decisions. For instance, the pre-surgical prognostic risk score may allow to make better recommendations on whether to select active surveillance vs. active intervention, e.g., radical prostatectomy, for certain sub-populations of prostate cancer patients.

8 Claims, 6 Drawing Sheets

Specification includes a Sequence Listing.

(56) References Cited

OTHER PUBLICATIONS

Boettcher, R. et al., "Human phosphodiesterase 4DF7 (PDE4D7) expression is increased in TMPRSS2-ERG positive primary prostate cancer and independently adds to a reduced risk of post surgical disease progression", British Journal of Cancer, vol. 113, No. 10, pp. 1502-1511, 2015.
Taylor, B.S. et al., "Integrative genomic profiling of human prostate cancer", Cancer Cell, vol. 18, No. 1, pp. 11-22, 2010.
Van Strijp, D. et al., "The Prognostic PDE4D7 Score in a Diagnostic Biopsy Prostate Cancer Patient Cohort with Longitudinal Biological Outcomes", Prostate Cancer, vol. 2018, pp. 1-11, 2018.
Lee, T. et al., "The biology of DHX9 and its potential as a therapeutic target Introduction to DHX9 and DEXD/H-Box Helicases", Oncotarget 42716 Oncotarget, (Mar. 28, 2016), p. 27.
Erho, N. et al. "Discovery and Validation of a Prostate Cancer Genomic Classifier that Predicts Early Metastasis Following Radical Prostatectomy", PLoS One, vol. 8, No. 6, (2013), p. e66855.
International Search Report for PCT/EP2019/077549 filed Oct. 11, 2019.
Mosquera, J.M. et al. "Prevalence of TMPRSS2-ERG fusion prostate cancer among men undergoing prostate biopsy in the United States." Clin Cancer Res 15, 4706-4711 (2009).
Nichol, M.B. et al. Cost-effectiveness of Prostate Health Index for prostate cancer detection. BJU Int. Abstract. (2011).
James, M.L. "Prostate cancer (early), search date Feb. 2006." Online version of BMJ Clinical Evidence. 2006; 10:1805.
Medtech Insight U.S. markets for diagnostic and therapeutic prostate disease/disorder management products (2007).

* cited by examiner

SEQUENCE LISTING

```
<160> NUMBER OF SEQ ID NOS: 75

<210> SEQ ID NO 1
<211> LENGTH: 7801
<212> TYPE: DNA
<213> ORGANISM: Homo sapiens

<400> SEQUENCE: 1

gtggtggccg cgcacccggc cgcggctgat tcattcactt caagtgccgt gcagaaggct     60

cggcaggcgg ggcgggcgtg gggccgcggc tccgggttgg ggaccgagga gatccggctg    120

tggaccagac gctcctctgc ggggcgggca cccaagcgcg ctcgccaccc cctcgccatc    180

cgctagagcc gggctcctgg actgggactc gggcccgccg cacagttgaa aagtcgcata    240

gtggtttttc cgctcgcgtc gctgtgtgaa agttggctcg ccgctctttg cacgccctcc    300

ctggaggccg acccgagacg ccaagctgga gagaccgtgc ctccccgagg ccggccgccc    360

cgcgagcaca gcctccgccc ccgttgcact gccgggctgg gcaatatgaa ggagcagccc    420

tcatgtgccg gcaccgggca tccgagcatg gcggggtatg gcaggatggc cccctttgaa    480

ctcgctagcg gacccgtgaa gcgcttgaga actgagtccc cctttccctg tctcttcgca    540

gaggaggcct accagaaact ggccagcgag accctggagg agctggactg gtgtctggac    600

cagctagaga ccctacagac caggcactcc gtcagtgaga tggcctccaa caagtttaaa    660

aggatgctta atcgggagct cacccatctc tctgaaatga gtcggtctgg aaatcaagtg    720
```

-continued

```
tcagagttta tatcaaacac attcttagat aagcaacatg aagtggaaat tccttctcca    780
actcagaagg aaaaggagaa aaagaaaaga ccaatgtctc agatcagtgg agtcaagaaa    840
ttgatgcaca gctctagtct gactaattca agtatcccaa ggtttggagt taaaactgaa    900
caagaagatg tccttgccaa ggaactagaa gatgtgaaca aatggggtct tcatgttttc    960
agaatagcag agttgtctgg taaccggccc ttgactgtta tcatgcacac catttttcag   1020
gaacgggatt tattaaaaac atttaaaatt ccagtagata ctttaattac atatcttatg   1080
actctcgaag accattacca tgctgatgtg gcctatcaca acaatatcca tgctgcagat   1140
gttgtccagt ctactcatgt gctattatct acacctgctt tggaggctgt gtttacagat   1200
ttggagattc ttgcagcaat tttgccagt gcaatacatg atgtagatca tcctggtgtg   1260
tccaatcaat ttctgatcaa tacaaactct gaacttgcct tgatgtacaa tgattcctca   1320
gtcttagaga accatcattt ggctgtgggc tttaaattgc ttcaggaaga aaactgtgac   1380
attttccaga atttgaccaa aaaacaaaga caatctttaa ggaaaatggt cattgacatc   1440
gtacttgcaa cagatatgtc aaaacacatg aatctactgg ctgatttgaa gactatggtt   1500
gaaactaaga aagtgacaag ctctggagtt cttcttcttg ataattattc cgataggatt   1560
caggttcttc agaatatggt gcactgtgca gatctgagca acccaacaaa gcctctccag   1620
ctgtaccgcc agtggacgga ccggataatg gaggagttct tccgccaagg agaccgagag   1680
agggaacgtg gcatggagat aagccccatg tgtgacaagc acaatgcttc cgtggaaaaa   1740
tcacaggtgg gcttcataga ctatattgtt catcccctct gggagacatg ggcagacctc   1800
gtccaccctg acgcccagga tattttggac actttggagg acaatcgtga atggtaccag   1860
agcacaatcc ctcagagccc ctctcctgca cctgatgacc cagaggaggg ccggcagggt   1920
caaactgaga aattccagtt tgaactaact ttagaggaag atggtgagtc agacacggaa   1980
aaggacagtg gcagtcaagt ggaagaagac actagctgca gtgactccaa gactctttgt   2040
actcaagact cagagtctac tgaaattccc cttgatgaac aggttgaaga ggaggcagta   2100
ggggaagaag aggaaagcca gcctgaagcc tgtgtcatag atgatcgttc tcctgacacg   2160
taacagtgca aaaactttca tgcctttttt tttttaagt agaaaaattg tttccaaagt   2220
gcatgtcaca tgccacaacc acggtcacac ctcactgtca tctgccagga cgtttgttga   2280
acaaaactga ccttgactac tcagtccagc gctcaggaat atcgtaacca gtttttcac    2340
ctccatgtca tccgagcaag gtggacatct tcacgaacag cgtttttaac aagatttcag   2400
cttggtagag ctgacaaagc agataaaatc tactccaaat tattttcaag agagtgtgac   2460
tcatcaggca gcccaaaagt ttattggact tggggtttct attcctttt atttgtttgc    2520
aatattttca gaagaaaggc attgcacaga gtgaacttaa tggacgaagc aacaaatatg   2580
tcaagaacag gacatagcac gaatctgtta ccagtaggag gaggatgagc cacagaaatt   2640
gcataatttt ctaatttcaa gtcttcctga tacatgactg aatagtgtgg ttcagtgagc   2700
tgcactgacc tctacatttt gtatgatatg taaaacagat tttttgtaga gcttactttt   2760
attattaaat gtattgaggt attatattta aaaaaaacta tgttcagaac ttcatctgcc   2820
actggttatt tttttctaag gagtaacttg caagttttca gtacaaatct gtgctacact   2880
ggataaaaat ctaatttatg aattttactt gcaccttata gttcatagca attaactgat   2940
ttgtagtgat tcattgtttg ttttatatac caatgacttc catattttaa aagagaaaaa   3000
caactttatg ttgcaggaaa cccttttgt aagtctttat tatttacttt gcattttgtt    3060
```

-continued

```
tcactctttc cagataagca gagttgctct tcaccagtgt ttttcttcat gtgcaaagtg   3120
actatttgtt ctataatact tttatgtgtg ttatatcaaa tgtgtcttaa gcttcatgca   3180
aactcagtca tcagttcgtg ttgtctgaag caagtgggag atatataaat acccagtagc   3240
taaaatggtc agtctttttt agatgttttc ctacttagta tctcctaata acgttttgct   3300
gtgtcactag atgttcattt cacaagtgca tgtctttcta ataatccaca catttcatgc   3360
tctaataatc cacacatttc atgctcattt ttattgtttt tacagccagt tatagtaaga   3420
aaaaggtttt tccccttgtg ctgctttata atttagcgtg tgtctgaacc ttatccatgt   3480
ttgctagatg aggtcttgtc aaatatatca ctaccattgt caccggtgaa aagaaacagg   3540
tagttaagtt agggttaaca ttcatttcaa ccacgaggtt gtatatcatg actagctttt   3600
actcttggtt tacagagaaa agttaaacag ccaactaggc agtttttaag aatattaaca   3660
atatattaac aaacaccaat acaactaatc ctatttggtt ttaatgattt caccatggga   3720
ttaagaacta tatcaggaac atccctgaga aacggtttta agtgtagcaa ctactcttcc   3780
ttaatggaca gccacataac gtgtaggaag tcctttatca cttatcctcg atccataagc   3840
atatcttgca gaggggaact acttctttaa acacatggag ggaaagaaga tgatgccact   3900
ggcaccagag ggttagtact gtgatgcatc ctaaaatatt tattatattg gtaaaaattc   3960
tggttaaata aaaaattaga gatcactctt ggctgatttc agcaccagga actgtattac   4020
agttttagag attaattcct agtgtttacc tgattatagc agttggcatc atggggcatt   4080
taattctgac tttatcccca cgtcagcctt aataaagtct tctttacctt ctctatgaag   4140
actttaaagc ccaaataatc atttttcaca ttgatattca agaattgaga tagatagaag   4200
ccaaagtggg tatctgacaa gtggaaaatc aaacgtttaa gaagaattac aactctgaaa   4260
agcatttata tgtggaactt ctcaaggagc ctcctgggga ctggaaagta agtcatcagc   4320
caggcaaatg actcatgctg aagagagtcc ccatttcagt cccctgagat ctagctgatg   4380
cttagatcct ttgaaataaa aattatgtct ttataactct gatcttttac ataaagcaga   4440
agaggaatca actagttaat tgcaaggttt ctactctgtt tcctctgtaa agatcagatg   4500
gtaatctttc aaataagaaa aaaataaaga cgtatgtttg accaagtagt ttcacaagaa   4560
tatttgggaa cttgtttctt ttaattttat ttgtccctga gtgaagtcta gaaagaaagg   4620
taaagagtct agagtttatt cctctttcca aaacattctc attcctctcc tccctacact   4680
tagtatttcc cccacagagt gcctagaatc ttaataatga ataaaataaa aagcagcaat   4740
atgtcattaa caaatccaga cctgaaaggg taaagggttt ataactgcac taataaagag   4800
aggctctttt tttttcttcc agtttgttgg tttttaatgg taccgtgttg taaagatacc   4860
cactaatgga caatcaaatt gcagaaaagg ctcaatatcc aagagacagg gactaatgca   4920
ctgtacaatc tgcttatcct tgcccttctc tcttgccaaa gtgtgcttca gaaatatata   4980
ctgctttaaa aaagaataaa agaatatcct tttacaagtg gctttacatt tcctaaaatg   5040
ccataagaaa atgcaatatc tgggtactgt atggggaaaa aaatgtccaa gtttgtgtaa   5100
aaccagtgca tttcagcttg caagttactg aacacaataa tgctgtttta attttgtttt   5160
atatcagtta aaattcacaa taatgtagat agaacaaatt acagacaagg aaagaaaaaa   5220
cttgaatgaa atggatttta cagaaagctt tatgataatt tttgaatgca ttatttattt   5280
tttgtgccat gcattttttt tctcaccaaa tgaccttacc tgtaatacag tcttgtttgt   5340
ctgtttacaa ccatgtattt attgcaatgt acatactgta atgttaattg taaattatct   5400
gttcttatta aaacatcatc ccatgatggg atggtgttga tatatttgga aactcttggt   5460
```

-continued gagagaatga atggtgtgta tacatactct gtacattttt cttttctcct gtaatatagt 5520
cttgtcacct tagagcttgt ttatggaaga ttcaagaaaa ctataaaata cttaaagata 5580
tataaattta aaaaaacata gctgcaggtc tttggtccca gggctgtgcc ttaactttaa 5640
ccaatatttt cttctgtttt gctgcatttg aaaggtaaca gtggagctag ggctgggcat 5700
tttacatcca ggcttttaat tgattagaat tctgccaata ggtggatttt acaaaaccac 5760
agacaacctc tgaaagattc tgagaccctt ttgagacaga agctcttaag tacttcttgc 5820
cagggagcag cactgcatgt gtgatggttg tttgccatct gttgatcagg aactacttca 5880
gctacttgca tttgattatt tccttttttt ttttttttaa ctcggaaaca caactgggga 5940
aatatattct ttcccagtga ttataaacaa tctttttctt ttttttaagt ccttttggct 6000
tctagagctc ataggaaaat ggacttgatt tgaaattgga gccagagttt actcgtgttg 6060
gttatctatt catcagcttc ctgacatgtt aagagaatac attaaagaga aaatactgtt 6120
ttttaatcct aaaatttttc ttccactaag ataaaccaaa tgtccttaca tatatgtaaa 6180
cccatctatt taaacgcaaa ggtgggttga tgtcagttta catagcagaa agcattcact 6240
atcctctaag atttgtttct gcaaaacttt cattgcttta gaattttaaa atttcacctt 6300
gtacaatggc cagcccctaa agcaggaaac atttataatg gattatatgg aaacatcctc 6360
ccagtacttg cccagccctt gaatcatgtg gcttttcagt gaaaggaaag attctttttc 6420
taggaaaaat gagcctattt tattttattt tattttattt tttgacacaa actgtagatt 6480
ttagcagccc tggcccaaag gaatttgatt acttttgttt taaacagtac aaaggggaca 6540
ctataattac aaaaacatcc ttaactgatt tgagttgttt ttatttcttt ggatatattt 6600
tcagagtggt aaattgtgtg tgagaattac aaatgattat tcttttagtg gtttcttagc 6660
ctctcttaca gcccacgggg atagtactgt acatcaatac cttcatatga aatttttata 6720
tgcaatgaaa ataaaagcat gggttgattc tgcctattta tgactcaatc ttttacaaat 6780
aaaagattat tcattttaaa ttatagttca atcagcatgt ctcttaggat actgaacgtg 6840
gttgaaatga aaggatagtg acatcataag ttagtactga tattcataac caaataaagc 6900
caacttgagt aattttgcta cattaaaaat taccaaaatt acttagatgg cctataagat 6960
taagcatggt gttttctaag caagctttga aaggggcctt ccatacttac ttaattgaat 7020
attctgggat attgaaaatt attcagatac ttgacaatta tttttggtta cctactccgc 7080
aaactacaaa gttttaagga ctcaacaata agttaatgag acacagtgtt tgctttcatg 7140
gagcttacag tctggagggg acaaaggctt aaacaatact catataatta tatatgtgat 7200
cagtacaatg aaggagctca gtggggtaaa taagcaggaa cctgaacttg atctgttccg 7260
gagggccaca gaaggcttcc ttgaggcctt gagaaagtga tttgcatctg agttctgaag 7320
gattgtaaga ggtaactagg gaaaaagttg acaggaagag gaaggggatc cagacaagaa 7380
acatttgcaa agatcttgag gcataaatga gcttgagaca tctggagaaa ctgaggaaaa 7440
gtgagagagt aggcagggcc tggagccgca gagccattgc taaccatcct gtgtgagata 7500
tcccccattc tgtagcttta ttctcataac cctgctcaat tttctttata acacttctca 7560
cagatttata tacgtgtttg tttttgttat ctgtctctcc caccagacca cagctccatg 7620
agagcaaggt ctttgcttac caatatatca ctagcactta aaactatgcc tggtacacag 7680
taggttctta atatgtgttg aatatagcca tcaaattgat attggatata attcaatctg 7740
ataagatatt ttgagatatt aaagagtttt taacttgata ccataaaaaa aaaaaaaaaa 7800

-continued a 7801

<210> SEQ ID NO 2
<211> LENGTH: 585
<212> TYPE: PRT
<213> ORGANISM: Homo sapiens

<400> SEQUENCE: 2

```
Met Lys Glu Gln Pro Ser Cys Ala Gly Thr Gly His Pro Ser Met Ala
1               5                   10                  15

Gly Tyr Gly Arg Met Ala Pro Phe Glu Leu Ala Ser Gly Pro Val Lys
            20                  25                  30

Arg Leu Arg Thr Glu Ser Pro Phe Pro Cys Leu Phe Ala Glu Glu Ala
        35                  40                  45

Tyr Gln Lys Leu Ala Ser Glu Thr Leu Glu Glu Leu Asp Trp Cys Leu
    50                  55                  60

Asp Gln Leu Glu Thr Leu Gln Thr Arg His Ser Val Ser Glu Met Ala
65                  70                  75                  80

Ser Asn Lys Phe Lys Arg Met Leu Asn Arg Glu Leu Thr His Leu Ser
                85                  90                  95

Glu Met Ser Arg Ser Gly Asn Gln Val Ser Glu Phe Ile Ser Asn Thr
            100                 105                 110

Phe Leu Asp Lys Gln His Glu Val Glu Ile Pro Ser Pro Thr Gln Lys
        115                 120                 125

Glu Lys Glu Lys Lys Lys Arg Pro Met Ser Gln Ile Ser Gly Val Lys
    130                 135                 140

Lys Leu Met His Ser Ser Ser Leu Thr Asn Ser Ser Ile Pro Arg Phe
145                 150                 155                 160

Gly Val Lys Thr Glu Gln Glu Asp Val Leu Ala Lys Glu Leu Glu Asp
                165                 170                 175

Val Asn Lys Trp Gly Leu His Val Phe Arg Ile Ala Glu Leu Ser Gly
            180                 185                 190

Asn Arg Pro Leu Thr Val Ile Met His Thr Ile Phe Gln Glu Arg Asp
        195                 200                 205

Leu Leu Lys Thr Phe Lys Ile Pro Val Asp Thr Leu Ile Thr Tyr Leu
    210                 215                 220

Met Thr Leu Glu Asp His Tyr His Ala Asp Val Ala Tyr His Asn Asn
225                 230                 235                 240

Ile His Ala Ala Asp Val Val Gln Ser Thr His Val Leu Leu Ser Thr
                245                 250                 255

Pro Ala Leu Glu Ala Val Phe Thr Asp Leu Glu Ile Leu Ala Ala Ile
            260                 265                 270

Phe Ala Ser Ala Ile His Asp Val Asp His Pro Gly Val Ser Asn Gln
        275                 280                 285

Phe Leu Ile Asn Thr Asn Ser Glu Leu Ala Leu Met Tyr Asn Asp Ser
    290                 295                 300

Ser Val Leu Glu Asn His His Leu Ala Val Gly Phe Lys Leu Leu Gln
305                 310                 315                 320

Glu Glu Asn Cys Asp Ile Phe Gln Asn Leu Thr Lys Lys Gln Arg Gln
                325                 330                 335

Ser Leu Arg Lys Met Val Ile Asp Ile Val Leu Ala Thr Asp Met Ser
            340                 345                 350

Lys His Met Asn Leu Leu Ala Asp Leu Lys Thr Met Val Glu Thr Lys
        355                 360                 365
```

```
Lys Val Thr Ser Ser Gly Val Leu Leu Leu Asp Asn Tyr Ser Asp Arg
    370                 375                 380

Ile Gln Val Leu Gln Asn Met Val His Cys Ala Asp Leu Ser Asn Pro
385                 390                 395                 400

Thr Lys Pro Leu Gln Leu Tyr Arg Gln Trp Thr Asp Arg Ile Met Glu
                405                 410                 415

Glu Phe Phe Arg Gln Gly Asp Arg Glu Arg Glu Arg Gly Met Glu Ile
            420                 425                 430

Ser Pro Met Cys Asp Lys His Asn Ala Ser Val Glu Lys Ser Gln Val
        435                 440                 445

Gly Phe Ile Asp Tyr Ile Val His Pro Leu Trp Glu Thr Trp Ala Asp
    450                 455                 460

Leu Val His Pro Asp Ala Gln Asp Ile Leu Asp Thr Leu Glu Asp Asn
465                 470                 475                 480

Arg Glu Trp Tyr Gln Ser Thr Ile Pro Gln Ser Pro Ser Pro Ala Pro
                485                 490                 495

Asp Asp Pro Glu Glu Gly Arg Gln Gly Gln Thr Glu Lys Phe Gln Phe
            500                 505                 510

Glu Leu Thr Leu Glu Glu Asp Gly Glu Ser Asp Thr Glu Lys Asp Ser
        515                 520                 525

Gly Ser Gln Val Glu Glu Asp Thr Ser Cys Ser Asp Ser Lys Thr Leu
    530                 535                 540

Cys Thr Gln Asp Ser Glu Ser Thr Glu Ile Pro Leu Asp Glu Gln Val
545                 550                 555                 560

Glu Glu Glu Ala Val Gly Glu Glu Glu Glu Ser Gln Pro Glu Ala Cys
                565                 570                 575

Val Ile Asp Asp Arg Ser Pro Asp Thr
            580                 585
```

<210> SEQ ID NO 3
<211> LENGTH: 21
<212> TYPE: DNA
<213> ORGANISM: Artificial Sequence
<220> FEATURE:
<223> OTHER INFORMATION: PDE4D1D2_forward primer

<400> SEQUENCE: 3
aatatgaagg agcagccctc a 21

<210> SEQ ID NO 4
<211> LENGTH: 18
<212> TYPE: DNA
<213> ORGANISM: Artificial Sequence
<220> FEATURE:
<223> OTHER INFORMATION: PDE4D1D2_reverse primer

<400> SEQUENCE: 4
gtctcgctgg ccagtttc 18

<210> SEQ ID NO 5
<211> LENGTH: 18
<212> TYPE: DNA
<213> ORGANISM: Artificial Sequence
<220> FEATURE:
<223> OTHER INFORMATION: PDE4D1D2 probe

<400> SEQUENCE: 5
catccgagca tggcggga 18

<210> SEQ ID NO 6
<211> LENGTH: 7715
<212> TYPE: DNA
<213> ORGANISM: Homo sapiens

<400> SEQUENCE: 6
gtggtggccg cgcacccggc cgcggctgat tcattcactt caagtgccgt gcagaaggct 60
cggcaggcgg ggcgggcgtg gggccgcggc tccgggttgg ggaccgagga gatccggctg 120
tggaccagac gctcctctgc ggggcgggca cccaagcgcg ctcgccaccc cctcgccatc 180
cgctagagcc gggctcctgg actgggactc gggcccgccg cacagttgaa aagtcgcata 240
gtggtttttc cgctcgcgtc gctgtgtgaa agttggctcg ccgctctttg cacgccctcc 300
ctggaggccg acccgagacg ccaagctgga gagaccgtgc ctccccgagg ccggccgccc 360
cgcgagcaca gcctccgccc ccgttgcact gccgggctgg gcaatatgaa ggagcagccc 420
tcatgtgccg gcaccgggca tccgagcatg gcgggaggag gcctaccaga aactggccag 480
cgagaccctg gaggagctgg actggtgtct ggaccagcta gagaccctac agaccaggca 540
ctccgtcagt gagatggcct ccaacaagtt taaaaggatg cttaatcggg agctcaccca 600
tctctctgaa atgagtcggt ctggaaatca agtgtcagag tttatatcaa acacattctt 660
agataagcaa catgaagtgg aaattccttc tccaactcag aaggaaaagg agaaaaagaa 720
aagaccaatg tctcagatca gtggagtcaa gaaattgatg cacagctcta gtctgactaa 780
ttcaagtatc ccaaggtttg gagttaaaac tgaacaagaa gatgtccttg ccaaggaact 840
agaagatgtg aacaaatggg gtcttcatgt tttcagaata gcagagttgt ctggtaaccg 900
gcccttgact gttatcatgc acaccatttt tcaggaacgg gatttattaa aaacatttaa 960
aattccagta gatactttaa ttacatatct tatgactctc gaagaccatt accatgctga 1020
tgtggcctat cacaacaata tccatgctgc agatgttgtc cagtctactc atgtgctatt 1080
atctacacct gctttggagg ctgtgtttac agatttggag attcttgcag caatttttgc 1140
cagtgcaata catgatgtag atcatcctgg tgtgtccaat caatttctga tcaatacaaa 1200
ctctgaactt gccttgatgt acaatgattc ctcagtctta gagaaccatc atttggctgt 1260
gggctttaaa ttgcttcagg aagaaaactg tgacattttc cagaatttga ccaaaaaaca 1320
aagacaatct ttaaggaaaa tggtcattga catcgtactt gcaacagata tgtcaaaaca 1380
catgaatcta ctggctgatt tgaagactat ggttgaaact aagaaagtga caagctctgg 1440
agttcttctt cttgataatt attccgatag gattcaggtt cttcagaata tggtgcactg 1500
tgcagatctg agcaacccaa caaagcctct ccagctgtac cgccagtgga cggaccggat 1560
aatggaggag ttcttccgcc aaggagaccg agagagggaa cgtggcatgg agataagccc 1620
catgtgtgac aagcacaatg cttccgtgga aaaatcacag gtgggcttca tagactatat 1680
tgttcatccc ctctgggaga catgggcaga cctcgtccac cctgacgccc aggatatttt 1740
ggacactttg gaggacaatc gtgaatggta ccagagcaca atccctcaga gcccctctcc 1800
tgcacctgat gacccagagg agggccggca gggtcaaact gagaaattcc agtttgaact 1860
aactttagag gaagatggtg agtcagacac ggaaaaggac agtggcagtc aagtggaaga 1920
agacactagc tgcagtgact ccaagactct ttgtactcaa gactcagagt ctactgaaat 1980
tccccttgat gaacaggttg aagaggaggc agtaggggaa gaagaggaaa gccagcctga 2040
agcctgtgtc atagatgatc gttctcctga cacgtaacag tgcaaaaact ttcatgcctt 2100
ttttttttt aagtagaaaa attgtttcca aagtgcatgt cacatgccac aaccacggtc 2160

-continued

```
acacctcact gtcatctgcc aggacgtttg ttgaacaaaa ctgaccttga ctactcagtc   2220
cagcgctcag gaatatcgta accagttttt tcacctccat gtcatccgag caaggtggac   2280
atcttcacga acagcgtttt taacaagatt tcagcttggt agagctgaca aagcagataa   2340
aatctactcc aaattatttt caagagagtg tgactcatca ggcagcccaa aagtttattg   2400
gacttggggt ttctattcct ttttatttgt ttgcaatatt ttcagaagaa aggcattgca   2460
cagagtgaac ttaatggacg aagcaacaaa tatgtcaaga acaggacata gcacgaatct   2520
gttaccagta ggaggaggat gagccacaga aattgcataa ttttctaatt tcaagtcttc   2580
ctgatacatg actgaatagt gtggttcagt gagctgcact gacctctaca ttttgtatga   2640
tatgtaaaac agatttttttg tagagcttac ttttattatt aaatgtattg aggtattata   2700
tttaaaaaaa actatgttca gaacttcatc tgccactggt tatttttttc taaggagtaa   2760
cttgcaagtt ttcagtacaa atctgtgcta cactggataa aaatctaatt tatgaatttt   2820
acttgcacct tatagttcat agcaattaac tgatttgtag tgattcattg tttgttttat   2880
ataccaatga cttccatatt ttaaaagaga aaaacaactt tatgttgcag gaaacccttt   2940
ttgtaagtct ttattattta ctttgcattt tgtttcactc tttccagata agcagagttg   3000
ctcttcacca gtgtttttct tcatgtgcaa agtgactatt tgttctataa tacttttatg   3060
tgtgttatat caaatgtgtc ttaagcttca tgcaaactca gtcatcagtt cgtgttgtct   3120
gaagcaagtg ggagatatat aaatacccag tagctaaaat ggtcagtctt ttttagatgt   3180
tttcctactt agtatctcct aataacgttt tgctgtgtca ctagatgttc atttcacaag   3240
tgcatgtctt tctaataatc cacacatttc atgctctaat aatccacaca tttcatgctc   3300
atttttattg tttttacagc cagttatagt aagaaaaagg tttttcccct tgtgctgctt   3360
tataatttag cgtgtgtctg aaccttatcc atgtttgcta gatgaggtct tgtcaaatat   3420
atcactacca ttgtcaccgg tgaaaagaaa caggtagtta agttagggtt aacattcatt   3480
tcaaccacga ggttgtatat catgactagc ttttactctt ggtttacaga gaaaagttaa   3540
acagccaact aggcagtttt taagaatatt aacaatatat taacaaacac caatacaact   3600
aatcctattt ggttttaatg atttcaccat gggattaaga actatatcag gaacatccct   3660
gagaaacggt tttaagtgta gcaactactc ttccttaatg gacagccaca taacgtgtag   3720
gaagtccttt atcacttatc ctcgatccat aagcatatct tgcagagggg aactacttct   3780
ttaaacacat ggagggaaag aagatgatgc cactggcacc agagggttag tactgtgatg   3840
catcctaaaa tatttattat attggtaaaa attctggtta aataaaaaat tagagatcac   3900
tcttggctga tttcagcacc aggaactgta ttacagtttt agagattaat tcctagtgtt   3960
tacctgatta tagcagttgg catcatgggg catttaattc tgactttatc cccacgtcag   4020
ccttaataaa gtcttcttta ccttctctat gaagacttta aagcccaaat aatcattttt   4080
cacattgata ttcaagaatt gagatagata gaagccaaag tgggtatctg acaagtggaa   4140
aatcaaacgt ttaagaagaa ttacaactct gaaaagcatt tatatgtgga acttctcaag   4200
gagcctcctg gggactggaa agtaagtcat cagccaggca aatgactcat gctgaagaga   4260
gtccccattt cagtcccctg agatctagct gatgcttaga tcctttgaaa taaaaattat   4320
gtctttataa ctctgatctt ttacataaag cagaagagga atcaactagt taattgcaag   4380
gtttctactc tgtttcctct gtaaagatca gatggtaatc tttcaaataa gaaaaaaata   4440
aagacgtatg tttgaccaag tagtttcaca agaatatttg ggaacttgtt tcttttaatt   4500
ttatttgtcc ctgagtgaag tctagaaaga aaggtaaaga gtctagagtt tattcctctt   4560
```

-continued

```
tccaaaacat tctcattcct ctcctcccta cacttagtat ttcccccaca gagtgcctag   4620
aatcttaata atgaataaaa taaaaagcag caatatgtca ttaacaaatc cagacctgaa   4680
agggtaaagg gtttataact gcactaataa agagaggctc ttttttttc ttccagtttg   4740
ttggttttta atggtaccgt gttgtaaaga tacccactaa tggacaatca aattgcagaa   4800
aaggctcaat atccaagaga cagggactaa tgcactgtac aatctgctta tccttgccct   4860
tctctcttgc caaagtgtgc ttcagaaata tatactgctt taaaaaagaa taaaagaata   4920
tcctttaca agtggcttta catttcctaa aatgccataa gaaaatgcaa tatctgggta   4980
ctgtatgggg aaaaaaatgt ccaagtttgt gtaaaaccag tgcatttcag cttgcaagtt   5040
actgaacaca ataatgctgt tttaattttg ttttatatca gttaaaattc acaataatgt   5100
agatagaaca aattacagac aaggaaagaa aaaacttgaa tgaaatggat tttacagaaa   5160
gctttatgat aatttttgaa tgcattattt attttttgtg ccatgcattt tttttctcac   5220
caaatgacct tacctgtaat acagtcttgt ttgtctgttt acaaccatgt atttattgca   5280
atgtacatac tgtaatgtta attgtaaatt atctgttctt attaaaacat catcccatga   5340
tgggatggtg ttgatatatt tggaaactct tggtgagaga atgaatggtg tgtatacata   5400
ctctgtacat ttttctttc tcctgtaata tagtcttgtc accttagagc ttgtttatgg   5460
aagattcaag aaaactataa aatacttaaa gatatataaa tttaaaaaaa catagctgca   5520
ggtctttggt cccagggctg tgccttaact ttaaccaata ttttcttctg ttttgctgca   5580
tttgaaaggt aacagtggag ctagggctgg gcattttaca tccaggcttt taattgatta   5640
gaattctgcc aataggtgga ttttacaaaa ccacagacaa cctctgaaag attctgagac   5700
ccttttgaga cagaagctct taagtacttc ttgccaggga gcagcactgc atgtgtgatg   5760
gttgtttgcc atctgttgat caggaactac ttcagctact tgcatttgat tatttccttt   5820
tttttttt ttaactcgga aacacaactg gggaaatata ttctttccca gtgattataa   5880
acaatctttt tcttttttt aagtcctttt ggcttctaga gctcatagga aaatggactt   5940
gatttgaaat tggagccaga gtttactcgt gttggttatc tattcatcag cttcctgaca   6000
tgttaagaga atacattaaa gagaaaatac tgttttttaa tcctaaaatt tttcttccac   6060
taagataaac caaatgtcct tacatatatg taaacccatc tatttaaacg caaaggtggg   6120
ttgatgtcag tttacatagc agaaagcatt cactatcctc taagatttgt ttctgcaaaa   6180
ctttcattgc tttagaattt taaaatttca ccttgtacaa tggccagccc ctaaagcagg   6240
aaacatttat aatggattat atggaaacat cctcccagta cttgcccagc ccttgaatca   6300
tgtggctttt cagtgaaagg aaagattctt tttctaggaa aaatgagcct attttatttt   6360
attttatttt attttttgac acaaactgta gattttagca gccctggccc aaaggaattt   6420
gattactttt gttttaaaca gtacaaaggg gacactataa ttacaaaaac atccttaact   6480
gatttgagtt gtttttattt ctttggatat attttcagag tggtaaattg tgtgtgagaa   6540
ttacaaatga ttattctttt agtggtttct tagcctctct tacagcccac ggggatagta   6600
ctgtacatca ataccttcat atgaaatttt tatatgcaat gaaaataaaa gcatgggttg   6660
attctgccta tttatgactc aatcttttac aaataaaaga ttattcattt taaattatag   6720
ttcaatcagc atgtctctta ggatactgaa cgtggttgaa atgaaaggat agtgacatca   6780
taagttagta ctgatattca taaccaaata aagccaactt gagtaatttt gctacattaa   6840
aaattaccaa aattacttag atggcctata agattaagca tggtgttttc taagcaagct   6900
```

-continued

```
ttgaaagggg ccttccatac ttacttaatt gaatattctg ggatattgaa aattattcag   6960

atacttgaca attatttttg gttacctact ccgcaaacta caaagtttta aggactcaac   7020

aataagttaa tgagacacag tgtttgcttt catggagctt acagtctgga ggggacaaag   7080

gcttaaacaa tactcatata attatatatg tgatcagtac aatgaaggag ctcagtgggg   7140

taaataagca ggaacctgaa cttgatctgt tccggagggc cacagaaggc ttccttgagg   7200

ccttgagaaa gtgatttgca tctgagttct gaaggattgt aagaggtaac tagggaaaaa   7260

gttgacagga agaggaaggg gatccagaca agaaacattt gcaaagatct tgaggcataa   7320

atgagcttga gacatctgga gaaactgagg aaaagtgaga gagtaggcag ggcctggagc   7380

cgcagagcca ttgctaacca tcctgtgtga gatatccccc attctgtagc tttattctca   7440

taaccctgct caattttctt tataacactt ctcacagatt tatatacgtg tttgtttttg   7500

ttatctgtct ctcccaccag accacagctc catgagagca aggtctttgc ttaccaatat   7560

atcactagca cttaaaacta tgcctggtac acagtaggtt cttaatatgt gttgaatata   7620

gccatcaaat tgatattgga tataattcaa tctgataaga tattttgaga tattaaagag   7680

tttttaactt gataccataa aaaaaaaaaa aaaaa                              7715


<210> SEQ ID NO 7
<211> LENGTH: 507
<212> TYPE: PRT
<213> ORGANISM: Homo sapiens

<400> SEQUENCE: 7

Met Ala Ser Asn Lys Phe Lys Arg Met Leu Asn Arg Glu Leu Thr His
1               5                   10                  15

Leu Ser Glu Met Ser Arg Ser Gly Asn Gln Val Ser Glu Phe Ile Ser
            20                  25                  30

Asn Thr Phe Leu Asp Lys Gln His Glu Val Glu Ile Pro Ser Pro Thr
        35                  40                  45

Gln Lys Glu Lys Glu Lys Lys Lys Arg Pro Met Ser Gln Ile Ser Gly
    50                  55                  60

Val Lys Lys Leu Met His Ser Ser Ser Leu Thr Asn Ser Ser Ile Pro
65                  70                  75                  80

Arg Phe Gly Val Lys Thr Glu Gln Glu Asp Val Leu Ala Lys Glu Leu
                85                  90                  95

Glu Asp Val Asn Lys Trp Gly Leu His Val Phe Arg Ile Ala Glu Leu
            100                 105                 110

Ser Gly Asn Arg Pro Leu Thr Val Ile Met His Thr Ile Phe Gln Glu
        115                 120                 125

Arg Asp Leu Leu Lys Thr Phe Lys Ile Pro Val Asp Thr Leu Ile Thr
    130                 135                 140

Tyr Leu Met Thr Leu Glu Asp His Tyr His Ala Asp Val Ala Tyr His
145                 150                 155                 160

Asn Asn Ile His Ala Ala Asp Val Val Gln Ser Thr His Val Leu Leu
                165                 170                 175

Ser Thr Pro Ala Leu Glu Ala Val Phe Thr Asp Leu Glu Ile Leu Ala
            180                 185                 190

Ala Ile Phe Ala Ser Ala Ile His Asp Val Asp His Pro Gly Val Ser
        195                 200                 205

Asn Gln Phe Leu Ile Asn Thr Asn Ser Glu Leu Ala Leu Met Tyr Asn
    210                 215                 220

Asp Ser Ser Val Leu Glu Asn His His Leu Ala Val Gly Phe Lys Leu
```

-continued

```
225                 230                 235                 240

Leu Gln Glu Glu Asn Cys Asp Ile Phe Gln Asn Leu Thr Lys Lys Gln
                245                 250                 255

Arg Gln Ser Leu Arg Lys Met Val Ile Asp Ile Val Leu Ala Thr Asp
            260                 265                 270

Met Ser Lys His Met Asn Leu Leu Ala Asp Leu Lys Thr Met Val Glu
        275                 280                 285

Thr Lys Lys Val Thr Ser Ser Gly Val Leu Leu Leu Asp Asn Tyr Ser
    290                 295                 300

Asp Arg Ile Gln Val Leu Gln Asn Met Val His Cys Ala Asp Leu Ser
305                 310                 315                 320

Asn Pro Thr Lys Pro Leu Gln Leu Tyr Arg Gln Trp Thr Asp Arg Ile
                325                 330                 335

Met Glu Glu Phe Phe Arg Gln Gly Asp Arg Glu Arg Glu Arg Gly Met
            340                 345                 350

Glu Ile Ser Pro Met Cys Asp Lys His Asn Ala Ser Val Glu Lys Ser
        355                 360                 365

Gln Val Gly Phe Ile Asp Tyr Ile Val His Pro Leu Trp Glu Thr Trp
    370                 375                 380

Ala Asp Leu Val His Pro Asp Ala Gln Asp Ile Leu Asp Thr Leu Glu
385                 390                 395                 400

Asp Asn Arg Glu Trp Tyr Gln Ser Thr Ile Pro Gln Ser Pro Ser Pro
                405                 410                 415

Ala Pro Asp Asp Pro Glu Glu Gly Arg Gln Gly Gln Thr Glu Lys Phe
            420                 425                 430

Gln Phe Glu Leu Thr Leu Glu Glu Asp Gly Glu Ser Asp Thr Glu Lys
        435                 440                 445

Asp Ser Gly Ser Gln Val Glu Glu Asp Thr Ser Cys Ser Asp Ser Lys
    450                 455                 460

Thr Leu Cys Thr Gln Asp Ser Glu Ser Thr Glu Ile Pro Leu Asp Glu
465                 470                 475                 480

Gln Val Glu Glu Glu Ala Val Gly Glu Glu Glu Glu Ser Gln Pro Glu
                485                 490                 495

Ala Cys Val Ile Asp Asp Arg Ser Pro Asp Thr
            500                 505
```

<210> SEQ ID NO 8
<211> LENGTH: 7783
<212> TYPE: DNA
<213> ORGANISM: Homo sapiens

<400> SEQUENCE: 8

```
aatacttgtt gcaataattg cccacgatag ctgctcaaac aagagagttg gaattcatct     60

gtaaaaatca ctacatgtaa cgtaggagac aagaaaaata ttaatgacag aagatctgcg    120

aacatgatgc acgtgaataa ttttcccttt agaaggcatt cctggatatg ttttgatgtg    180

gacaatggca catctgcggg acggagtccc ttggatccca tgaccagccc aggatccggg    240

ctaattctcc aagcaaattt tgtccacagt caacgacggg agtccttcct gtatcgatcc    300

gacagcgatt atgacctctc tccaaagtct atgtcccgga actcctccat tgccagtgat    360

atacacggag atgacttgat tgtgactcca tttgctcagg tcttggccag tctgcgaact    420

gtacgaaaca actttgctgc attaactaat ttgcaagatc gagcacctag caaaagatca    480

cccatgtgca accaaccatc catcaacaaa gccaccataa cagaggaggc ctaccagaaa    540
```

-continued

```
ctggccagcg agaccctgga ggagctggac tggtgtctgg accagctaga gaccctacag    600
accaggcact ccgtcagtga gatggcctcc aacaagttta aaaggatgct taatcgggag    660
ctcacccatc tctctgaaat gagtcggtct ggaaatcaag tgtcagagtt tatatcaaac    720
acattcttag ataagcaaca tgaagtggaa attccttctc caactcagaa ggaaaaggag    780
aaaaagaaaa gaccaatgtc tcagatcagt ggagtcaaga aattgatgca cagctctagt    840
ctgactaatt caagtatccc aaggtttgga gttaaaactg aacaagaaga tgtccttgcc    900
aaggaactag aagatgtgaa caaatggggt cttcatgttt tcagaatagc agagttgtct    960
ggtaaccggc ccttgactgt tatcatgcac accatttttc aggaacggga tttattaaaa   1020
acatttaaaa ttccagtaga tactttaatt acatatctta tgactctcga agaccattac   1080
catgctgatg tggcctatca caacaatatc catgctgcag atgttgtcca gtctactcat   1140
gtgctattat ctacacctgc tttggaggct gtgtttacag atttggagat tcttgcagca   1200
atttttgcca gtgcaataca tgatgtagat catcctggtg tgtccaatca atttctgatc   1260
aatacaaact ctgaacttgc cttgatgtac aatgattcct cagtcttaga gaaccatcat   1320
ttggctgtgg gctttaaatt gcttcaggaa gaaaactgtg acattttcca gaatttgacc   1380
aaaaaacaaa gacaatcttt aaggaaaatg gtcattgaca tcgtacttgc aacagatatg   1440
tcaaaacaca tgaatctact ggctgatttg aagactatgg ttgaaactaa gaaagtgaca   1500
agctctggag ttcttcttct tgataattat tccgatagga ttcaggttct tcagaatatg   1560
gtgcactgtg cagatctgag caacccaaca aagcctctcc agctgtaccg ccagtggacg   1620
gaccggataa tggaggagtt cttccgccaa ggagaccgag agagggaacg tggcatggag   1680
ataagcccca tgtgtgacaa gcacaatgct tccgtggaaa aatcacaggt gggcttcata   1740
gactatattg ttcatcccct ctgggagaca tgggcagacc tcgtccaccc tgacgcccag   1800
gatattttgg acactttgga ggacaatcgt gaatggtacc agagcacaat ccctcagagc   1860
ccctctcctg cacctgatga cccagaggag ggccggcagg gtcaaactga gaaattccag   1920
tttgaactaa ctttagagga agatggtgag tcagacacgg aaaaggacag tggcagtcaa   1980
gtggaagaag acactagctg cagtgactcc aagactcttt gtactcaaga ctcagagtct   2040
actgaaattc cccttgatga acaggttgaa gaggaggcag taggggaaga agaggaaagc   2100
cagcctgaag cctgtgtcat agatgatcgt tctcctgaca cgtaacagtg caaaaacttt   2160
catgcctttt tttttttaa gtagaaaaat tgtttccaaa gtgcatgtca catgccacaa   2220
ccacggtcac acctcactgt catctgccag gacgtttgtt gaacaaaact gaccttgact   2280
actcagtcca gcgctcagga atatcgtaac cagtttttc acctccatgt catccgagca    2340
aggtggacat cttcacgaac agcgttttta acaagatttc agcttggtag agctgacaaa   2400
gcagataaaa tctactccaa attattttca agagagtgtg actcatcagg cagcccaaaa   2460
gtttattgga cttggggttt ctattccttt ttatttgttt gcaatatttt cagaagaaag   2520
gcattgcaca gagtgaactt aatggacgaa gcaacaaata tgtcaagaac aggacatagc   2580
acgaatctgt taccagtagg aggaggatga gccacagaaa ttgcataatt ttctaatttc   2640
aagtcttcct gatacatgac tgaatagtgt ggttcagtga gctgcactga cctctacatt   2700
ttgtatgata tgtaaaacag attttttgta gagcttactt ttattattaa atgtattgag   2760
gtattatatt taaaaaaaac tatgttcaga acttcatctg ccactggtta ttttttttcta   2820
aggagtaact tgcaagtttt cagtacaaat ctgtgctaca ctggataaaa atctaattta   2880
tgaattttac ttgcacctta tagttcatag caattaactg atttgtagtg attcattgtt   2940
```

tgttttatat accaatgact tccatatttt aaaagagaaa aacaacttta tgttgcagga 3000
aacccttttt gtaagtcttt attatttact ttgcattttg tttcactctt tccagataag 3060
cagagttgct cttcaccagt gtttttcttc atgtgcaaag tgactatttg ttctataata 3120
cttttatgtg tgttatatca aatgtgtctt aagcttcatg caaactcagt catcagttcg 3180
tgttgtctga agcaagtggg agatatataa atacccagta gctaaaatgg tcagtctttt 3240
ttagatgttt tcctacttag tatctcctaa taacgttttg ctgtgtcact agatgttcat 3300
ttcacaagtg catgtctttc taataatcca cacatttcat gctctaataa tccacacatt 3360
tcatgctcat ttttattgtt tttacagcca gttatagtaa gaaaaaggtt tttccccttg 3420
tgctgcttta taatttagcg tgtgtctgaa ccttatccat gtttgctaga tgaggtcttg 3480
tcaaatatat cactaccatt gtcaccggtg aaaagaaaca ggtagttaag ttagggttaa 3540
cattcatttc aaccacgagg ttgtatatca tgactagctt ttactcttgg tttacagaga 3600
aaagttaaac agccaactag gcagtttttta agaatattaa caatatatta acaaacacca 3660
atacaactaa tcctatttgg ttttaatgat ttcaccatgg gattaagaac tatatcagga 3720
acatccctga gaaacggttt taagtgtagc aactactctt ccttaatgga cagccacata 3780
acgtgtagga agtcctttat cacttatcct cgatccataa gcatatcttg cagaggggaa 3840
ctacttcttt aaacacatgg agggaaagaa gatgatgcca ctggcaccag agggttagta 3900
ctgtgatgca tcctaaaata tttattatat tggtaaaaat tctggttaaa taaaaaatta 3960
gagatcactc ttggctgatt tcagcaccag gaactgtatt acagttttag agattaattc 4020
ctagtgttta cctgattata gcagttggca tcatggggca tttaattctg actttatccc 4080
cacgtcagcc ttaataaagt cttctttacc ttctctatga agactttaaa gcccaaataa 4140
tcatttttca cattgatatt caagaattga gatagataga agccaaagtg ggtatctgac 4200
aagtggaaaa tcaaacgttt aagaagaatt acaactctga aaagcattta tatgtggaac 4260
ttctcaagga gcctcctggg gactggaaag taagtcatca gccaggcaaa tgactcatgc 4320
tgaagagagt ccccatttca gtcccctgag atctagctga tgcttagatc ctttgaaata 4380
aaaattatgt ctttataact ctgatctttt acataaagca gaagaggaat caactagtta 4440
attgcaaggt ttctactctg tttcctctgt aaagatcaga tggtaatctt tcaaataaga 4500
aaaaaataaa gacgtatgtt tgaccaagta gtttcacaag aatatttggg aacttgtttc 4560
ttttaatttt atttgtccct gagtgaagtc tagaaagaaa ggtaaagagt ctagagttta 4620
ttcctctttc caaaacattc tcattcctct cctccctaca cttagtattt cccccacaga 4680
gtgcctagaa tcttaataat gaataaaata aaaagcagca atatgtcatt aacaaatcca 4740
gacctgaaag ggtaaagggt ttataactgc actaataaag agaggctctt tttttttctt 4800
ccagtttgtt ggtttttaat ggtaccgtgt tgtaaagata cccactaatg gacaatcaaa 4860
ttgcagaaaa ggctcaatat ccaagagaca gggactaatg cactgtacaa tctgcttatc 4920
cttgcccttc tctcttgcca aagtgtgctt cagaaatata tactgcttta aaaaagaata 4980
aaagaatatc cttttacaag tggctttaca tttcctaaaa tgccataaga aaatgcaata 5040
tctgggtact gtatggggaa aaaaatgtcc aagtttgtgt aaaaccagtg catttcagct 5100
tgcaagttac tgaacacaat aatgctgttt taattttgtt ttatatcagt taaaattcac 5160
aataatgtag atagaacaaa ttacagacaa ggaaagaaaa aacttgaatg aaatggattt 5220
tacagaaagc tttatgataa tttttgaatg cattatttat tttttgtgcc atgcattttt 5280

-continued

```
tttctcacca aatgacctta cctgtaatac agtcttgttt gtctgtttac aaccatgtat   5340
ttattgcaat gtacatactg taatgttaat tgtaaattat ctgttcttat taaaacatca   5400
tcccatgatg ggatggtgtt gatatatttg gaaactcttg gtgagagaat gaatggtgtg   5460
tatacatact ctgtacattt ttcttttctc ctgtaatata gtcttgtcac cttagagctt   5520
gtttatggaa gattcaagaa aactataaaa tacttaaaga tatataaatt taaaaaaaca   5580
tagctgcagg tctttggtcc cagggctgtg ccttaacttt aaccaatatt ttcttctgtt   5640
ttgctgcatt tgaaaggtaa cagtggagct agggctgggc attttacatc caggctttta   5700
attgattaga attctgccaa taggtggatt ttacaaaacc acagacaacc tctgaaagat   5760
tctgagaccc ttttgagaca gaagctctta agtacttctt gccagggagc agcactgcat   5820
gtgtgatggt tgtttgccat ctgttgatca ggaactactt cagctacttg catttgatta   5880
tttccttttt tttttttttt aactcggaaa cacaactggg gaaatatatt ctttcccagt   5940
gattataaac aatcttttc ttttttttaa gtccttttgg cttctagagc tcataggaaa   6000
atggacttga tttgaaattg gagccagagt ttactcgtgt tggttatcta ttcatcagct   6060
tcctgacatg ttaagagaat acattaaaga gaaaatactg tttttaatc ctaaaatttt    6120
tcttccacta agataaacca aatgtcctta catatatgta aacccatcta tttaaacgca   6180
aaggtgggtt gatgtcagtt tacatagcag aaagcattca ctatcctcta agatttgttt   6240
ctgcaaaact ttcattgctt tagaatttta aaatttcacc ttgtacaatg gccagcccct   6300
aaagcaggaa acatttataa tggattatat ggaaacatcc tcccagtact tgcccagccc   6360
ttgaatcatg tggcttttca gtgaaaggaa agattctttt tctaggaaaa atgagcctat   6420
tttattttat tttattttat tttttgacac aaactgtaga ttttagcagc cctggcccaa   6480
aggaatttga ttacttttgt tttaaacagt acaaagggga cactataatt acaaaaaacat  6540
ccttaactga tttgagttgt ttttatttct ttggatatat tttcagagtg gtaaattgtg   6600
tgtgagaatt acaaatgatt attcttttag tggtttctta gcctctctta cagcccacgg   6660
ggatagtact gtacatcaat accttcatat gaaattttta tatgcaatga aaataaaagc   6720
atgggttgat tctgcctatt tatgactcaa tcttttacaa ataaaagatt attcatttta   6780
aattatagtt caatcagcat gtctcttagg atactgaacg tggttgaaat gaaaggatag   6840
tgacatcata agttagtact gatattcata accaaataaa gccaacttga gtaattttgc   6900
tacattaaaa attaccaaaa ttacttagat ggcctataag attaagcatg gtgttttcta   6960
agcaagcttt gaaaggggcc ttccatactt acttaattga atattctggg atattgaaaa   7020
ttattcagat acttgacaat tatttttggt tacctactcc gcaaactaca aagttttaag   7080
gactcaacaa taagttaatg agacacagtg tttgctttca tggagcttac agtctggagg   7140
ggacaaaggc ttaaacaata ctcatataat tatatatgtg atcagtacaa tgaaggagct   7200
cagtggggta aataagcagg aacctgaact tgatctgttc cggagggcca cagaaggctt   7260
ccttgaggcc ttgagaaagt gatttgcatc tgagttctga aggattgtaa gaggtaacta   7320
gggaaaaagt tgacaggaag aggaagggga tccagacaag aaacatttgc aaagatcttg   7380
aggcataaat gagcttgaga catctggaga aactgaggaa aagtgagaga gtaggcaggg   7440
cctggagccg cagagccatt gctaaccatc ctgtgtgaga tatcccccat tctgtagctt   7500
tattctcata accctgctca attttcttta taacacttct cacagattta tatacgtgtt   7560
tgtttttgtt atctgtctct cccaccagac cacagctcca tgagagcaag gtctttgctt   7620
accaatatat cactagcact taaaactatg cctggtacac agtaggttct taatatgtgt   7680
```

-continued tgaatatagc catcaaattg atattggata taattcaatc tgataagata ttttgagata 7740
ttaaagagtt tttaacttga taccataaaa aaaaaaaaaa aaa 7783

<210> SEQ ID NO 9
<211> LENGTH: 673
<212> TYPE: PRT
<213> ORGANISM: Homo sapiens

<400> SEQUENCE: 9

Met Met His Val Asn Asn Phe Pro Phe Arg Arg His Ser Trp Ile Cys
1 5 10 15

Phe Asp Val Asp Asn Gly Thr Ser Ala Gly Arg Ser Pro Leu Asp Pro
20 25 30

Met Thr Ser Pro Gly Ser Gly Leu Ile Leu Gln Ala Asn Phe Val His
35 40 45

Ser Gln Arg Arg Glu Ser Phe Leu Tyr Arg Ser Asp Ser Asp Tyr Asp
50 55 60

Leu Ser Pro Lys Ser Met Ser Arg Asn Ser Ser Ile Ala Ser Asp Ile
65 70 75 80

His Gly Asp Asp Leu Ile Val Thr Pro Phe Ala Gln Val Leu Ala Ser
85 90 95

Leu Arg Thr Val Arg Asn Asn Phe Ala Ala Leu Thr Asn Leu Gln Asp
100 105 110

Arg Ala Pro Ser Lys Arg Ser Pro Met Cys Asn Gln Pro Ser Ile Asn
115 120 125

Lys Ala Thr Ile Thr Glu Glu Ala Tyr Gln Lys Leu Ala Ser Glu Thr
130 135 140

Leu Glu Glu Leu Asp Trp Cys Leu Asp Gln Leu Glu Thr Leu Gln Thr
145 150 155 160

Arg His Ser Val Ser Glu Met Ala Ser Asn Lys Phe Lys Arg Met Leu
165 170 175

Asn Arg Glu Leu Thr His Leu Ser Glu Met Ser Arg Ser Gly Asn Gln
180 185 190

Val Ser Glu Phe Ile Ser Asn Thr Phe Leu Asp Lys Gln His Glu Val
195 200 205

Glu Ile Pro Ser Pro Thr Gln Lys Glu Lys Glu Lys Lys Lys Arg Pro
210 215 220

Met Ser Gln Ile Ser Gly Val Lys Lys Leu Met His Ser Ser Ser Leu
225 230 235 240

Thr Asn Ser Ser Ile Pro Arg Phe Gly Val Lys Thr Glu Gln Glu Asp
245 250 255

Val Leu Ala Lys Glu Leu Glu Asp Val Asn Lys Trp Gly Leu His Val
260 265 270

Phe Arg Ile Ala Glu Leu Ser Gly Asn Arg Pro Leu Thr Val Ile Met
275 280 285

His Thr Ile Phe Gln Glu Arg Asp Leu Leu Lys Thr Phe Lys Ile Pro
290 295 300

Val Asp Thr Leu Ile Thr Tyr Leu Met Thr Leu Glu Asp His Tyr His
305 310 315 320

Ala Asp Val Ala Tyr His Asn Asn Ile His Ala Ala Asp Val Val Gln
325 330 335

Ser Thr His Val Leu Leu Ser Thr Pro Ala Leu Glu Ala Val Phe Thr
340 345 350

-continued

```
Asp Leu Glu Ile Leu Ala Ala Ile Phe Ala Ser Ala Ile His Asp Val
        355                 360                 365

Asp His Pro Gly Val Ser Asn Gln Phe Leu Ile Asn Thr Asn Ser Glu
    370                 375                 380

Leu Ala Leu Met Tyr Asn Asp Ser Ser Val Leu Glu Asn His His Leu
385                 390                 395                 400

Ala Val Gly Phe Lys Leu Leu Gln Glu Glu Asn Cys Asp Ile Phe Gln
                405                 410                 415

Asn Leu Thr Lys Lys Gln Arg Gln Ser Leu Arg Lys Met Val Ile Asp
            420                 425                 430

Ile Val Leu Ala Thr Asp Met Ser Lys His Met Asn Leu Leu Ala Asp
        435                 440                 445

Leu Lys Thr Met Val Glu Thr Lys Lys Val Thr Ser Ser Gly Val Leu
    450                 455                 460

Leu Leu Asp Asn Tyr Ser Asp Arg Ile Gln Val Leu Gln Asn Met Val
465                 470                 475                 480

His Cys Ala Asp Leu Ser Asn Pro Thr Lys Pro Leu Gln Leu Tyr Arg
                485                 490                 495

Gln Trp Thr Asp Arg Ile Met Glu Glu Phe Phe Arg Gln Gly Asp Arg
            500                 505                 510

Glu Arg Glu Arg Gly Met Glu Ile Ser Pro Met Cys Asp Lys His Asn
        515                 520                 525

Ala Ser Val Glu Lys Ser Gln Val Gly Phe Ile Asp Tyr Ile Val His
    530                 535                 540

Pro Leu Trp Glu Thr Trp Ala Asp Leu Val His Pro Asp Ala Gln Asp
545                 550                 555                 560

Ile Leu Asp Thr Leu Glu Asp Asn Arg Glu Trp Tyr Gln Ser Thr Ile
                565                 570                 575

Pro Gln Ser Pro Ser Pro Ala Pro Asp Asp Pro Glu Glu Gly Arg Gln
            580                 585                 590

Gly Gln Thr Glu Lys Phe Gln Phe Glu Leu Thr Leu Glu Glu Asp Gly
        595                 600                 605

Glu Ser Asp Thr Glu Lys Asp Ser Gly Ser Gln Val Glu Glu Asp Thr
    610                 615                 620

Ser Cys Ser Asp Ser Lys Thr Leu Cys Thr Gln Asp Ser Glu Ser Thr
625                 630                 635                 640

Glu Ile Pro Leu Asp Glu Gln Val Glu Glu Glu Ala Val Gly Glu Glu
                645                 650                 655

Glu Glu Ser Gln Pro Glu Ala Cys Val Ile Asp Asp Arg Ser Pro Asp
            660                 665                 670

Thr
```

<210> SEQ ID NO 10
<211> LENGTH: 8240
<212> TYPE: DNA
<213> ORGANISM: Homo sapiens

<400> SEQUENCE: 10

```
cccctctcgg tagccctgag gctctggcgc cttcaagtga gaagctaagc accagcctct      60

gctgggctgc agaagcggcg gcggcggcag cagcagcagc agcatcagga aggcgctcgg     120

gccagcgcgg tgaacccggg ctgggcagca ggtcgcggag ccgcgagcca ggatggaggc     180

agagggcagc agcgcgccgg cccgggcggg cagcggagag ggcagcgaca gcgccggcgg     240

ggccacgctc aaagccccca agcatctctg gaggcacgag cagcaccacc agtacccgct     300
```

-continued

```
ccggcagccc cagttccgcc tcctgcatcc ccatcaccac ctgccccgc cgccgccacc    360
ctcgccccag ccccagcccc agtgtccgct acagccgccg ccgccgcccc ccctgccgcc    420
gcccccgccg ccgcccgggg ctgcccgcgg ccgctacgcc tcgagcgggg ccaccggccg    480
cgtccggcat cgcggctact cggacaccga gcgctacctg tactgtcgcg ccatggaccg    540
cacctcctac gcggtggaga ccggccaccg gcccggcctg aagaaatcca ggatgtcctg    600
gccctcctcg ttccagggac tcaggcgttt tgatgtggac aatggcacat ctgcgggacg    660
gagtcccttg gatcccatga ccagcccagg atccgggcta attctccaag caaattttgt    720
ccacagtcaa cgacgggagt ccttcctgta tcgatccgac agcgattatg acctctctcc    780
aaagtctatg tcccggaact cctccattgc cagtgatata cacggagatg acttgattgt    840
gactccattt gctcaggtct tggccagtct gcgaactgta cgaaacaact ttgctgcatt    900
aactaatttg caagatcgag cacctagcaa aagatcaccc atgtgcaacc aaccatccat    960
caacaaagcc accataacag aggaggccta ccagaaactg gccagcgaga ccctggagga   1020
gctggactgg tgtctggacc agctagagac cctacagacc aggcactccg tcagtgagat   1080
ggcctccaac aagtttaaaa ggatgcttaa tcgggagctc acccatctct ctgaaatgag   1140
tcggtctgga aatcaagtgt cagagtttat atcaaacaca ttcttagata agcaacatga   1200
agtggaaatt ccttctccaa ctcagaagga aaaggagaaa aagaaaagac caatgtctca   1260
gatcagtgga gtcaagaaat tgatgcacag ctctagtctg actaattcaa gtatcccaag   1320
gtttggagtt aaaactgaac aagaagatgt ccttgccaag gaactagaag atgtgaacaa   1380
atggggtctt catgttttca gaatagcaga gttgtctggt aaccggccct tgactgttat   1440
catgcacacc atttttcagg aacgggattt attaaaaaca tttaaaattc cagtagatac   1500
tttaattaca tatcttatga ctctcgaaga ccattaccat gctgatgtgg cctatcacaa   1560
caatatccat gctgcagatg ttgtccagtc tactcatgtg ctattatcta cacctgcttt   1620
ggaggctgtg tttacagatt tggagattct tgcagcaatt tttgccagtg caatacatga   1680
tgtagatcat cctggtgtgt ccaatcaatt tctgatcaat acaaactctg aacttgcctt   1740
gatgtacaat gattcctcag tcttagagaa ccatcatttg gctgtgggct ttaaattgct   1800
tcaggaagaa aactgtgaca ttttccagaa tttgaccaaa aaacaaagac aatctttaag   1860
gaaaatggtc attgacatcg tacttgcaac agatatgtca aaacacatga atctactggc   1920
tgatttgaag actatggttg aaactaagaa agtgacaagc tctggagttc ttcttcttga   1980
taattattcc gataggattc aggttcttca gaatatggtg cactgtgcag atctgagcaa   2040
cccaacaaag cctctccagc tgtaccgcca gtggacggac cggataatgg aggagttctt   2100
ccgccaagga gaccgagaga gggaacgtgg catggagata agccccatgt gtgacaagca   2160
caatgcttcc gtggaaaaat cacaggtggg cttcatagac tatattgttc atcccctctg   2220
ggagacatgg gcagacctcg tccaccctga cgcccaggat attttggaca ctttggagga   2280
caatcgtgaa tggtaccaga gcacaatccc tcagagcccc tctcctgcac ctgatgaccc   2340
agaggagggc cggcagggtc aaactgagaa attccagttt gaactaactt tagaggaaga   2400
tggtgagtca gacacggaaa aggacagtgg cagtcaagtg gaagaagaca ctagctgcag   2460
tgactccaag actctttgta ctcaagactc agagtctact gaaattcccc ttgatgaaca   2520
ggttgaagag gaggcagtag gggaagaaga ggaaagccag cctgaagcct gtgtcataga   2580
tgatcgttct cctgacacgt aacagtgcaa aaactttcat gccttttttt tttttaagta   2640
```

-continued

```
gaaaaattgt ttccaaagtg catgtcacat gccacaacca cggtcacacc tcactgtcat   2700
ctgccaggac gtttgttgaa caaaactgac cttgactact cagtccagcg ctcaggaata   2760
tcgtaaccag tttttcacc tccatgtcat ccgagcaagg tggacatctt cacgaacagc   2820
gtttttaaca agatttcagc ttggtagagc tgacaaagca gataaaatct actccaaatt   2880
attttcaaga gagtgtgact catcaggcag cccaaaagtt tattggactt ggggtttcta   2940
ttccttttta tttgtttgca atattttcag aagaaaggca ttgcacagag tgaacttaat   3000
ggacgaagca acaaatatgt caagaacagg acatagcacg aatctgttac cagtaggagg   3060
aggatgagcc acagaaattg cataattttc taatttcaag tcttcctgat acatgactga   3120
atagtgtggt tcagtgagct gcactgacct ctacattttg tatgatatgt aaaacagatt   3180
ttttgtagag cttactttta ttattaaatg tattgaggta ttatatttaa aaaaaactat   3240
gttcagaact tcatctgcca ctggttattt ttttctaagg agtaacttgc aagttttcag   3300
tacaaatctg tgctacactg gataaaaatc taatttatga attttacttg caccttatag   3360
ttcatagcaa ttaactgatt tgtagtgatt cattgtttgt tttatatacc aatgacttcc   3420
atattttaaa agagaaaaac aactttatgt tgcaggaaac ccttttttgta agtctttatt   3480
atttactttg cattttgttt cactctttcc agataagcag agttgctctt caccagtgtt   3540
tttcttcatg tgcaaagtga ctatttgttc tataatactt ttatgtgtgt tatatcaaat   3600
gtgtcttaag cttcatgcaa actcagtcat cagttcgtgt tgtctgaagc aagtgggaga   3660
tatataaata cccagtagct aaaatggtca gtctttttta gatgttttcc tacttagtat   3720
ctcctaataa cgttttgctg tgtcactaga tgttcatttc acaagtgcat gtctttctaa   3780
taatccacac atttcatgct ctaataatcc acacatttca tgctcatttt tattgttttt   3840
acagccagtt atagtaagaa aaaggttttt ccccttgtgc tgctttataa tttagcgtgt   3900
gtctgaacct tatccatgtt tgctagatga ggtcttgtca aatatatcac taccattgtc   3960
accggtgaaa agaaacaggt agttaagtta gggttaacat tcatttcaac cacgaggttg   4020
tatatcatga ctagctttta ctcttggttt acagagaaaa gttaaacagc caactaggca   4080
gtttttaaga atattaacaa tatattaaca aacaccaata caactaatcc tatttggttt   4140
taatgatttc accatgggat taagaactat atcaggaaca tccctgagaa acggttttaa   4200
gtgtagcaac tactcttcct taatggacag ccacataacg tgtaggaagt cctttatcac   4260
ttatcctcga tccataagca tatcttgcag aggggaacta cttctttaaa cacatggagg   4320
gaaagaagat gatgccactg gcaccagagg gttagtactg tgatgcatcc taaaatattt   4380
attatattgg taaaaattct ggttaaataa aaaattagag atcactcttg gctgatttca   4440
gcaccaggaa ctgtattaca gttttagaga ttaattccta gtgtttacct gattatagca   4500
gttggcatca tggggcattt aattctgact ttatccccac gtcagcctta ataaagtctt   4560
ctttaccttc tctatgaaga ctttaaagcc caaataatca tttttcacat tgatattcaa   4620
gaattgagat agatagaagc caaagtgggt atctgacaag tggaaaatca aacgtttaag   4680
aagaattaca actctgaaaa gcatttatat gtggaacttc tcaaggagcc tcctggggac   4740
tggaaagtaa gtcatcagcc aggcaaatga ctcatgctga agagagtccc catttcagtc   4800
ccctgagatc tagctgatgc ttagatcctt tgaaataaaa attatgtctt tataactctg   4860
atcttttaca taaagcagaa gaggaatcaa ctagttaatt gcaaggtttc tactctgttt   4920
cctctgtaaa gatcagatgg taatctttca aataagaaaa aaataaagac gtatgtttga   4980
ccaagtagtt tcacaagaat atttgggaac ttgtttcttt taattttatt tgtccctgag   5040
```

```
tgaagtctag aaagaaaggt aaagagtcta gagtttattc ctctttccaa aacattctca   5100
ttcctctcct ccctacactt agtatttccc ccacagagtg cctagaatct taataatgaa   5160
taaaataaaa agcagcaata tgtcattaac aaatccagac ctgaaagggt aaagggttta   5220
taactgcact aataaagaga ggctcttttt ttttcttcca gtttgttggt ttttaatggt   5280
accgtgttgt aaagataccc actaatggac aatcaaattg cagaaaaggc tcaatatcca   5340
agagacaggg actaatgcac tgtacaatct gcttatcctt gcccttctct cttgccaaag   5400
tgtgcttcag aaatatatac tgctttaaaa aagaataaaa gaatatcctt ttacaagtgg   5460
ctttacattt cctaaaatgc cataagaaaa tgcaatatct gggtactgta tggggaaaaa   5520
aatgtccaag tttgtgtaaa accagtgcat ttcagcttgc aagttactga acacaataat   5580
gctgttttaa ttttgtttta tatcagttaa aattcacaat aatgtagata gaacaaatta   5640
cagacaagga aagaaaaaac ttgaatgaaa tggattttac agaaagcttt atgataattt   5700
ttgaatgcat tatttatttt ttgtgccatg catttttttt ctcaccaaat gaccttacct   5760
gtaatacagt cttgtttgtc tgtttacaac catgtattta ttgcaatgta catactgtaa   5820
tgttaattgt aaattatctg ttcttattaa aacatcatcc catgatggga tggtgttgat   5880
atatttggaa actcttggtg agagaatgaa tggtgtgtat acatactctg tacatttttc   5940
ttttctcctg taatatagtc ttgtcacctt agagcttgtt tatggaagat tcaagaaaac   6000
tataaaatac ttaaagatat ataaatttaa aaaaacatag ctgcaggtct ttggtcccag   6060
ggctgtgcct taactttaac caatattttc ttctgttttg ctgcatttga aaggtaacag   6120
tggagctagg gctgggcatt ttacatccag gcttttaatt gattagaatt ctgccaatag   6180
gtggatttta caaaaccaca gacaacctct gaaagattct gagacccttt tgagacagaa   6240
gctcttaagt acttcttgcc agggagcagc actgcatgtg tgatggttgt ttgccatctg   6300
ttgatcagga actacttcag ctacttgcat ttgattattt cctttttttt tttttttaac   6360
tcggaaacac aactggggaa atatattctt tcccagtgat tataaacaat ctttttcttt   6420
tttttaagtc cttttggctt ctagagctca taggaaaatg gacttgattt gaaattggag   6480
ccagagttta ctcgtgttgg ttatctattc atcagcttcc tgacatgtta agagaataca   6540
ttaaagagaa aatactgttt tttaatccta aaatttttct tccactaaga taaaccaaat   6600
gtccttacat atatgtaaac ccatctattt aaacgcaaag gtgggttgat gtcagtttac   6660
atagcagaaa gcattcacta tcctctaaga tttgtttctg caaaactttc attgctttag   6720
aattttaaaa tttcaccttg tacaatggcc agcccctaaa gcaggaaaca tttataatgg   6780
attatatgga aacatcctcc cagtacttgc ccagcccttg aatcatgtgg cttttcagtg   6840
aaaggaaaga ttctttttct aggaaaaatg agcctatttt attttatttt attttatttt   6900
ttgacacaaa ctgtagattt tagcagccct ggcccaaagg aatttgatta cttttgtttt   6960
aaacagtaca aaggggacac tataattaca aaaacatcct taactgattt gagttgtttt   7020
tatttctttg gatatatttt cagagtggta aattgtgtgt gagaattaca aatgattatt   7080
cttttagtgg tttcttagcc tctcttacag ccccacgggga tagtactgta catcaatacc  7140
ttcatatgaa atttttatat gcaatgaaaa taaaagcatg ggttgattct gcctatttat   7200
gactcaatct tttacaaata aaagattatt cattttaaat tatagttcaa tcagcatgtc   7260
tcttaggata ctgaacgtgg ttgaaatgaa aggatagtga catcataagt tagtactgat   7320
attcataacc aaataaagcc aacttgagta attttgctac attaaaaatt accaaaatta   7380
```

-continued

```
cttagatggc ctataagatt aagcatggtg ttttctaagc aagctttgaa aggggccttc   7440

catacttact taattgaata ttctgggata ttgaaaatta ttcagatact tgacaattat   7500

ttttggttac ctactccgca aactacaaag ttttaaggac tcaacaataa gttaatgaga   7560

cacagtgttt gctttcatgg agcttacagt ctggagggga caaaggctta aacaatactc   7620

atataattat atatgtgatc agtacaatga aggagctcag tggggtaaat aagcaggaac   7680

ctgaacttga tctgttccgg agggccacag aaggcttcct tgaggccttg agaaagtgat   7740

ttgcatctga gttctgaagg attgtaagag gtaactaggg aaaaagttga caggaagagg   7800

aaggggatcc agacaagaaa catttgcaaa gatcttgagg cataaatgag cttgagacat   7860

ctggagaaac tgaggaaaag tgagagagta ggcagggcct ggagccgcag agccattgct   7920

aaccatcctg tgtgagatat cccccattct gtagctttat tctcataacc ctgctcaatt   7980

ttctttataa cacttctcac agatttatat acgtgtttgt ttttgttatc tgtctctccc   8040

accagaccac agctccatga gagcaaggtc tttgcttacc aatatatcac tagcacttaa   8100

aactatgcct ggtacacagt aggttcttaa tatgtgttga atatagccat caaattgata   8160

ttggatataa ttcaatctga taagatattt tgagatatta aagagttttt aacttgatac   8220

cataaaaaaa aaaaaaaaaa                                                8240
```

<210> SEQ ID NO 11
<211> LENGTH: 809
<212> TYPE: PRT
<213> ORGANISM: Homo sapiens

<400> SEQUENCE: 11

```
Met Glu Ala Glu Gly Ser Ser Ala Pro Ala Arg Ala Gly Ser Gly Glu
1               5                   10                  15

Gly Ser Asp Ser Ala Gly Gly Ala Thr Leu Lys Ala Pro Lys His Leu
            20                  25                  30

Trp Arg His Glu Gln His His Gln Tyr Pro Leu Arg Gln Pro Gln Phe
        35                  40                  45

Arg Leu Leu His Pro His His His Leu Pro Pro Pro Pro Pro Pro Ser
    50                  55                  60

Pro Gln Pro Gln Pro Gln Cys Pro Leu Gln Pro Pro Pro Pro Pro Pro
65                  70                  75                  80

Leu Pro Pro Pro Pro Pro Pro Pro Gly Ala Ala Arg Gly Arg Tyr Ala
                85                  90                  95

Ser Ser Gly Ala Thr Gly Arg Val Arg His Arg Gly Tyr Ser Asp Thr
            100                 105                 110

Glu Arg Tyr Leu Tyr Cys Arg Ala Met Asp Arg Thr Ser Tyr Ala Val
        115                 120                 125

Glu Thr Gly His Arg Pro Gly Leu Lys Lys Ser Arg Met Ser Trp Pro
    130                 135                 140

Ser Ser Phe Gln Gly Leu Arg Arg Phe Asp Val Asp Asn Gly Thr Ser
145                 150                 155                 160

Ala Gly Arg Ser Pro Leu Asp Pro Met Thr Ser Pro Gly Ser Gly Leu
                165                 170                 175

Ile Leu Gln Ala Asn Phe Val His Ser Gln Arg Arg Glu Ser Phe Leu
            180                 185                 190

Tyr Arg Ser Asp Ser Asp Tyr Asp Leu Ser Pro Lys Ser Met Ser Arg
        195                 200                 205

Asn Ser Ser Ile Ala Ser Asp Ile His Gly Asp Asp Leu Ile Val Thr
    210                 215                 220
```

```
Pro Phe Ala Gln Val Leu Ala Ser Leu Arg Thr Val Arg Asn Asn Phe
225                 230                 235                 240

Ala Ala Leu Thr Asn Leu Gln Asp Arg Ala Pro Ser Lys Arg Ser Pro
                245                 250                 255

Met Cys Asn Gln Pro Ser Ile Asn Lys Ala Thr Ile Thr Glu Glu Ala
            260                 265                 270

Tyr Gln Lys Leu Ala Ser Glu Thr Leu Glu Glu Leu Asp Trp Cys Leu
        275                 280                 285

Asp Gln Leu Glu Thr Leu Gln Thr Arg His Ser Val Ser Glu Met Ala
    290                 295                 300

Ser Asn Lys Phe Lys Arg Met Leu Asn Arg Glu Leu Thr His Leu Ser
305                 310                 315                 320

Glu Met Ser Arg Ser Gly Asn Gln Val Ser Glu Phe Ile Ser Asn Thr
                325                 330                 335

Phe Leu Asp Lys Gln His Glu Val Glu Ile Pro Ser Pro Thr Gln Lys
            340                 345                 350

Glu Lys Glu Lys Lys Lys Arg Pro Met Ser Gln Ile Ser Gly Val Lys
        355                 360                 365

Lys Leu Met His Ser Ser Ser Leu Thr Asn Ser Ser Ile Pro Arg Phe
    370                 375                 380

Gly Val Lys Thr Glu Gln Glu Asp Val Leu Ala Lys Glu Leu Glu Asp
385                 390                 395                 400

Val Asn Lys Trp Gly Leu His Val Phe Arg Ile Ala Glu Leu Ser Gly
                405                 410                 415

Asn Arg Pro Leu Thr Val Ile Met His Thr Ile Phe Gln Glu Arg Asp
            420                 425                 430

Leu Leu Lys Thr Phe Lys Ile Pro Val Asp Thr Leu Ile Thr Tyr Leu
        435                 440                 445

Met Thr Leu Glu Asp His Tyr His Ala Asp Val Ala Tyr His Asn Asn
    450                 455                 460

Ile His Ala Ala Asp Val Val Gln Ser Thr His Val Leu Leu Ser Thr
465                 470                 475                 480

Pro Ala Leu Glu Ala Val Phe Thr Asp Leu Glu Ile Leu Ala Ala Ile
                485                 490                 495

Phe Ala Ser Ala Ile His Asp Val Asp His Pro Gly Val Ser Asn Gln
            500                 505                 510

Phe Leu Ile Asn Thr Asn Ser Glu Leu Ala Leu Met Tyr Asn Asp Ser
        515                 520                 525

Ser Val Leu Glu Asn His His Leu Ala Val Gly Phe Lys Leu Leu Gln
    530                 535                 540

Glu Glu Asn Cys Asp Ile Phe Gln Asn Leu Thr Lys Lys Gln Arg Gln
545                 550                 555                 560

Ser Leu Arg Lys Met Val Ile Asp Ile Val Leu Ala Thr Asp Met Ser
                565                 570                 575

Lys His Met Asn Leu Leu Ala Asp Leu Lys Thr Met Val Glu Thr Lys
            580                 585                 590

Lys Val Thr Ser Ser Gly Val Leu Leu Leu Asp Asn Tyr Ser Asp Arg
        595                 600                 605

Ile Gln Val Leu Gln Asn Met Val His Cys Ala Asp Leu Ser Asn Pro
    610                 615                 620

Thr Lys Pro Leu Gln Leu Tyr Arg Gln Trp Thr Asp Arg Ile Met Glu
625                 630                 635                 640
```

-continued

```
Glu Phe Phe Arg Gln Gly Asp Arg Glu Arg Glu Arg Gly Met Glu Ile
                645                 650                 655

Ser Pro Met Cys Asp Lys His Asn Ala Ser Val Glu Lys Ser Gln Val
            660                 665                 670

Gly Phe Ile Asp Tyr Ile Val His Pro Leu Trp Glu Thr Trp Ala Asp
        675                 680                 685

Leu Val His Pro Asp Ala Gln Asp Ile Leu Asp Thr Leu Glu Asp Asn
    690                 695                 700

Arg Glu Trp Tyr Gln Ser Thr Ile Pro Gln Ser Pro Ser Pro Ala Pro
705                 710                 715                 720

Asp Asp Pro Glu Glu Gly Arg Gln Gly Gln Thr Glu Lys Phe Gln Phe
                725                 730                 735

Glu Leu Thr Leu Glu Glu Asp Gly Glu Ser Asp Thr Glu Lys Asp Ser
            740                 745                 750

Gly Ser Gln Val Glu Glu Asp Thr Ser Cys Ser Asp Ser Lys Thr Leu
        755                 760                 765

Cys Thr Gln Asp Ser Glu Ser Thr Glu Ile Pro Leu Asp Glu Gln Val
    770                 775                 780

Glu Glu Glu Ala Val Gly Glu Glu Glu Glu Ser Gln Pro Glu Ala Cys
785                 790                 795                 800

Val Ile Asp Asp Arg Ser Pro Asp Thr
                805
```

<210> SEQ ID NO 12
<211> LENGTH: 7979
<212> TYPE: DNA
<213> ORGANISM: Homo sapiens

<400> SEQUENCE: 12

```
cagcagcagg ctcagacctg cttccctgga catttccggg accgtgagcg agggaaccac     60

gttgccctgg attcttgcca gctgtacaaa gttgaccagg aaaatggctc agcagacaag    120

cccggacact ttaacagtac ctgaagtgga taatccgcat tgtccaaacc cgtggctgaa    180

cgaagacctt gtgaaatcct tgcgagaaaa cctgttgcag catgagaagt ccaagacagc    240

gaggaaatcg gtttctccca agctctctcc agtgatctct ccgagaaatt cccccaggct    300

tctgcgcaga atgcttctca gcagcaacat ccccaaacag cggcgtttca cggtggcaca    360

tacatgtttt gatgtggaca atggcacatc tgcgggacgg agtcccttgg atcccatgac    420

cagcccagga tccgggctaa ttctccaagc aaattttgtc cacagtcaac gacgggagtc    480

cttcctgtat cgatccgaca gcgattatga cctctctcca aagtctatgt cccggaactc    540

ctccattgcc agtgatatac acggagatga cttgattgtg actccatttg ctcaggtctt    600

ggccagtctg cgaactgtac gaaacaactt tgctgcatta actaatttgc aagatcgagc    660

acctagcaaa agatcaccca tgtgcaacca accatccatc aacaaagcca ccataacaga    720

ggaggcctac cagaaactgg ccagcgagac cctggaggag ctggactggt gtctggacca    780

gctagagacc ctacagacca ggcactccgt cagtgagatg gcctccaaca agtttaaaag    840

gatgcttaat cgggagctca cccatctctc tgaaatgagt cggtctggaa atcaagtgtc    900

agagtttata tcaaacacat tcttagataa gcaacatgaa gtggaaattc cttctccaac    960

tcagaaggaa aaggagaaaa agaaaagacc aatgtctcag atcagtggag tcaagaaatt   1020

gatgcacagc tctagtctga ctaattcaag tatcccaagg tttggagtta aaactgaaca   1080

agaagatgtc cttgccaagg aactagaaga tgtgaacaaa tggggtcttc atgttttcag   1140
```

-continued

```
aatagcagag ttgtctggta accggccctt gactgttatc atgcacacca tttttcagga   1200
acgggattta ttaaaaacat ttaaaattcc agtagatact ttaattacat atcttatgac   1260
tctcgaagac cattaccatg ctgatgtggc ctatcacaac aatatccatg ctgcagatgt   1320
tgtccagtct actcatgtgc tattatctac acctgctttg gaggctgtgt ttacagattt   1380
ggagattctt gcagcaattt ttgccagtgc aatacatgat gtagatcatc ctggtgtgtc   1440
caatcaattt ctgatcaata caaactctga acttgccttg atgtacaatg attcctcagt   1500
cttagagaac catcatttgg ctgtgggctt taaattgctt caggaagaaa actgtgacat   1560
tttccagaat ttgaccaaaa aacaaagaca atctttaagg aaaatggtca ttgacatcgt   1620
acttgcaaca gatatgtcaa aacacatgaa tctactggct gatttgaaga ctatggttga   1680
aactaagaaa gtgacaagct ctggagttct tcttcttgat aattattccg ataggattca   1740
ggttcttcag aatatggtgc actgtgcaga tctgagcaac ccaacaaagc ctctccagct   1800
gtaccgccag tggacggacc ggataatgga ggagttcttc cgccaaggag accgagagag   1860
ggaacgtggc atggagataa gccccatgtg tgacaagcac aatgcttccg tggaaaaatc   1920
acaggtgggc ttcatagact atattgttca tcccctctgg gagacatggg cagacctcgt   1980
ccaccctgac gcccaggata ttttggacac tttggaggac aatcgtgaat ggtaccagag   2040
cacaatccct cagagcccct ctcctgcacc tgatgaccca gaggagggcc ggcagggtca   2100
aactgagaaa ttccagtttg aactaacttt agaggaagat ggtgagtcag acacggaaaa   2160
ggacagtggc agtcaagtgg aagaagacac tagctgcagt gactccaaga ctctttgtac   2220
tcaagactca gagtctactg aaattcccct tgatgaacag gttgaagagg aggcagtagg   2280
ggaagaagag gaaagccagc ctgaagcctg tgtcatagat gatcgttctc ctgacacgta   2340
acagtgcaaa aactttcatg cctttttttt ttttaagtag aaaaattgtt tccaaagtgc   2400
atgtcacatg ccacaaccac ggtcacacct cactgtcatc tgccaggacg tttgttgaac   2460
aaaactgacc ttgactactc agtccagcgc tcaggaatat cgtaaccagt tttttcacct   2520
ccatgtcatc cgagcaaggt ggacatcttc acgaacagcg tttttaacaa gatttcagct   2580
tggtagagct gacaaagcag ataaaatcta ctccaaatta ttttcaagag agtgtgactc   2640
atcaggcagc ccaaaagttt attggacttg ggtttctat tcctttttat ttgtttgcaa   2700
tattttcaga agaaaggcat tgcacagagt gaacttaatg gacgaagcaa caaatatgtc   2760
aagaacagga catagcacga atctgttacc agtaggagga ggatgagcca cagaaattgc   2820
ataattttct aatttcaagt cttcctgata catgactgaa tagtgtggtt cagtgagctg   2880
cactgacctc tacattttgt atgatatgta aaacagattt tttgtagagc ttacttttat   2940
tattaaatgt attgaggtat tatatttaaa aaaaactatg ttcagaactt catctgccac   3000
tggttatttt tttctaagga gtaacttgca agttttcagt acaaatctgt gctacactgg   3060
ataaaaatct aatttatgaa ttttacttgc accttatagt tcatagcaat taactgattt   3120
gtagtgattc attgtttgtt ttatatacca atgacttcca tattttaaaa gagaaaaaca   3180
actttatgtt gcaggaaacc ctttttgtaa gtctttatta tttactttgc attttgtttc   3240
actctttcca gataagcaga gttgctcttc accagtgttt ttcttcatgt gcaaagtgac   3300
tatttgttct ataatacttt tatgtgtgtt atatcaaatg tgtcttaagc ttcatgcaaa   3360
ctcagtcatc agttcgtgtt gtctgaagca agtgggagat atataaatac ccagtagcta   3420
aaatggtcag tctttttttag atgttttcct acttagtatc tcctaataac gttttgctgt   3480
gtcactagat gttcatttca caagtgcatg tctttctaat aatccacaca tttcatgctc   3540
```

-continued

```
taataatcca cacatttcat gctcattttt attgttttta cagccagtta tagtaagaaa   3600
aaggtttttc cccttgtgct gctttataat ttagcgtgtg tctgaacctt atccatgttt   3660
gctagatgag gtcttgtcaa atatatcact accattgtca ccggtgaaaa gaaacaggta   3720
gttaagttag ggttaacatt catttcaacc acgaggttgt atatcatgac tagcttttac   3780
tcttggttta cagagaaaag ttaaacagcc aactaggcag tttttaagaa tattaacaat   3840
atattaacaa acaccaatac aactaatcct atttggtttt aatgatttca ccatgggatt   3900
aagaactata tcaggaacat ccctgagaaa cggttttaag tgtagcaact actcttcctt   3960
aatggacagc cacataacgt gtaggaagtc ctttatcact tatcctcgat ccataagcat   4020
atcttgcaga ggggaactac ttctttaaac acatggaggg aaagaagatg atgccactgg   4080
caccagaggg ttagtactgt gatgcatcct aaaatattta ttatattggt aaaaattctg   4140
gttaaataaa aaattagaga tcactcttgg ctgatttcag caccaggaac tgtattacag   4200
ttttagagat taattcctag tgtttacctg attatagcag ttggcatcat ggggcattta   4260
attctgactt tatccccacg tcagccttaa taaagtcttc tttaccttct ctatgaagac   4320
tttaaagccc aaataatcat ttttcacatt gatattcaag aattgagata gatagaagcc   4380
aaagtgggta tctgacaagt ggaaaatcaa acgtttaaga agaattacaa ctctgaaaag   4440
catttatatg tggaacttct caaggagcct cctggggact ggaaagtaag tcatcagcca   4500
ggcaaatgac tcatgctgaa gagagtcccc atttcagtcc cctgagatct agctgatgct   4560
tagatccttt gaaataaaaa ttatgtcttt ataactctga tcttttacat aaagcagaag   4620
aggaatcaac tagttaattg caaggtttct actctgtttc ctctgtaaag atcagatggt   4680
aatctttcaa ataagaaaaa aataaagacg tatgtttgac caagtagttt cacaagaata   4740
tttgggaact tgtttctttt aattttattt gtccctgagt gaagtctaga aagaaaggta   4800
aagagtctag agtttattcc tctttccaaa acattctcat tcctctcctc cctacactta   4860
gtatttcccc cacagagtgc ctagaatctt aataatgaat aaaataaaaa gcagcaatat   4920
gtcattaaca aatccagacc tgaaagggta aagggtttat aactgcacta ataaagagag   4980
gctctttttt tttcttccag tttgttggtt tttaatggta ccgtgttgta aagataccca   5040
ctaatggaca atcaaattgc agaaaaggct caatatccaa gagacaggga ctaatgcact   5100
gtacaatctg cttatccttg cccttctctc ttgccaaagt gtgcttcaga aatatatact   5160
gctttaaaaa agaataaaag aatatccttt tacaagtggc tttacatttc ctaaaatgcc   5220
ataagaaaat gcaatatctg ggtactgtat ggggaaaaaa atgtccaagt ttgtgtaaaa   5280
ccagtgcatt tcagcttgca agttactgaa cacaataatg ctgttttaat tttgttttat   5340
atcagttaaa attcacaata atgtagatag aacaaattac agacaaggaa agaaaaaact   5400
tgaatgaaat ggattttaca gaaagcttta tgataatttt tgaatgcatt atttattttt   5460
tgtgccatgc atttttttc tcaccaaatg accttacctg taatacagtc ttgtttgtct   5520
gtttacaacc atgtatttat tgcaatgtac atactgtaat gttaattgta aattatctgt   5580
tcttattaaa acatcatccc atgatgggat ggtgttgata tatttggaaa ctcttggtga   5640
gagaatgaat ggtgtgtata catactctgt acatttttct tttctcctgt aatatagtct   5700
tgtcacctta gagcttgttt atggaagatt caagaaaact ataaaatact taaagatata   5760
taaatttaaa aaaacatagc tgcaggtctt tggtcccagg gctgtgcctt aactttaacc   5820
aatattttct tctgttttgc tgcatttgaa aggtaacagt ggagctaggg ctgggcattt   5880
```

-continued

```
tacatccagg cttttaattg attagaattc tgccaatagg tggattttac aaaaccacag   5940
acaacctctg aaagattctg agaccctttt gagacagaag ctcttaagta cttcttgcca   6000
gggagcagca ctgcatgtgt gatggttgtt tgccatctgt tgatcaggaa ctacttcagc   6060
tacttgcatt tgattatttc cttttttttt ttttttaact cggaaacaca actggggaaa   6120
tatattcttt cccagtgatt ataaacaatc tttttctttt ttttaagtcc ttttggcttc   6180
tagagctcat aggaaaatgg acttgatttg aaattggagc cagagtttac tcgtgttggt   6240
tatctattca tcagcttcct gacatgttaa gagaatacat taaagagaaa atactgtttt   6300
ttaatcctaa aatttttctt ccactaagat aaaccaaatg tccttacata tatgtaaacc   6360
catctattta aacgcaaagg tgggttgatg tcagtttaca tagcagaaag cattcactat   6420
cctctaagat ttgtttctgc aaaactttca ttgctttaga attttaaaat ttcaccttgt   6480
acaatggcca gcccctaaag caggaaacat ttataatgga ttatatggaa acatcctccc   6540
agtacttgcc cagcccttga atcatgtggc ttttcagtga aaggaaagat tctttttcta   6600
ggaaaaatga gcctatttta ttttatttta ttttattttt tgacacaaac tgtagatttt   6660
agcagccctg gcccaaagga atttgattac ttttgtttta aacagtacaa aggggacact   6720
ataattacaa aaacatcctt aactgatttg agttgttttt atttctttgg atatattttc   6780
agagtggtaa attgtgtgtg agaattacaa atgattattc ttttagtggt ttcttagcct   6840
ctcttacagc ccacggggat agtactgtac atcaatacct tcatatgaaa tttttatatg   6900
caatgaaaat aaaagcatgg gttgattctg cctatttatg actcaatctt ttacaaataa   6960
aagattattc attttaaatt atagttcaat cagcatgtct cttaggatac tgaacgtggt   7020
tgaaatgaaa ggatagtgac atcataagtt agtactgata ttcataacca aataaagcca   7080
acttgagtaa ttttgctaca ttaaaaatta ccaaaattac ttagatggcc tataagatta   7140
agcatggtgt tttctaagca agctttgaaa ggggccttcc atacttactt aattgaatat   7200
tctgggatat tgaaaattat tcagatactt gacaattatt tttggttacc tactccgcaa   7260
actacaaagt tttaaggact caacaataag ttaatgagac acagtgtttg ctttcatgga   7320
gcttacagtc tggaggggac aaaggcttaa acaatactca tataattata tatgtgatca   7380
gtacaatgaa ggagctcagt ggggtaaata agcaggaacc tgaacttgat ctgttccgga   7440
gggccacaga aggcttcctt gaggccttga gaaagtgatt tgcatctgag ttctgaagga   7500
ttgtaagagg taactaggga aaaagttgac aggaagagga aggggatcca gacaagaaac   7560
atttgcaaag atcttgaggc ataaatgagc ttgagacatc tggagaaact gaggaaaagt   7620
gagagagtag gcagggcctg gagccgcaga gccattgcta accatcctgt gtgagatatc   7680
ccccattctg tagctttatt ctcataaccc tgctcaattt tctttataac acttctcaca   7740
gatttatata cgtgtttgtt tttgttatct gtctctccca ccagaccaca gctccatgag   7800
agcaaggtct ttgcttacca atatatcact agcacttaaa actatgcctg gtacacagta   7860
ggttcttaat atgtgttgaa tatagccatc aaattgatat tggatataat tcaatctgat   7920
aagatatttt gagatattaa agagttttta acttgatacc ataaaaaaaa aaaaaaaaa    7979
```

<210> SEQ ID NO 13
<211> LENGTH: 745
<212> TYPE: PRT
<213> ORGANISM: Homo sapiens

<400> SEQUENCE: 13

Met Ala Gln Gln Thr Ser Pro Asp Thr Leu Thr Val Pro Glu Val Asp

-continued

```
1               5                   10                  15

Asn Pro His Cys Pro Asn Pro Trp Leu Asn Glu Asp Leu Val Lys Ser
            20                  25                  30

Leu Arg Glu Asn Leu Leu Gln His Glu Lys Ser Lys Thr Ala Arg Lys
        35                  40                  45

Ser Val Ser Pro Lys Leu Ser Pro Val Ile Ser Pro Arg Asn Ser Pro
    50                  55                  60

Arg Leu Leu Arg Arg Met Leu Leu Ser Ser Asn Ile Pro Lys Gln Arg
65                  70                  75                  80

Arg Phe Thr Val Ala His Thr Cys Phe Asp Val Asp Asn Gly Thr Ser
                85                  90                  95

Ala Gly Arg Ser Pro Leu Asp Pro Met Thr Ser Pro Gly Ser Gly Leu
            100                 105                 110

Ile Leu Gln Ala Asn Phe Val His Ser Gln Arg Arg Glu Ser Phe Leu
        115                 120                 125

Tyr Arg Ser Asp Ser Asp Tyr Asp Leu Ser Pro Lys Ser Met Ser Arg
    130                 135                 140

Asn Ser Ser Ile Ala Ser Asp Ile His Gly Asp Asp Leu Ile Val Thr
145                 150                 155                 160

Pro Phe Ala Gln Val Leu Ala Ser Leu Arg Thr Val Arg Asn Asn Phe
                165                 170                 175

Ala Ala Leu Thr Asn Leu Gln Asp Arg Ala Pro Ser Lys Arg Ser Pro
            180                 185                 190

Met Cys Asn Gln Pro Ser Ile Asn Lys Ala Thr Ile Thr Glu Glu Ala
        195                 200                 205

Tyr Gln Lys Leu Ala Ser Glu Thr Leu Glu Glu Leu Asp Trp Cys Leu
    210                 215                 220

Asp Gln Leu Glu Thr Leu Gln Thr Arg His Ser Val Ser Glu Met Ala
225                 230                 235                 240

Ser Asn Lys Phe Lys Arg Met Leu Asn Arg Glu Leu Thr His Leu Ser
                245                 250                 255

Glu Met Ser Arg Ser Gly Asn Gln Val Ser Glu Phe Ile Ser Asn Thr
            260                 265                 270

Phe Leu Asp Lys Gln His Glu Val Glu Ile Pro Ser Pro Thr Gln Lys
        275                 280                 285

Glu Lys Glu Lys Lys Lys Arg Pro Met Ser Gln Ile Ser Gly Val Lys
    290                 295                 300

Lys Leu Met His Ser Ser Ser Leu Thr Asn Ser Ser Ile Pro Arg Phe
305                 310                 315                 320

Gly Val Lys Thr Glu Gln Glu Asp Val Leu Ala Lys Glu Leu Glu Asp
                325                 330                 335

Val Asn Lys Trp Gly Leu His Val Phe Arg Ile Ala Glu Leu Ser Gly
            340                 345                 350

Asn Arg Pro Leu Thr Val Ile Met His Thr Ile Phe Gln Glu Arg Asp
        355                 360                 365

Leu Leu Lys Thr Phe Lys Ile Pro Val Asp Thr Leu Ile Thr Tyr Leu
    370                 375                 380

Met Thr Leu Glu Asp His Tyr His Ala Asp Val Ala Tyr His Asn Asn
385                 390                 395                 400

Ile His Ala Ala Asp Val Val Gln Ser Thr His Val Leu Leu Ser Thr
                405                 410                 415

Pro Ala Leu Glu Ala Val Phe Thr Asp Leu Glu Ile Leu Ala Ala Ile
            420                 425                 430
```

```
Phe Ala Ser Ala Ile His Asp Val Asp His Pro Gly Val Ser Asn Gln
        435                 440                 445

Phe Leu Ile Asn Thr Asn Ser Glu Leu Ala Leu Met Tyr Asn Asp Ser
    450                 455                 460

Ser Val Leu Glu Asn His His Leu Ala Val Gly Phe Lys Leu Leu Gln
465                 470                 475                 480

Glu Glu Asn Cys Asp Ile Phe Gln Asn Leu Thr Lys Lys Gln Arg Gln
                485                 490                 495

Ser Leu Arg Lys Met Val Ile Asp Ile Val Leu Ala Thr Asp Met Ser
            500                 505                 510

Lys His Met Asn Leu Leu Ala Asp Leu Lys Thr Met Val Glu Thr Lys
        515                 520                 525

Lys Val Thr Ser Ser Gly Val Leu Leu Leu Asp Asn Tyr Ser Asp Arg
    530                 535                 540

Ile Gln Val Leu Gln Asn Met Val His Cys Ala Asp Leu Ser Asn Pro
545                 550                 555                 560

Thr Lys Pro Leu Gln Leu Tyr Arg Gln Trp Thr Asp Arg Ile Met Glu
                565                 570                 575

Glu Phe Phe Arg Gln Gly Asp Arg Glu Arg Glu Arg Gly Met Glu Ile
            580                 585                 590

Ser Pro Met Cys Asp Lys His Asn Ala Ser Val Glu Lys Ser Gln Val
        595                 600                 605

Gly Phe Ile Asp Tyr Ile Val His Pro Leu Trp Glu Thr Trp Ala Asp
    610                 615                 620

Leu Val His Pro Asp Ala Gln Asp Ile Leu Asp Thr Leu Glu Asp Asn
625                 630                 635                 640

Arg Glu Trp Tyr Gln Ser Thr Ile Pro Gln Ser Pro Ser Pro Ala Pro
                645                 650                 655

Asp Asp Pro Glu Glu Gly Arg Gln Gly Gln Thr Glu Lys Phe Gln Phe
            660                 665                 670

Glu Leu Thr Leu Glu Glu Asp Gly Glu Ser Asp Thr Glu Lys Asp Ser
        675                 680                 685

Gly Ser Gln Val Glu Glu Asp Thr Ser Cys Ser Asp Ser Lys Thr Leu
    690                 695                 700

Cys Thr Gln Asp Ser Glu Ser Thr Glu Ile Pro Leu Asp Glu Gln Val
705                 710                 715                 720

Glu Glu Glu Ala Val Gly Glu Glu Glu Glu Ser Gln Pro Glu Ala Cys
                725                 730                 735

Val Ile Asp Asp Arg Ser Pro Asp Thr
            740                 745
```

<210> SEQ ID NO 14
<211> LENGTH: 19
<212> TYPE: DNA
<213> ORGANISM: Artificial Sequence
<220> FEATURE:
<223> OTHER INFORMATION: PDE4D5_forward primer

<400> SEQUENCE: 14
gcttctcagc agcaacatc 19

<210> SEQ ID NO 15
<211> LENGTH: 20
<212> TYPE: DNA
<213> ORGANISM: Artificial Sequence
<220> FEATURE:

-continued

<223> OTHER INFORMATION: PDE4D5_reverse primer

<400> SEQUENCE: 15
tgccattgtc cacatcaaaa 20

<210> SEQ ID NO 16
<211> LENGTH: 24
<212> TYPE: DNA
<213> ORGANISM: Artificial Sequence
<220> FEATURE:
<223> OTHER INFORMATION: PDE4D5 probe

<400> SEQUENCE: 16
acagcggcgt ttcacggtgg caca 24

<210> SEQ ID NO 17
<211> LENGTH: 7591
<212> TYPE: DNA
<213> ORGANISM: Homo sapiens

<400> SEQUENCE: 17
agttccttat ttggtagctt ttgacaggac tagcctttct tgcaactaag catcttgaca 60
tacattattc attaagccct ggagctcggg agagaaagat gcagaccctt agatctttag 120
atattccttt atcacgtgga ttttctttat tcagaatagt tgctgaattt tgtgccattc 180
tggagtctta caaatggcat gtattcgatg ggaagacggc tggatgggat ttaatgcgag 240
gctttcttat gtatacttaa ttaccaaaaa tctttaaaaa ctcatactct gcgtggcttg 300
tggaggttgt taaagtgtcg agattttgaa gctaaataca ttttagagct tactatatat 360
atacatatat atatatatac atataatcaa tcaaaaatgc ctgaagcaaa ctatttactg 420
tcagtgtctt ggggctacat aaagtttaaa aggatgctta atcgggagct cacccatctc 480
tctgaaatga gtcggtctgg aaatcaagtg tcagagttta tatcaaacac attcttagat 540
aagcaacatg aagtggaaat tccttctcca actcagaagg aaaaggagaa aaagaaaaga 600
ccaatgtctc agatcagtgg agtcaagaaa ttgatgcaca gctctagtct gactaattca 660
agtatcccaa ggtttggagt taaaactgaa caagaagatg tccttgccaa ggaactagaa 720
gatgtgaaca aatggggtct tcatgttttc agaatagcag agttgtctgg taaccggccc 780
ttgactgtta tcatgcacac catttttcag gaacgggatt tattaaaaac atttaaaatt 840
ccagtagata ctttaattac atatcttatg actctcgaag accattacca tgctgatgtg 900
gcctatcaca acaatatcca tgctgcagat gttgtccagt ctactcatgt gctattatct 960
acacctgctt tggaggctgt gtttacagat ttggagattc ttgcagcaat tttgccagt 1020 gcaatacatg atgtagatca tcctggtgtg tccaatcaat ttctgatcaa tacaaactct 1080
gaacttgcct tgatgtacaa tgattcctca gtcttagaga accatcattt ggctgtgggc 1140
tttaaattgc ttcaggaaga aaactgtgac attttccaga atttgaccaa aaaacaaaga 1200
caatctttaa ggaaaatggt cattgacatc gtacttgcaa cagatatgtc aaaacacatg 1260
aatctactgg ctgatttgaa gactatggtt gaaactaaga aagtgacaag ctctggagtt 1320
cttcttcttg ataattattc cgataggatt caggttcttc agaatatggt gcactgtgca 1380
gatctgagca acccaacaaa gcctctccag ctgtaccgcc agtggacgga ccggataatg 1440
gaggagttct tccgccaagg agaccgagag agggaacgtg gcatggagat aagccccatg 1500
tgtgacaagc acaatgcttc cgtggaaaaa tcacaggtgg gcttcataga ctatattgtt 1560
catcccctct gggagacatg ggcagacctc gtccaccctg acgcccagga tattttggac 1620
actttggagg acaatcgtga atggtaccag agcacaatcc ctcagagccc ctctcctgca 1680
cctgatgacc cagaggaggg ccggcagggt caaactgaga aattccagtt tgaactaact 1740
ttagaggaag atggtgagtc agacacggaa aaggacagtg gcagtcaagt ggaagaagac 1800
actagctgca gtgactccaa gactctttgt actcaagact cagagtctac tgaaattccc 1860
cttgatgaac aggttgaaga ggaggcagta ggggaagaag aggaaagcca gcctgaagcc 1920
tgtgtcatag atgatcgttc tcctgacacg taacagtgca aaaactttca tgcctttttt 1980
ttttttaagt agaaaaattg tttccaaagt gcatgtcaca tgccacaacc acggtcacac 2040
ctcactgtca tctgccagga cgtttgttga acaaaactga ccttgactac tcagtccagc 2100
gctcaggaat atcgtaacca gtttttcac ctccatgtca tccgagcaag gtggacatct 2160
tcacgaacag cgtttttaac aagatttcag cttggtagag ctgacaaagc agataaaatc 2220
tactccaaat tattttcaag agagtgtgac tcatcaggca gcccaaaagt ttattggact 2280
tggggtttct attccttttt atttgtttgc aatattttca gaagaaaggc attgcacaga 2340
gtgaacttaa tggacgaagc aacaaatatg tcaagaacag gacatagcac gaatctgtta 2400
ccagtaggag gaggatgagc cacagaaatt gcataatttt ctaatttcaa gtcttcctga 2460
tacatgactg aatagtgtgg ttcagtgagc tgcactgacc tctacatttt gtatgatatg 2520
taaaacagat tttttgtaga gcttactttt attattaaat gtattgaggt attatattta 2580
aaaaaaacta tgttcagaac ttcatctgcc actggttatt tttttctaag gagtaacttg 2640
caagttttca gtacaaatct gtgctacact ggataaaaat ctaatttatg aattttactt 2700
gcaccttata gttcatagca attaactgat ttgtagtgat tcattgtttg ttttatatac 2760
caatgacttc catattttaa aagagaaaaa caactttatg ttgcaggaaa cccttttgt 2820
aagtctttat tatttacttt gcattttgtt tcactctttc cagataagca gagttgctct 2880
tcaccagtgt ttttcttcat gtgcaaagtg actatttgtt ctataatact tttatgtgtg 2940
ttatatcaaa tgtgtcttaa gcttcatgca aactcagtca tcagttcgtg ttgtctgaag 3000
caagtgggag atatataaat acccagtagc taaaatggtc agtctttttt agatgttttc 3060
ctacttagta tctcctaata acgttttgct gtgtcactag atgttcattt cacaagtgca 3120
tgtctttcta ataatccaca catttcatgc tctaataatc cacacatttc atgctcattt 3180
ttattgtttt tacagccagt tatagtaaga aaaaggtttt tccccttgtg ctgctttata 3240
atttagcgtg tgtctgaacc ttatccatgt ttgctagatg aggtcttgtc aaatatatca 3300
ctaccattgt caccggtgaa aagaaacagg tagttaagtt agggttaaca ttcatttcaa 3360
ccacgaggtt gtatatcatg actagctttt actcttggtt tacagagaaa agttaaacag 3420
ccaactaggc agtttttaag aatattaaca atatattaac aaacaccaat acaactaatc 3480
ctatttggtt ttaatgattt caccatggga ttaagaacta tatcaggaac atccctgaga 3540
aacggtttta agtgtagcaa ctactcttcc ttaatggaca gccacataac gtgtaggaag 3600
tcctttatca cttatcctcg atccataagc atatcttgca gaggggaact acttctttaa 3660
acacatggag ggaaagaaga tgatgccact ggcaccagag ggttagtact gtgatgcatc 3720
ctaaaatatt tattatattg gtaaaaattc tggttaaata aaaaattaga gatcactctt 3780
ggctgatttc agcaccagga actgtattac agttttagag attaattcct agtgtttacc 3840
tgattatagc agttggcatc atggggcatt taattctgac tttatcccca cgtcagcctt 3900
aataaagtct tctttacctt ctctatgaag actttaaagc ccaaataatc attttcaca 3960

-continued

```
ttgatattca agaattgaga tagatagaag ccaaagtggg tatctgacaa gtggaaaatc   4020
aaacgtttaa gaagaattac aactctgaaa agcatttata tgtggaactt ctcaaggagc   4080
ctcctgggga ctggaaagta agtcatcagc caggcaaatg actcatgctg aagagagtcc   4140
ccatttcagt cccctgagat ctagctgatg cttagatcct ttgaaataaa aattatgtct   4200
ttataactct gatcttttac ataaagcaga agaggaatca actagttaat tgcaaggttt   4260
ctactctgtt tcctctgtaa agatcagatg gtaatctttc aaataagaaa aaaataaaga   4320
cgtatgtttg accaagtagt ttcacaagaa tatttgggaa cttgtttctt ttaattttat   4380
ttgtccctga gtgaagtcta gaaagaaagg taaagagtct agagtttatt cctctttcca   4440
aaacattctc attcctctcc tccctacact tagtatttcc cccacagagt gcctagaatc   4500
ttaataatga ataaaataaa aagcagcaat atgtcattaa caaatccaga cctgaaaggg   4560
taaagggttt ataactgcac taataaagag aggctctttt tttttcttcc agtttgttgg   4620
tttttaatgg taccgtgttg taaagatacc cactaatgga caatcaaatt gcagaaaagg   4680
ctcaatatcc aagagacagg gactaatgca ctgtacaatc tgcttatcct tgcccttctc   4740
tcttgccaaa gtgtgcttca gaaatatata ctgctttaaa aaagaataaa agaatatcct   4800
tttacaagtg gctttacatt tcctaaaatg ccataagaaa atgcaatatc tgggtactgt   4860
atggggaaaa aaatgtccaa gtttgtgtaa aaccagtgca tttcagcttg caagttactg   4920
aacacaataa tgctgtttta attttgtttt atatcagtta aaattcacaa taatgtagat   4980
agaacaaatt acagacaagg aaagaaaaaa cttgaatgaa atggatttta cagaaagctt   5040
tatgataatt tttgaatgca ttatttattt tttgtgccat gcattttttt tctcaccaaa   5100
tgaccttacc tgtaatacag tcttgtttgt ctgtttacaa ccatgtattt attgcaatgt   5160
acatactgta atgttaattg taaattatct gttcttatta aaacatcatc ccatgatggg   5220
atggtgttga tatatttgga aactcttggt gagagaatga atggtgtgta tacatactct   5280
gtacattttt cttttctcct gtaatatagt cttgtcacct tagagcttgt ttatggaaga   5340
ttcaagaaaa ctataaaata cttaaagata tataaattta aaaaaacata gctgcaggtc   5400
tttggtccca gggctgtgcc ttaactttaa ccaatatttt cttctgtttt gctgcatttg   5460
aaaggtaaca gtggagctag ggctgggcat tttacatcca ggcttttaat tgattagaat   5520
tctgccaata ggtggatttt acaaaaccac agacaacctc tgaaagattc tgagaccctt   5580
ttgagacaga agctcttaag tacttcttgc cagggagcag cactgcatgt gtgatggttg   5640
tttgccatct gttgatcagg aactacttca gctacttgca tttgattatt tccttttttt   5700
ttttttttaa ctcggaaaca caactgggga aatatattct ttcccagtga ttataaacaa   5760
tctttttctt ttttttaagt ccttttggct tctagagctc ataggaaaat ggacttgatt   5820
tgaaattgga gccagagttt actcgtgttg gttatctatt catcagcttc ctgacatgtt   5880
aagagaatac attaaagaga aaatactgtt ttttaatcct aaaatttttc ttccactaag   5940
ataaaccaaa tgtccttaca tatatgtaaa cccatctatt taaacgcaaa ggtgggttga   6000
tgtcagttta catagcagaa agcattcact atcctctaag atttgtttct gcaaaacttt   6060
cattgcttta gaattttaaa atttcacctt gtacaatggc cagcccctaa agcaggaaac   6120
atttataatg gattatatgg aaacatcctc ccagtacttg cccagccctt gaatcatgtg   6180
gcttttcagt gaaaggaaag attctttttc taggaaaaat gagcctattt tattttattt   6240
tattttattt tttgacacaa actgtagatt ttagcagccc tggcccaaag gaatttgatt   6300
acttttgttt taaacagtac aaaggggaca ctataattac aaaaacatcc ttaactgatt   6360
```

-continued

```
tgagttgttt ttatttcttt ggatatattt tcagagtggt aaattgtgtg tgagaattac   6420

aaatgattat tcttttagtg gtttcttagc ctctcttaca gcccacgggg atagtactgt   6480

acatcaatac cttcatatga aatttttata tgcaatgaaa ataaaagcat gggttgattc   6540

tgcctattta tgactcaatc ttttacaaat aaaagattat tcattttaaa ttatagttca   6600

atcagcatgt ctcttaggat actgaacgtg gttgaaatga aaggatagtg acatcataag   6660

ttagtactga tattcataac caaataaagc caacttgagt aattttgcta cattaaaaat   6720

taccaaaatt acttagatgg cctataagat taagcatggt gttttctaag caagctttga   6780

aaggggcctt ccatacttac ttaattgaat attctgggat attgaaaatt attcagatac   6840

ttgacaatta tttttggtta cctactccgc aaactacaaa gttttaagga ctcaacaata   6900

agttaatgag acacagtgtt tgctttcatg gagcttacag tctggagggg acaaaggctt   6960

aaacaatact catataatta tatatgtgat cagtacaatg aaggagctca gtggggtaaa   7020

taagcaggaa cctgaacttg atctgttccg gagggccaca gaaggcttcc ttgaggcctt   7080

gagaaagtga tttgcatctg agttctgaag gattgtaaga ggtaactagg gaaaaagttg   7140

acaggaagag gaaggggatc cagacaagaa acatttgcaa agatcttgag gcataaatga   7200

gcttgagaca tctggagaaa ctgaggaaaa gtgagagagt aggcagggcc tggagccgca   7260

gagccattgc taaccatcct gtgtgagata tcccccattc tgtagcttta ttctcataac   7320

cctgctcaat tttctttata acacttctca cagatttata tacgtgtttg tttttgttat   7380

ctgtctctcc caccagacca cagctccatg agagcaaggt ctttgcttac caatatatca   7440

ctagcactta aaactatgcc tggtacacag taggttctta atatgtgttg aatatagcca   7500

tcaaattgat attggatata attcaatctg ataagatatt ttgagatatt aaagagtttt   7560

taacttgata ccataaaaaa aaaaaaaaaa a                                  7591
```

```
<210> SEQ ID NO 18
<211> LENGTH: 518
<212> TYPE: PRT
<213> ORGANISM: Homo sapiens

<400> SEQUENCE: 18

Met Pro Glu Ala Asn Tyr Leu Leu Ser Val Ser Trp Gly Tyr Ile Lys
1               5                   10                  15

Phe Lys Arg Met Leu Asn Arg Glu Leu Thr His Leu Ser Glu Met Ser
            20                  25                  30

Arg Ser Gly Asn Gln Val Ser Glu Phe Ile Ser Asn Thr Phe Leu Asp
        35                  40                  45

Lys Gln His Glu Val Glu Ile Pro Ser Pro Thr Gln Lys Glu Lys Glu
    50                  55                  60

Lys Lys Lys Arg Pro Met Ser Gln Ile Ser Gly Val Lys Lys Leu Met
65                  70                  75                  80

His Ser Ser Ser Leu Thr Asn Ser Ser Ile Pro Arg Phe Gly Val Lys
                85                  90                  95

Thr Glu Gln Glu Asp Val Leu Ala Lys Glu Leu Glu Asp Val Asn Lys
            100                 105                 110

Trp Gly Leu His Val Phe Arg Ile Ala Glu Leu Ser Gly Asn Arg Pro
        115                 120                 125

Leu Thr Val Ile Met His Thr Ile Phe Gln Glu Arg Asp Leu Leu Lys
    130                 135                 140

Thr Phe Lys Ile Pro Val Asp Thr Leu Ile Thr Tyr Leu Met Thr Leu
```

```
145                 150                 155                 160

Glu Asp His Tyr His Ala Asp Val Ala Tyr His Asn Asn Ile His Ala
                165                 170                 175

Ala Asp Val Val Gln Ser Thr His Val Leu Leu Ser Thr Pro Ala Leu
            180                 185                 190

Glu Ala Val Phe Thr Asp Leu Glu Ile Leu Ala Ala Ile Phe Ala Ser
        195                 200                 205

Ala Ile His Asp Val Asp His Pro Gly Val Ser Asn Gln Phe Leu Ile
    210                 215                 220

Asn Thr Asn Ser Glu Leu Ala Leu Met Tyr Asn Asp Ser Ser Val Leu
225                 230                 235                 240

Glu Asn His His Leu Ala Val Gly Phe Lys Leu Leu Gln Glu Glu Asn
                245                 250                 255

Cys Asp Ile Phe Gln Asn Leu Thr Lys Lys Gln Arg Gln Ser Leu Arg
            260                 265                 270

Lys Met Val Ile Asp Ile Val Leu Ala Thr Asp Met Ser Lys His Met
        275                 280                 285

Asn Leu Leu Ala Asp Leu Lys Thr Met Val Glu Thr Lys Lys Val Thr
    290                 295                 300

Ser Ser Gly Val Leu Leu Leu Asp Asn Tyr Ser Asp Arg Ile Gln Val
305                 310                 315                 320

Leu Gln Asn Met Val His Cys Ala Asp Leu Ser Asn Pro Thr Lys Pro
                325                 330                 335

Leu Gln Leu Tyr Arg Gln Trp Thr Asp Arg Ile Met Glu Glu Phe Phe
            340                 345                 350

Arg Gln Gly Asp Arg Glu Arg Glu Arg Gly Met Glu Ile Ser Pro Met
        355                 360                 365

Cys Asp Lys His Asn Ala Ser Val Glu Lys Ser Gln Val Gly Phe Ile
    370                 375                 380

Asp Tyr Ile Val His Pro Leu Trp Glu Thr Trp Ala Asp Leu Val His
385                 390                 395                 400

Pro Asp Ala Gln Asp Ile Leu Asp Thr Leu Glu Asp Asn Arg Glu Trp
                405                 410                 415

Tyr Gln Ser Thr Ile Pro Gln Ser Pro Ser Pro Ala Pro Asp Asp Pro
            420                 425                 430

Glu Glu Gly Arg Gln Gly Gln Thr Glu Lys Phe Gln Phe Glu Leu Thr
        435                 440                 445

Leu Glu Glu Asp Gly Glu Ser Asp Thr Glu Lys Asp Ser Gly Ser Gln
    450                 455                 460

Val Glu Glu Asp Thr Ser Cys Ser Asp Ser Lys Thr Leu Cys Thr Gln
465                 470                 475                 480

Asp Ser Glu Ser Thr Glu Ile Pro Leu Asp Glu Gln Val Glu Glu Glu
                485                 490                 495

Ala Val Gly Glu Glu Glu Glu Ser Gln Pro Glu Ala Cys Val Ile Asp
            500                 505                 510

Asp Arg Ser Pro Asp Thr
        515
```

<210> SEQ ID NO 19
<211> LENGTH: 8130
<212> TYPE: DNA
<213> ORGANISM: Homo sapiens

<400> SEQUENCE: 19

-continued

```
agattatagc ccagcgtacg agaagcacga gtcctatagt tggcgtaccc tgaggcctgc     60
cagttcctgc cttaatgcat atgtagtcgt aattgagttc tgacacggcc ttggatgttt    120
ctgtcctaaa tagctgacat tgcatcttca agactgtcat tccagttggc ttttgagtgg    180
atacgtgcag tgagatcatt gacactggaa acactagttc ccattttaat tacttaaaac    240
accacgatga aaagaaatac ctgtgatttg ctttctcgga gcaaaagtgc ctctgaggaa    300
acactacatt ccagtaatga agaggaagac cctttccgcg gaatggaacc ctatcttgtc    360
cggagacttt catgtcgcaa tattcagctt ccccctctcg ccttcagaca gttggaacaa    420
gctgacttga aaagtgaatc agagaacatt caacgaccaa ccagcctccc cctgaagatt    480
ctgccgctga ttgctatcac ttctgcagaa tccagtggtt ttgatgtgga caatggcaca    540
tctgcgggac ggagtccctt ggatcccatg accagcccag gatccgggct aattctccaa    600
gcaaattttg tccacagtca acgacgggag tccttcctgt atcgatccga cagcgattat    660
gacctctctc caaagtctat gtcccggaac tcctccattg ccagtgatat acacggagat    720
gacttgattg tgactccatt tgctcaggtc ttggccagtc tgcgaactgt acgaaacaac    780
tttgctgcat taactaattt gcaagatcga gcacctagca aaagatcacc catgtgcaac    840
caaccatcca tcaacaaagc caccataaca gaggaggcct accagaaact ggccagcgag    900
accctggagg agctggactg gtgtctggac cagctagaga ccctacagac caggcactcc    960
gtcagtgaga tggcctccaa caagtttaaa aggatgctta atcgggagct cacccatctc   1020
tctgaaatga gtcggtctgg aaatcaagtg tcagagttta tatcaaacac attcttagat   1080
aagcaacatg aagtggaaat tccttctcca actcagaagg aaaaggagaa aaagaaaaga   1140
ccaatgtctc agatcagtgg agtcaagaaa ttgatgcaca gctctagtct gactaattca   1200
agtatcccaa ggtttggagt taaaactgaa caagaagatg tccttgccaa ggaactagaa   1260
gatgtgaaca aatggggtct tcatgttttc agaatagcag agttgtctgg taaccggccc   1320
ttgactgtta tcatgcacac cattttttcag gaacgggatt tattaaaaac atttaaaatt   1380
ccagtagata ctttaattac atatcttatg actctcgaag accattacca tgctgatgtg   1440
gcctatcaca acaatatcca tgctgcagat gttgtccagt ctactcatgt gctattatct   1500
acacctgctt tggaggctgt gtttacagat ttggagattc ttgcagcaat tttgccagt    1560
gcaatacatg atgtagatca tcctggtgtg tccaatcaat ttctgatcaa tacaaactct   1620
gaacttgcct tgatgtacaa tgattcctca gtcttagaga accatcattt ggctgtgggc   1680
tttaaattgc ttcaggaaga aaactgtgac attttccaga atttgaccaa aaaacaaaga   1740
caatctttaa ggaaaatggt cattgacatc gtacttgcaa cagatatgtc aaaacacatg   1800
aatctactgg ctgatttgaa gactatggtt gaaactaaga aagtgacaag ctctggagtt   1860
cttcttcttg ataattattc cgataggatt caggttcttc agaatatggt gcactgtgca   1920
gatctgagca acccaacaaa gcctctccag ctgtaccgcc agtggacgga ccggataatg   1980
gaggagttct tccgccaagg agaccgagag agggaacgtg gcatggagat aagccccatg   2040
tgtgacaagc acaatgcttc cgtggaaaaa tcacaggtgg gcttcataga ctatattgtt   2100
catcccctct gggagacatg ggcagacctc gtccaccctg acgcccagga tattttggac   2160
actttggagg acaatcgtga atggtaccag agcacaatcc ctcagagccc ctctcctgca   2220
cctgatgacc cagaggaggg ccggcagggt caaactgaga aattccagtt tgaactaact   2280
ttagaggaag atggtgagtc agacacggaa aaggacagtg gcagtcaagt ggaagaagac   2340
actagctgca gtgactccaa gactctttgt actcaagact cagagtctac tgaaattccc   2400
```

cttgatgaac aggttgaaga ggaggcagta ggggaagaag aggaaagcca gcctgaagcc 2460
tgtgtcatag atgatcgttc tcctgacacg taacagtgca aaaactttca tgcctttttt 2520
ttttttaagt agaaaaattg tttccaaagt gcatgtcaca tgccacaacc acggtcacac 2580
ctcactgtca tctgccagga cgtttgttga acaaaactga ccttgactac tcagtccagc 2640
gctcaggaat atcgtaacca gttttttcac ctccatgtca tccgagcaag gtggacatct 2700
tcacgaacag cgtttttaac aagatttcag cttggtagag ctgacaaagc agataaaatc 2760
tactccaaat tattttcaag agagtgtgac tcatcaggca gcccaaaagt ttattggact 2820
tggggtttct attccttttt atttgtttgc aatattttca gaagaaaggc attgcacaga 2880
gtgaacttaa tggacgaagc aacaaatatg tcaagaacag gacatagcac gaatctgtta 2940
ccagtaggag gaggatgagc cacagaaatt gcataatttt ctaatttcaa gtcttcctga 3000
tacatgactg aatagtgtgg ttcagtgagc tgcactgacc tctacatttt gtatgatatg 3060
taaaacagat tttttgtaga gcttactttt attattaaat gtattgaggt attatattta 3120
aaaaaaacta tgttcagaac ttcatctgcc actggttatt tttttctaag gagtaacttg 3180
caagttttca gtacaaatct gtgctacact ggataaaaat ctaatttatg aattttactt 3240
gcaccttata gttcatagca attaactgat ttgtagtgat tcattgtttg ttttatatac 3300
caatgacttc catattttaa aagagaaaaa caactttatg ttgcaggaaa cccttttttgt 3360
aagtctttat tatttacttt gcattttgtt tcactctttc cagataagca gagttgctct 3420
tcaccagtgt ttttcttcat gtgcaaagtg actatttgtt ctataatact tttatgtgtg 3480
ttatatcaaa tgtgtcttaa gcttcatgca aactcagtca tcagttcgtg ttgtctgaag 3540
caagtgggag atatataaat acccagtagc taaaatggtc agtctttttt agatgttttc 3600
ctacttagta tctcctaata acgttttgct gtgtcactag atgttcattt cacaagtgca 3660
tgtctttcta ataatccaca catttcatgc tctaataatc cacacatttc atgctcattt 3720
ttattgtttt tacagccagt tatagtaaga aaaaggtttt tccccttgtg ctgctttata 3780
atttagcgtg tgtctgaacc ttatccatgt ttgctagatg aggtcttgtc aaatatatca 3840
ctaccattgt caccggtgaa aagaaacagg tagttaagtt agggttaaca ttcatttcaa 3900
ccacgaggtt gtatatcatg actagctttt actcttggtt tacagagaaa agttaaacag 3960
ccaactaggc agtttttaag aatattaaca atatattaac aaacaccaat acaactaatc 4020
ctatttggtt ttaatgattt caccatggga ttaagaacta tatcaggaac atccctgaga 4080
aacggtttta agtgtagcaa ctactcttcc ttaatggaca gccacataac gtgtaggaag 4140
tcctttatca cttatcctcg atccataagc atatcttgca gaggggaact acttctttaa 4200
acacatggag ggaaagaaga tgatgccact ggcaccagag ggttagtact gtgatgcatc 4260
ctaaaatatt tattatattg gtaaaaattc tggttaaata aaaaattaga gatcactctt 4320
ggctgatttc agcaccagga actgtattac agttttagag attaattcct agtgtttacc 4380
tgattatagc agttggcatc atggggcatt taattctgac tttatcccca cgtcagcctt 4440
aataaagtct tctttacctt ctctatgaag actttaaagc ccaaataatc atttttcaca 4500
ttgatattca agaattgaga tagatagaag ccaaagtggg tatctgacaa gtggaaaatc 4560
aaacgtttaa gaagaattac aactctgaaa agcatttata tgtggaactt ctcaaggagc 4620
ctcctgggga ctggaaagta agtcatcagc caggcaaatg actcatgctg aagagagtcc 4680
ccatttcagt cccctgagat ctagctgatg cttagatcct ttgaaataaa aattatgtct 4740

```
ttataactct gatcttttac ataaagcaga agaggaatca actagttaat tgcaaggttt   4800
ctactctgtt tcctctgtaa agatcagatg gtaatctttc aaataagaaa aaaataaaga   4860
cgtatgtttg accaagtagt ttcacaagaa tatttgggaa cttgtttctt ttaattttat   4920
ttgtccctga gtgaagtcta gaaagaaagg taaagagtct agagtttatt cctctttcca   4980
aaacattctc attcctctcc tccctacact tagtatttcc cccacagagt gcctagaatc   5040
ttaataatga ataaaataaa aagcagcaat atgtcattaa caaatccaga cctgaaaggg   5100
taaagggttt ataactgcac taataaagag aggctctttt tttttcttcc agtttgttgg   5160
tttttaatgg taccgtgttg taaagatacc cactaatgga caatcaaatt gcagaaaagg   5220
ctcaatatcc aagagacagg gactaatgca ctgtacaatc tgcttatcct tgcccttctc   5280
tcttgccaaa gtgtgcttca gaaatatata ctgctttaaa aaagaataaa agaatatcct   5340
tttacaagtg gctttacatt tcctaaaatg ccataagaaa atgcaatatc tgggtactgt   5400
atggggaaaa aaatgtccaa gtttgtgtaa aaccagtgca tttcagcttg caagttactg   5460
aacacaataa tgctgtttta attttgtttt atatcagtta aaattcacaa taatgtagat   5520
agaacaaatt acagacaagg aaagaaaaaa cttgaatgaa atggatttta cagaaagctt   5580
tatgataatt tttgaatgca ttatttattt tttgtgccat gcattttttt tctcaccaaa   5640
tgaccttacc tgtaatacag tcttgtttgt ctgtttacaa ccatgtattt attgcaatgt   5700
acatactgta atgttaattg taaattatct gttcttatta aaacatcatc ccatgatggg   5760
atggtgttga tatatttgga aactcttggt gagagaatga atggtgtgta tacatactct   5820
gtacattttt cttttctcct gtaatatagt cttgtcacct tagagcttgt ttatggaaga   5880
ttcaagaaaa ctataaaata cttaaagata tataaattta aaaaaacata gctgcaggtc   5940
tttggtccca gggctgtgcc ttaactttaa ccaatatttt cttctgtttt gctgcatttg   6000
aaaggtaaca gtggagctag ggctgggcat tttacatcca ggcttttaat tgattagaat   6060
tctgccaata ggtggatttt acaaaaccac agacaacctc tgaaagattc tgagaccctt   6120
ttgagacaga agctcttaag tacttcttgc cagggagcag cactgcatgt gtgatggttg   6180
tttgccatct gttgatcagg aactacttca gctacttgca tttgattatt tccttttttt   6240
tttttttaa ctcggaaaca caactgggga aatatattct ttcccagtga ttataaacaa   6300
tctttttctt ttttttaagt ccttttggct tctagagctc ataggaaaat ggacttgatt   6360
tgaaattgga gccagagttt actcgtgttg gttatctatt catcagcttc ctgacatgtt   6420
aagagaatac attaaagaga aaatactgtt ttttaatcct aaaatttttc ttccactaag   6480
ataaaccaaa tgtccttaca tatatgtaaa cccatctatt taaacgcaaa ggtgggttga   6540
tgtcagttta catagcagaa agcattcact atcctctaag atttgtttct gcaaaacttt   6600
cattgcttta gaattttaaa atttcacctt gtacaatggc cagcccctaa agcaggaaac   6660
atttataatg gattatatgg aaacatcctc ccagtacttg cccagccctt gaatcatgtg   6720
gcttttcagt gaaaggaaag attctttttc taggaaaaat gagcctattt tattttattt   6780
tattttattt tttgacacaa actgtagatt ttagcagccc tggcccaaag gaatttgatt   6840
acttttgttt taaacagtac aaaggggaca ctataattac aaaaacatcc ttaactgatt   6900
tgagttgttt ttatttcttt ggatatattt tcagagtggt aaattgtgtg tgagaattac   6960
aaatgattat tcttttagtg gtttcttagc ctctcttaca gcccacgggg atagtactgt   7020
acatcaatac cttcatatga aatttttata tgcaatgaaa ataaaagcat gggttgattc   7080
tgcctattta tgactcaatc ttttacaaat aaaagattat tcattttaaa ttatagttca   7140
```

-continued

```
atcagcatgt ctcttaggat actgaacgtg gttgaaatga aaggatagtg acatcataag   7200

ttagtactga tattcataac caaataaagc caacttgagt aattttgcta cattaaaaat   7260

taccaaaatt acttagatgg cctataagat taagcatggt gttttctaag caagctttga   7320

aaggggcctt ccatacttac ttaattgaat attctgggat attgaaaatt attcagatac   7380

ttgacaatta tttttggtta cctactccgc aaactacaaa gttttaagga ctcaacaata   7440

agttaatgag acacagtgtt tgctttcatg gagcttacag tctggagggg acaaaggctt   7500

aaacaatact catataatta tatatgtgat cagtacaatg aaggagctca gtggggtaaa   7560

taagcaggaa cctgaacttg atctgttccg gagggccaca gaaggcttcc ttgaggcctt   7620

gagaaagtga tttgcatctg agttctgaag gattgtaaga ggtaactagg gaaaaagttg   7680

acaggaagag gaaggggatc cagacaagaa acatttgcaa agatcttgag gcataaatga   7740

gcttgagaca tctggagaaa ctgaggaaaa gtgagagagt aggcagggcc tggagccgca   7800

gagccattgc taaccatcct gtgtgagata tccccccattc tgtagcttta ttctcataac   7860

cctgctcaat ttctttata acacttctca cagatttata tacgtgtttg tttttgttat   7920

ctgtctctcc caccagacca cagctccatg agagcaaggt ctttgcttac caatatatca   7980

ctagcactta aaactatgcc tggtacacag taggttctta atatgtgttg aatatagcca   8040

tcaaattgat attggatata attcaatctg ataagatatt ttgagatatt aaagagtttt   8100

taacttgata ccataaaaaa aaaaaaaaaa                                    8130
```

```
<210> SEQ ID NO 20
<211> LENGTH: 748
<212> TYPE: PRT
<213> ORGANISM: Homo sapiens

<400> SEQUENCE: 20

Met Lys Arg Asn Thr Cys Asp Leu Leu Ser Arg Ser Lys Ser Ala Ser
1               5                   10                  15

Glu Glu Thr Leu His Ser Ser Asn Glu Glu Glu Asp Pro Phe Arg Gly
            20                  25                  30

Met Glu Pro Tyr Leu Val Arg Arg Leu Ser Cys Arg Asn Ile Gln Leu
        35                  40                  45

Pro Pro Leu Ala Phe Arg Gln Leu Glu Gln Ala Asp Leu Lys Ser Glu
    50                  55                  60

Ser Glu Asn Ile Gln Arg Pro Thr Ser Leu Pro Leu Lys Ile Leu Pro
65                  70                  75                  80

Leu Ile Ala Ile Thr Ser Ala Glu Ser Ser Gly Phe Asp Val Asp Asn
                85                  90                  95

Gly Thr Ser Ala Gly Arg Ser Pro Leu Asp Pro Met Thr Ser Pro Gly
            100                 105                 110

Ser Gly Leu Ile Leu Gln Ala Asn Phe Val His Ser Gln Arg Arg Glu
        115                 120                 125

Ser Phe Leu Tyr Arg Ser Asp Ser Asp Tyr Asp Leu Ser Pro Lys Ser
    130                 135                 140

Met Ser Arg Asn Ser Ser Ile Ala Ser Asp Ile His Gly Asp Asp Leu
145                 150                 155                 160

Ile Val Thr Pro Phe Ala Gln Val Leu Ala Ser Leu Arg Thr Val Arg
                165                 170                 175

Asn Asn Phe Ala Ala Leu Thr Asn Leu Gln Asp Arg Ala Pro Ser Lys
            180                 185                 190
```

-continued

```
Arg Ser Pro Met Cys Asn Gln Pro Ser Ile Asn Lys Ala Thr Ile Thr
        195                 200                 205

Glu Glu Ala Tyr Gln Lys Leu Ala Ser Glu Thr Leu Glu Glu Leu Asp
    210                 215                 220

Trp Cys Leu Asp Gln Leu Glu Thr Leu Gln Thr Arg His Ser Val Ser
225                 230                 235                 240

Glu Met Ala Ser Asn Lys Phe Lys Arg Met Leu Asn Arg Glu Leu Thr
                245                 250                 255

His Leu Ser Glu Met Ser Arg Ser Gly Asn Gln Val Ser Glu Phe Ile
            260                 265                 270

Ser Asn Thr Phe Leu Asp Lys Gln His Glu Val Glu Ile Pro Ser Pro
        275                 280                 285

Thr Gln Lys Glu Lys Glu Lys Lys Lys Arg Pro Met Ser Gln Ile Ser
    290                 295                 300

Gly Val Lys Lys Leu Met His Ser Ser Ser Leu Thr Asn Ser Ser Ile
305                 310                 315                 320

Pro Arg Phe Gly Val Lys Thr Glu Gln Glu Asp Val Leu Ala Lys Glu
                325                 330                 335

Leu Glu Asp Val Asn Lys Trp Gly Leu His Val Phe Arg Ile Ala Glu
            340                 345                 350

Leu Ser Gly Asn Arg Pro Leu Thr Val Ile Met His Thr Ile Phe Gln
        355                 360                 365

Glu Arg Asp Leu Leu Lys Thr Phe Lys Ile Pro Val Asp Thr Leu Ile
    370                 375                 380

Thr Tyr Leu Met Thr Leu Glu Asp His Tyr His Ala Asp Val Ala Tyr
385                 390                 395                 400

His Asn Asn Ile His Ala Ala Asp Val Val Gln Ser Thr His Val Leu
                405                 410                 415

Leu Ser Thr Pro Ala Leu Glu Ala Val Phe Thr Asp Leu Glu Ile Leu
            420                 425                 430

Ala Ala Ile Phe Ala Ser Ala Ile His Asp Val Asp His Pro Gly Val
        435                 440                 445

Ser Asn Gln Phe Leu Ile Asn Thr Asn Ser Glu Leu Ala Leu Met Tyr
    450                 455                 460

Asn Asp Ser Ser Val Leu Glu Asn His His Leu Ala Val Gly Phe Lys
465                 470                 475                 480

Leu Leu Gln Glu Glu Asn Cys Asp Ile Phe Gln Asn Leu Thr Lys Lys
                485                 490                 495

Gln Arg Gln Ser Leu Arg Lys Met Val Ile Asp Ile Val Leu Ala Thr
            500                 505                 510

Asp Met Ser Lys His Met Asn Leu Leu Ala Asp Leu Lys Thr Met Val
        515                 520                 525

Glu Thr Lys Lys Val Thr Ser Ser Gly Val Leu Leu Leu Asp Asn Tyr
    530                 535                 540

Ser Asp Arg Ile Gln Val Leu Gln Asn Met Val His Cys Ala Asp Leu
545                 550                 555                 560

Ser Asn Pro Thr Lys Pro Leu Gln Leu Tyr Arg Gln Trp Thr Asp Arg
                565                 570                 575

Ile Met Glu Glu Phe Phe Arg Gln Gly Asp Arg Glu Arg Glu Arg Gly
            580                 585                 590

Met Glu Ile Ser Pro Met Cys Asp Lys His Asn Ala Ser Val Glu Lys
        595                 600                 605

Ser Gln Val Gly Phe Ile Asp Tyr Ile Val His Pro Leu Trp Glu Thr
```

-continued

```
    610                 615                 620

Trp Ala Asp Leu Val His Pro Asp Ala Gln Asp Ile Leu Asp Thr Leu
625                 630                 635                 640

Glu Asp Asn Arg Glu Trp Tyr Gln Ser Thr Ile Pro Gln Ser Pro Ser
                645                 650                 655

Pro Ala Pro Asp Asp Pro Glu Glu Gly Arg Gln Gly Gln Thr Glu Lys
            660                 665                 670

Phe Gln Phe Glu Leu Thr Leu Glu Glu Asp Gly Glu Ser Asp Thr Glu
        675                 680                 685

Lys Asp Ser Gly Ser Gln Val Glu Glu Asp Thr Ser Cys Ser Asp Ser
    690                 695                 700

Lys Thr Leu Cys Thr Gln Asp Ser Glu Ser Thr Glu Ile Pro Leu Asp
705                 710                 715                 720

Glu Gln Val Glu Glu Glu Ala Val Gly Glu Glu Glu Glu Ser Gln Pro
                725                 730                 735

Glu Ala Cys Val Ile Asp Asp Arg Ser Pro Asp Thr
            740                 745


<210> SEQ ID NO 21
<211> LENGTH: 20
<212> TYPE: DNA
<213> ORGANISM: Artificial Sequence
<220> FEATURE:
<223> OTHER INFORMATION: PDE4D7_forward primer

<400> SEQUENCE: 21

gaacattcaa cgaccaacca                                                  20


<210> SEQ ID NO 22
<211> LENGTH: 20
<212> TYPE: DNA
<213> ORGANISM: Artificial Sequence
<220> FEATURE:
<223> OTHER INFORMATION: PDE4D7_reverse primer

<400> SEQUENCE: 22

tgccattgtc cacatcaaaa                                                  20


<210> SEQ ID NO 23
<211> LENGTH: 27
<212> TYPE: DNA
<213> ORGANISM: Artificial Sequence
<220> FEATURE:
<223> OTHER INFORMATION: PDE4D7 probe

<400> SEQUENCE: 23

ctgccgctga ttgctatcac ttctgca                                          27


<210> SEQ ID NO 24
<211> LENGTH: 22
<212> TYPE: DNA
<213> ORGANISM: Artificial Sequence
<220> FEATURE:
<223> OTHER INFORMATION: PDE4D7 Forward Primer 2

<400> SEQUENCE: 24

cgctgattgc tatcacttct gc                                               22


<210> SEQ ID NO 25
<211> LENGTH: 24
<212> TYPE: DNA
<213> ORGANISM: Artificial Sequence
```

<220> FEATURE:
<223> OTHER INFORMATION: PDE4D7 Reverse primer

<400> SEQUENCE: 25
gtcgttgact gtggacaaaa tttg 24

<210> SEQ ID NO 26
<211> LENGTH: 34
<212> TYPE: DNA
<213> ORGANISM: Artificial Sequence
<220> FEATURE:
<223> OTHER INFORMATION: PDE4D7 Probe 2

<400> SEQUENCE: 26
ttcccttgga tcccatgacc agcccataag ggaa 34

<210> SEQ ID NO 27
<211> LENGTH: 8130
<212> TYPE: DNA
<213> ORGANISM: Homo sapiens

<400> SEQUENCE: 27
agattatagc ccagcgtacg agaagcacga gtcctatagt tggcgtaccc tgaggcctgc 60
cagttcctgc cttaatgcat atgtagtcgt aattgagttc tgacacggcc ttggatgttt 120
ctgtcctaaa tagctgacat tgcatcttca agactgtcat tccagttggc ttttgagtgg 180
atacgtgcag tgagatcatt gacactggaa acactagttc ccattttaat tacttaaaac 240
accacgatga aaagaaatac ctgtgatttg ctttctcgga gcaaaagtgc ctctgaggaa 300
acactacatt ccagtaatga agaggaagac cctttccgcg gaatggaacc ctatcttgtc 360
cggagacttt catgtcgcaa tattcagctt ccccctctcg ccttcagaca gttggaacaa 420
gctgacttga aaagtgaatc agagaacatt caacgaccaa ccagcctccc cctgaagatt 480
ctgccgctga ttgctatcac ttctgcagaa tccagtggtt ttgatgtgga caatggcaca 540
tctgcgggac ggagtccctt ggatcccatg accagcccag gatccgggct aattctccaa 600
gcaaattttg tccacagtca acgacgggag tccttcctgt atcgatccga cagcgattat 660
gacctctctc caaagtctat gtcccggaac tcctccattg ccagtgatat acacggagat 720
gacttgattg tgactccatt tgctcaggtc ttggccagtc tgcgaactgt acgaaacaac 780
tttgctgcat taactaattt gcaagatcga gcacctagca aaagatcacc catgtgcaac 840
caaccatcca tcaacaaagc caccataaca gaggaggcct accagaaact ggccagcgag 900
accctggagg agctggactg gtgtctggac cagctagaga ccctacagac caggcactcc 960
gtcagtgaga tggcctccaa caagtttaaa aggatgctta atcgggagct cacccatctc 1020
tctgaaatga gtcggtctgg aaatcaagtg tcagagttta tatcaaacac attcttagat 1080
aagcaacatg aagtggaaat tccttctcca actcagaagg aaaaggagaa aaagaaaaga 1140
ccaatgtctc agatcagtgg agtcaagaaa ttgatgcaca gctctagtct gactaattca 1200
agtatcccaa ggtttggagt taaaactgaa caagaagatg tccttgccaa ggaactagaa 1260
gatgtgaaca aatggggtct tcatgttttc agaatagcag agttgtctgg taaccggccc 1320
ttgactgtta tcatgcacac catttttcag gaacgggatt tattaaaaac atttaaaatt 1380
ccagtagata ctttaattac atatcttatg actctcgaag accattacca tgctgatgtg 1440
gcctatcaca acaatatcca tgctgcagat gttgtccagt ctactcatgt gctattatct 1500
acacctgctt tggaggctgt gtttacagat ttggagattc ttgcagcaat tttgccagt 1560

-continued

```
gcaatacatg atgtagatca tcctggtgtg tccaatcaat ttctgatcaa tacaaactct   1620
gaacttgcct tgatgtacaa tgattcctca gtcttagaga accatcattt ggctgtgggc   1680
tttaaattgc ttcaggaaga aaactgtgac attttccaga atttgaccaa aaaacaaaga   1740
caatctttaa ggaaaatggt cattgacatc gtacttgcaa cagatatgtc aaaacacatg   1800
aatctactgg ctgatttgaa gactatggtt gaaactaaga aagtgacaag ctctggagtt   1860
cttcttcttg ataattattc cgataggatt caggttcttc agaatatggt gcactgtgca   1920
gatctgagca acccaacaaa gcctctccag ctgtaccgcc agtggacgga ccggataatg   1980
gaggagttct tccgccaagg agaccgagag agggaacgtg gcatggagat aagccccatg   2040
tgtgacaagc acaatgcttc cgtggaaaaa tcacaggtgg gcttcataga ctatattgtt   2100
catcccctct gggagacatg ggcagacctc gtccaccctg acgcccagga tattttggac   2160
actttggagg acaatcgtga atggtaccag agcacaatcc ctcagagccc ctctcctgca   2220
cctgatgacc cagaggaggg ccggcagggt caaactgaga aattccagtt tgaactaact   2280
ttagaggaag atggtgagtc agacacggaa aaggacagtg gcagtcaagt ggaagaagac   2340
actagctgca gtgactccaa gactctttgt actcaagact cagagtctac tgaaattccc   2400
cttgatgaac aggttgaaga ggaggcagta ggggaagaag aggaaagcca gcctgaagcc   2460
tgtgtcatag atgatcgttc tcctgacacg taacagtgca aaaactttca tgcctttttt   2520
tttttaagt agaaaaattg tttccaaagt gcatgtcaca tgccacaacc acggtcacac   2580
ctcactgtca tctgccagga cgtttgttga acaaaactga ccttgactac tcagtccagc   2640
gctcaggaat atcgtaacca gtttttcac ctccatgtca tccgagcaag gtggacatct   2700
tcacgaacag cgtttttaac aagatttcag cttggtagag ctgacaaagc agataaaatc   2760
tactccaaat tattttcaag agagtgtgac tcatcaggca gcccaaaagt ttattggact   2820
tggggtttct attccttttt atttgtttgc aatattttca gaagaaaggc attgcacaga   2880
gtgaacttaa tggacgaagc aacaaatatg tcaagaacag gacatagcac gaatctgtta   2940
ccagtaggag gaggatgagc cacagaaatt gcataatttt ctaatttcaa gtcttcctga   3000
tacatgactg aatagtgtgg ttcagtgagc tgcactgacc tctacatttt gtatgatatg   3060
taaaacagat tttttgtaga gcttactttt attattaaat gtattgaggt attatattta   3120
aaaaaaacta tgttcagaac ttcatctgcc actggttatt tttttctaag gagtaacttg   3180
caagttttca gtacaaatct gtgctacact ggataaaaat ctaatttatg aattttactt   3240
gcaccttata gttcatagca attaactgat ttgtagtgat tcattgtttg ttttatatac   3300
caatgacttc catattttaa aagagaaaaa caactttatg ttgcaggaaa cccttttgt   3360
aagtctttat tatttacttt gcattttgtt tcactctttc cagataagca gagttgctct   3420
tcaccagtgt tttcttcat gtgcaaagtg actatttgtt ctataatact tttatgtgtg   3480
ttatatcaaa tgtgtcttaa gcttcatgca aactcagtca tcagttcgtg ttgtctgaag   3540
caagtgggag atatataaat acccagtagc taaaatggtc agtctttttt agatgttttc   3600
ctacttagta tctcctaata acgttttgct gtgtcactag atgttcattt cacaagtgca   3660
tgtctttcta ataatccaca catttcatgc tctaataatc cacacatttc atgctcattt   3720
ttattgtttt tacagccagt tatagtaaga aaaaggtttt tccccttgtg ctgctttata   3780
atttagcgtg tgtctgaacc ttatccatgt ttgctagatg aggtcttgtc aaatatatca   3840
ctaccattgt caccggtgaa aagaaacagg tagttaagtt agggttaaca ttcatttcaa   3900
ccacgaggtt gtatatcatg actagctttt actcttggtt tacagagaaa agttaaacag   3960
```

-continued

```
ccaactaggc agtttttaag aatattaaca atatattaac aaacaccaat acaactaatc   4020
ctatttggtt ttaatgattt caccatggga ttaagaacta tatcaggaac atccctgaga   4080
aacggtttta agtgtagcaa ctactcttcc ttaatggaca gccacataac gtgtaggaag   4140
tcctttatca cttatcctcg atccataagc atatcttgca gaggggaact acttctttaa   4200
acacatggag ggaaagaaga tgatgccact ggcaccagag ggttagtact gtgatgcatc   4260
ctaaaatatt tattatattg gtaaaaattc tggttaaata aaaaattaga gatcactctt   4320
ggctgatttc agcaccagga actgtattac agttttagag attaattcct agtgtttacc   4380
tgattatagc agttggcatc atggggcatt taattctgac tttatcccca cgtcagcctt   4440
aataaagtct tctttacctt ctctatgaag actttaaagc ccaaataatc atttttcaca   4500
ttgatattca agaattgaga tagatagaag ccaaagtggg tatctgacaa gtggaaaatc   4560
aaacgtttaa gaagaattac aactctgaaa agcatttata tgtggaactt ctcaaggagc   4620
ctcctgggga ctggaaagta agtcatcagc caggcaaatg actcatgctg aagagagtcc   4680
ccatttcagt cccctgagat ctagctgatg cttagatcct ttgaaataaa aattatgtct   4740
ttataactct gatcttttac ataaagcaga agaggaatca actagttaat tgcaaggttt   4800
ctactctgtt tcctctgtaa agatcagatg gtaatctttc aaataagaaa aaaataaaga   4860
cgtatgtttg accaagtagt ttcacaagaa tatttgggaa cttgtttctt ttaattttat   4920
ttgtccctga gtgaagtcta gaaagaaagg taaagagtct agagtttatt cctctttcca   4980
aaacattctc attcctctcc tccctacact tagtatttcc cccacagagt gcctagaatc   5040
ttaataatga ataaaataaa aagcagcaat atgtcattaa caaatccaga cctgaaaggg   5100
taaagggttt ataactgcac taataaagag aggctctttt tttttcttcc agtttgttgg   5160
tttttaatgg taccgtgttg taaagatacc cactaatgga caatcaaatt gcagaaaagg   5220
ctcaatatcc aagagacagg gactaatgca ctgtacaatc tgcttatcct tgcccttctc   5280
tcttgccaaa gtgtgcttca gaaatatata ctgctttaaa aaagaataaa agaatatcct   5340
tttacaagtg gctttacatt tcctaaaatg ccataagaaa atgcaatatc tgggtactgt   5400
atggggaaaa aaatgtccaa gtttgtgtaa aaccagtgca tttcagcttg caagttactg   5460
aacacaataa tgctgtttta attttgtttt atatcagtta aaattcacaa taatgtagat   5520
agaacaaatt acagacaagg aaagaaaaaa cttgaatgaa atggatttta cagaaagctt   5580
tatgataatt tttgaatgca ttatttattt tttgtgccat gcattttttt tctcaccaaa   5640
tgaccttacc tgtaatacag tcttgtttgt ctgtttacaa ccatgtattt attgcaatgt   5700
acatactgta atgttaattg taaattatct gttcttatta aaacatcatc ccatgatggg   5760
atggtgttga tatatttgga aactcttggt gagagaatga atggtgtgta tacatactct   5820
gtacattttt cttttctcct gtaatatagt cttgtcacct tagagcttgt ttatggaaga   5880
ttcaagaaaa ctataaaata cttaaagata tataaattta aaaaaacata gctgcaggtc   5940
tttggtccca gggctgtgcc ttaactttaa ccaatatttt cttctgtttt gctgcatttg   6000
aaaggtaaca gtggagctag ggctgggcat tttacatcca ggcttttaat tgattagaat   6060
tctgccaata ggtggatttt acaaaaccac agacaacctc tgaaagattc tgagaccctt   6120
ttgagacaga agctcttaag tacttcttgc cagggagcag cactgcatgt gtgatggttg   6180
tttgccatct gttgatcagg aactacttca gctacttgca tttgattatt tccttttttt   6240
ttttttttaa ctcggaaaca caactgggga aatatattct ttcccagtga ttataaacaa   6300
```

-continued

```
tctttttctt ttttttaagt ccttttggct tctagagctc ataggaaaat ggacttgatt   6360

tgaaattgga gccagagttt actcgtgttg gttatctatt catcagcttc ctgacatgtt   6420

aagagaatac attaaagaga aaatactgtt ttttaatcct aaaatttttc ttccactaag   6480

ataaaccaaa tgtccttaca tatatgtaaa cccatctatt taaacgcaaa ggtgggttga   6540

tgtcagttta catagcagaa agcattcact atcctctaag atttgtttct gcaaaacttt   6600

cattgcttta gaattttaaa atttcacctt gtacaatggc cagcccctaa agcaggaaac   6660

atttataatg gattatatgg aaacatcctc ccagtacttg cccagccctt gaatcatgtg   6720

gcttttcagt gaaaggaaag attctttttc taggaaaaat gagcctattt tattttattt   6780

tattttattt tttgacacaa actgtagatt ttagcagccc tggcccaaag gaatttgatt   6840

acttttgttt taaacagtac aaaggggaca ctataattac aaaaacatcc ttaactgatt   6900

tgagttgttt ttatttcttt ggatatattt tcagagtggt aaattgtgtg tgagaattac   6960

aaatgattat tcttttagtg gtttcttagc ctctcttaca gcccacgggg atagtactgt   7020

acatcaatac cttcatatga aatttttata tgcaatgaaa ataaaagcat gggttgattc   7080

tgcctattta tgactcaatc ttttacaaat aaaagattat tcattttaaa ttatagttca   7140

atcagcatgt ctcttaggat actgaacgtg gttgaaatga aaggatagtg acatcataag   7200

ttagtactga tattcataac caaataaagc caacttgagt aattttgcta cattaaaaat   7260

taccaaaatt acttagatgg cctataagat taagcatggt gttttctaag caagctttga   7320

aaggggcctt ccatacttac ttaattgaat attctgggat attgaaaatt attcagatac   7380

ttgacaatta tttttggtta cctactccgc aaactacaaa gttttaagga ctcaacaata   7440

agttaatgag acacagtgtt tgctttcatg gagcttacag tctggagggg acaaaggctt   7500

aaacaatact catataatta tatatgtgat cagtacaatg aaggagctca gtggggtaaa   7560

taagcaggaa cctgaacttg atctgttccg gagggccaca gaaggcttcc ttgaggcctt   7620

gagaaagtga tttgcatctg agttctgaag gattgtaaga ggtaactagg gaaaaagttg   7680

acaggaagag gaaggggatc cagacaagaa acatttgcaa agatcttgag gcataaatga   7740

gcttgagaca tctggagaaa ctgaggaaaa gtgagagagt aggcagggcc tggagccgca   7800

gagccattgc taaccatcct gtgtgagata tcccccattc tgtagcttta ttctcataac   7860

cctgctcaat tttctttata acacttctca cagatttata tacgtgtttg tttttgttat   7920

ctgtctctcc caccagacca cagctccatg agagcaaggt ctttgcttac caatatatca   7980

ctagcactta aaactatgcc tggtacacag taggttctta atatgtgttg aatatagcca   8040

tcaaattgat attggatata attcaatctg ataagatatt ttgagatatt aaagagtttt   8100

taacttgata ccataaaaaa aaaaaaaaaa                                    8130
```

```
<210> SEQ ID NO 28
<211> LENGTH: 687
<212> TYPE: PRT
<213> ORGANISM: Homo sapiens

<400> SEQUENCE: 28

Met Ala Phe Val Trp Asp Pro Leu Gly Ala Thr Val Pro Gly Pro Ser
1               5                   10                  15

Thr Arg Ala Lys Ser Arg Leu Arg Phe Ser Lys Ser Tyr Ser Phe Asp
            20                  25                  30

Val Asp Asn Gly Thr Ser Ala Gly Arg Ser Pro Leu Asp Pro Met Thr
        35                  40                  45
```

-continued

```
Ser Pro Gly Ser Gly Leu Ile Leu Gln Ala Asn Phe Val His Ser Gln
    50                  55                  60

Arg Arg Glu Ser Phe Leu Tyr Arg Ser Asp Ser Asp Tyr Asp Leu Ser
65                  70                  75                  80

Pro Lys Ser Met Ser Arg Asn Ser Ser Ile Ala Ser Asp Ile His Gly
                85                  90                  95

Asp Asp Leu Ile Val Thr Pro Phe Ala Gln Val Leu Ala Ser Leu Arg
            100                 105                 110

Thr Val Arg Asn Asn Phe Ala Ala Leu Thr Asn Leu Gln Asp Arg Ala
        115                 120                 125

Pro Ser Lys Arg Ser Pro Met Cys Asn Gln Pro Ser Ile Asn Lys Ala
    130                 135                 140

Thr Ile Thr Glu Glu Ala Tyr Gln Lys Leu Ala Ser Glu Thr Leu Glu
145                 150                 155                 160

Glu Leu Asp Trp Cys Leu Asp Gln Leu Glu Thr Leu Gln Thr Arg His
                165                 170                 175

Ser Val Ser Glu Met Ala Ser Asn Lys Phe Lys Arg Met Leu Asn Arg
            180                 185                 190

Glu Leu Thr His Leu Ser Glu Met Ser Arg Ser Gly Asn Gln Val Ser
        195                 200                 205

Glu Phe Ile Ser Asn Thr Phe Leu Asp Lys Gln His Glu Val Glu Ile
    210                 215                 220

Pro Ser Pro Thr Gln Lys Glu Lys Glu Lys Lys Lys Arg Pro Met Ser
225                 230                 235                 240

Gln Ile Ser Gly Val Lys Lys Leu Met His Ser Ser Ser Leu Thr Asn
                245                 250                 255

Ser Ser Ile Pro Arg Phe Gly Val Lys Thr Glu Gln Glu Asp Val Leu
            260                 265                 270

Ala Lys Glu Leu Glu Asp Val Asn Lys Trp Gly Leu His Val Phe Arg
        275                 280                 285

Ile Ala Glu Leu Ser Gly Asn Arg Pro Leu Thr Val Ile Met His Thr
    290                 295                 300

Ile Phe Gln Glu Arg Asp Leu Leu Lys Thr Phe Lys Ile Pro Val Asp
305                 310                 315                 320

Thr Leu Ile Thr Tyr Leu Met Thr Leu Glu Asp His Tyr His Ala Asp
                325                 330                 335

Val Ala Tyr His Asn Asn Ile His Ala Ala Asp Val Val Gln Ser Thr
            340                 345                 350

His Val Leu Leu Ser Thr Pro Ala Leu Glu Ala Val Phe Thr Asp Leu
        355                 360                 365

Glu Ile Leu Ala Ala Ile Phe Ala Ser Ala Ile His Asp Val Asp His
    370                 375                 380

Pro Gly Val Ser Asn Gln Phe Leu Ile Asn Thr Asn Ser Glu Leu Ala
385                 390                 395                 400

Leu Met Tyr Asn Asp Ser Ser Val Leu Glu Asn His His Leu Ala Val
                405                 410                 415

Gly Phe Lys Leu Leu Gln Glu Glu Asn Cys Asp Ile Phe Gln Asn Leu
            420                 425                 430

Thr Lys Lys Gln Arg Gln Ser Leu Arg Lys Met Val Ile Asp Ile Val
        435                 440                 445

Leu Ala Thr Asp Met Ser Lys His Met Asn Leu Leu Ala Asp Leu Lys
    450                 455                 460

Thr Met Val Glu Thr Lys Lys Val Thr Ser Ser Gly Val Leu Leu Leu
```

```
465                 470                 475                 480

Asp Asn Tyr Ser Asp Arg Ile Gln Val Leu Gln Asn Met Val His Cys
                485                 490                 495

Ala Asp Leu Ser Asn Pro Thr Lys Pro Leu Gln Leu Tyr Arg Gln Trp
            500                 505                 510

Thr Asp Arg Ile Met Glu Glu Phe Phe Arg Gln Gly Asp Arg Glu Arg
        515                 520                 525

Glu Arg Gly Met Glu Ile Ser Pro Met Cys Asp Lys His Asn Ala Ser
    530                 535                 540

Val Glu Lys Ser Gln Val Gly Phe Ile Asp Tyr Ile Val His Pro Leu
545                 550                 555                 560

Trp Glu Thr Trp Ala Asp Leu Val His Pro Asp Ala Gln Asp Ile Leu
                565                 570                 575

Asp Thr Leu Glu Asp Asn Arg Glu Trp Tyr Gln Ser Thr Ile Pro Gln
            580                 585                 590

Ser Pro Ser Pro Ala Pro Asp Asp Pro Glu Glu Gly Arg Gln Gly Gln
        595                 600                 605

Thr Glu Lys Phe Gln Phe Glu Leu Thr Leu Glu Glu Asp Gly Glu Ser
    610                 615                 620

Asp Thr Glu Lys Asp Ser Gly Ser Gln Val Glu Glu Asp Thr Ser Cys
625                 630                 635                 640

Ser Asp Ser Lys Thr Leu Cys Thr Gln Asp Ser Glu Ser Thr Glu Ile
                645                 650                 655

Pro Leu Asp Glu Gln Val Glu Glu Glu Ala Val Gly Glu Glu Glu Glu
            660                 665                 670

Ser Gln Pro Glu Ala Cys Val Ile Asp Asp Arg Ser Pro Asp Thr
        675                 680                 685


<210> SEQ ID NO 29
<211> LENGTH: 8395
<212> TYPE: DNA
<213> ORGANISM: Homo sapiens

<400> SEQUENCE: 29

ttctcactgc cctgcggtgt tttgaactgc cttcttacag acgtcataca gcccttgagg      60

aatagtttct gcctggtgag attgaatgat agttctcatt cacaaaaccc tggattctaa     120

gcagggacac acagaaatta ctttcgcagg taaatcagcc cacccagcca aagtgtggag     180

agatttgttc cttggctgac ttctttgctc cacggagagg agtgttttcc tgtgcttgcc     240

ctgaaatgga acttccttga cagctctccc gtgttacagt acctcccggt catttttcttt     300

ttctctctct ctacctgcgc tcttcgagtg tcagaaacct ttaaagctgt tactatggaa     360

ttgcaaaaaa gagatcaagt gactctttca ctatgctggt ttcccttgtg acccagatga     420

agaatcaatt cagaattcag ttcctccctt ggcattgcaa gacacagaag aaactgtcac     480

ttcctaacag cctagtactg gagtaaattc agtatgaagg aagaaagcgc tcctgcgtgt     540

tagaaccttg cccatgagct ggaccgagga caggagatgg actccaggaa aattggattt     600

cttcaagcag cctcccttgg aaatggaata tctttaaaat cttctttgca gaaagacagt     660

tagaatgtat taatcagaat agttgaagac ttattttcct ttttattttt tttcaaaatg     720

agcattatta tgaagccaag atcccgatct acaagttccc taaggactgc agaggcagtt     780

tgttttgatg tggacaatgg cacatctgcg ggacggagtc ccttggatcc catgaccagc     840

ccaggatccg ggctaattct ccaagcaaat tttgtccaca gtcaacgacg ggagtccttc     900
```

-continued

```
ctgtatcgat ccgacagcga ttatgacctc tctccaaagt ctatgtcccg gaactcctcc    960
attgccagtg atatacacgg agatgacttg attgtgactc catttgctca ggtcttggcc   1020
agtctgcgaa ctgtacgaaa caactttgct gcattaacta atttgcaaga tcgagcacct   1080
agcaaaagat cacccatgtg caaccaacca tccatcaaca aagccaccat aacagaggag   1140
gcctaccaga aactggccag cgagaccctg gaggagctgg actggtgtct ggaccagcta   1200
gagaccctac agaccaggca ctccgtcagt gagatggcct ccaacaagtt taaaaggatg   1260
cttaatcggg agctcaccca tctctctgaa atgagtcggt ctggaaatca agtgtcagag   1320
tttatatcaa acacattctt agataagcaa catgaagtgg aaattccttc tccaactcag   1380
aaggaaaagg agaaaaagaa aagaccaatg tctcagatca gtggagtcaa gaaattgatg   1440
cacagctcta gtctgactaa ttcaagtatc ccaaggtttg gagttaaaac tgaacaagaa   1500
gatgtccttg ccaaggaact agaagatgtg aacaaatggg gtcttcatgt tttcagaata   1560
gcagagttgt ctggtaaccg gcccttgact gttatcatgc acaccatttt tcaggaacgg   1620
gatttattaa aaacatttaa aattccagta gatactttaa ttacatatct tatgactctc   1680
gaagaccatt accatgctga tgtggcctat cacaacaata tccatgctgc agatgttgtc   1740
cagtctactc atgtgctatt atctacacct gctttggagg ctgtgtttac agatttggag   1800
attcttgcag caatttttgc cagtgcaata catgatgtag atcatcctgg tgtgtccaat   1860
caatttctga tcaatacaaa ctctgaactt gccttgatgt acaatgattc ctcagtctta   1920
gagaaccatc atttggctgt gggctttaaa ttgcttcagg aagaaaactg tgacattttc   1980
cagaatttga ccaaaaaaca aagacaatct ttaaggaaaa tggtcattga catcgtactt   2040
gcaacagata tgtcaaaaca catgaatcta ctggctgatt tgaagactat ggttgaaact   2100
aagaaagtga caagctctgg agttcttctt cttgataatt attccgatag gattcaggtt   2160
cttcagaata tggtgcactg tgcagatctg agcaacccaa caaagcctct ccagctgtac   2220
cgccagtgga cggaccggat aatggaggag ttcttccgcc aaggagaccg agagagggaa   2280
cgtggcatgg agataagccc catgtgtgac aagcacaatg cttccgtgga aaaatcacag   2340
gtgggcttca tagactatat tgttcatccc ctctgggaga catgggcaga cctcgtccac   2400
cctgacgccc aggatatttt ggacactttg gaggacaatc gtgaatggta ccagagcaca   2460
atccctcaga gcccctctcc tgcacctgat gacccagagg agggccggca gggtcaaact   2520
gagaaattcc agtttgaact aactttagag gaagatggtg agtcagacac ggaaaaggac   2580
agtggcagtc aagtggaaga agacactagc tgcagtgact ccaagactct ttgtactcaa   2640
gactcagagt ctactgaaat tccccttgat gaacaggttg aagaggaggc agtaggggaa   2700
gaagaggaaa gccagcctga agcctgtgtc atagatgatc gttctcctga cacgtaacag   2760
tgcaaaaact ttcatgcctt ttttttttt aagtagaaaa attgtttcca aagtgcatgt   2820
cacatgccac aaccacggtc acacctcact gtcatctgcc aggacgtttg ttgaacaaaa   2880
ctgaccttga ctactcagtc cagcgctcag gaatatcgta accagttttt tcacctccat   2940
gtcatccgag caaggtggac atcttcacga acagcgtttt taacaagatt tcagcttggt   3000
agagctgaca aagcagataa aatctactcc aaattatttt caagagagtg tgactcatca   3060
ggcagcccaa aagtttattg gacttggggt ttctattcct ttttatttgt ttgcaatatt   3120
ttcagaagaa aggcattgca cagagtgaac ttaatggacg aagcaacaaa tatgtcaaga   3180
acaggacata gcacgaatct gttaccagta ggaggaggat gagccacaga aattgcataa   3240
ttttctaatt tcaagtcttc ctgatacatg actgaatagt gtggttcagt gagctgcact   3300
```

```
gacctctaca ttttgtatga tatgtaaaac agattttttg tagagcttac ttttattatt   3360
aaatgtattg aggtattata tttaaaaaaa actatgttca gaacttcatc tgccactggt   3420
tattttttc taaggagtaa cttgcaagtt ttcagtacaa atctgtgcta cactggataa   3480
aaatctaatt tatgaatttt acttgcacct tatagttcat agcaattaac tgatttgtag   3540
tgattcattg tttgttttat ataccaatga cttccatatt ttaaaagaga aaaacaactt   3600
tatgttgcag gaaacccttt ttgtaagtct ttattattta ctttgcattt tgtttcactc   3660
tttccagata agcagagttg ctcttcacca gtgtttttct tcatgtgcaa agtgactatt   3720
tgttctataa tacttttatg tgtgttatat caaatgtgtc ttaagcttca tgcaaactca   3780
gtcatcagtt cgtgttgtct gaagcaagtg ggagatatat aaatacccag tagctaaaat   3840
ggtcagtctt ttttagatgt tttcctactt agtatctcct aataacgttt tgctgtgtca   3900
ctagatgttc atttcacaag tgcatgtctt tctaataatc cacacatttc atgctctaat   3960
aatccacaca tttcatgctc atttttattg tttttacagc cagttatagt aagaaaaagg   4020
tttttcccct tgtgctgctt tataatttag cgtgtgtctg aaccttatcc atgtttgcta   4080
gatgaggtct tgtcaaatat atcactacca ttgtcaccgg tgaaaagaaa caggtagtta   4140
agttagggtt aacattcatt tcaaccacga ggttgtatat catgactagc ttttactctt   4200
ggtttacaga gaaaagttaa acagccaact aggcagtttt taagaatatt aacaatatat   4260
taacaaacac caatacaact aatcctattt ggttttaatg atttcaccat gggattaaga   4320
actatatcag gaacatccct gagaaacggt tttaagtgta gcaactactc ttccttaatg   4380
gacagccaca taacgtgtag gaagtccttt atcacttatc ctcgatccat aagcatatct   4440
tgcagagggg aactacttct ttaaacacat ggagggaaag aagatgatgc cactggcacc   4500
agagggttag tactgtgatg catcctaaaa tatttattat attggtaaaa attctggtta   4560
aataaaaaat tagagatcac tcttggctga tttcagcacc aggaactgta ttacagtttt   4620
agagattaat tcctagtgtt tacctgatta tagcagttgg catcatgggg catttaattc   4680
tgactttatc cccacgtcag ccttaataaa gtcttcttta ccttctctat gaagacttta   4740
aagcccaaat aatcattttt cacattgata ttcaagaatt gagatagata gaagccaaag   4800
tgggtatctg acaagtggaa aatcaaacgt ttaagaagaa ttacaactct gaaaagcatt   4860
tatatgtgga acttctcaag gagcctcctg ggactggaa agtaagtcat cagccaggca   4920
aatgactcat gctgaagaga gtccccattt cagtcccctg agatctagct gatgcttaga   4980
tcctttgaaa taaaaattat gtctttataa ctctgatctt ttacataaag cagaagagga   5040
atcaactagt taattgcaag gtttctactc tgtttcctct gtaaagatca gatggtaatc   5100
tttcaaataa gaaaaaaata aagacgtatg tttgaccaag tagtttcaca agaatatttg   5160
ggaacttgtt tcttttaatt ttatttgtcc ctgagtgaag tctagaaaga aaggtaaaga   5220
gtctagagtt tattcctctt tccaaaacat tctcattcct ctcctcccta cacttagtat   5280
ttcccccaca gagtgcctag aatcttaata atgaataaaa taaaaagcag caatatgtca   5340
ttaacaaatc cagacctgaa agggtaaagg gtttataact gcactaataa agagaggctc   5400
ttttttttc ttccagtttg ttggttttta atggtaccgt gttgtaaaga tacccactaa   5460
tggacaatca aattgcagaa aaggctcaat atccaagaga cagggactaa tgcactgtac   5520
aatctgctta tccttgccct tctctcttgc caaagtgtgc ttcagaaata tatactgctt   5580
taaaaaagaa taaaagaata tccttttaca agtggcttta catttcctaa aatgccataa   5640
```

-continued

```
gaaaatgcaa tatctgggta ctgtatgggg aaaaaaatgt ccaagtttgt gtaaaaccag   5700
tgcatttcag cttgcaagtt actgaacaca ataatgctgt tttaattttg ttttatatca   5760
gttaaaattc acaataatgt agatagaaca aattacagac aaggaaagaa aaaacttgaa   5820
tgaaatggat tttacagaaa gctttatgat aatttttgaa tgcattattt attttttgtg   5880
ccatgcattt tttttctcac caaatgacct tacctgtaat acagtcttgt ttgtctgttt   5940
acaaccatgt atttattgca atgtacatac tgtaatgtta attgtaaatt atctgttctt   6000
attaaaacat catcccatga tgggatggtg ttgatatatt tggaaactct tggtgagaga   6060
atgaatggtg tgtatacata ctctgtacat ttttcttttc tcctgtaata tagtcttgtc   6120
accttagagc ttgtttatgg aagattcaag aaaactataa aatacttaaa gatatataaa   6180
tttaaaaaaa catagctgca ggtctttggt cccagggctg tgccttaact ttaaccaata   6240
ttttcttctg ttttgctgca tttgaaaggt aacagtggag ctagggctgg gcattttaca   6300
tccaggcttt taattgatta gaattctgcc aataggtgga ttttacaaaa ccacagacaa   6360
cctctgaaag attctgagac ccttttgaga cagaagctct taagtacttc ttgccaggga   6420
gcagcactgc atgtgtgatg gttgtttgcc atctgttgat caggaactac ttcagctact   6480
tgcatttgat tatttccttt tttttttttt ttaactcgga aacacaactg ggaaatatat   6540
ttctttccca gtgattataa acaatctttt tcttttttt aagtcctttt ggcttctaga   6600
gctcatagga aaatggactt gatttgaaat tggagccaga gtttactcgt gttggttatc   6660
tattcatcag cttcctgaca tgttaagaga atacattaaa gagaaaatac tgtttttttaa   6720
tcctaaaatt tttcttccac taagataaac caaatgtcct tacatatatg taaacccatc   6780
tatttaaacg caaaggtggg ttgatgtcag tttacatagc agaaagcatt cactatcctc   6840
taagatttgt ttctgcaaaa ctttcattgc tttagaattt taaaatttca ccttgtacaa   6900
tggccagccc ctaaagcagg aaacatttat aatggattat atggaaacat cctcccagta   6960
cttgcccagc ccttgaatca tgtggctttt cagtgaaagg aaagattctt tttctaggaa   7020
aaatgagcct attttatttt attttatttt attttttgac acaaactgta gattttagca   7080
gccctggccc aaaggaattt gattactttt gttttaaaca gtacaaaggg gacactataa   7140
ttacaaaaac atccttaact gatttgagtt gtttttattt ctttggatat attttcagag   7200
tggtaaattg tgtgtgagaa ttacaaatga ttattctttt agtggtttct tagcctctct   7260
tacagcccac ggggatagta ctgtacatca ataccttcat atgaaatttt tatatgcaat   7320
gaaaataaaa gcatgggttg attctgccta tttatgactc aatcttttac aaataaaaga   7380
ttattcattt taaattatag ttcaatcagc atgtctctta ggatactgaa cgtggttgaa   7440
atgaaaggat agtgacatca taagttagta ctgatattca taaccaaata aagccaactt   7500
gagtaatttt gctacattaa aaattaccaa aattacttag atggcctata agattaagca   7560
tggtgttttc taagcaagct ttgaaagggg ccttccatac ttacttaatt gaatattctg   7620
ggatattgaa aattattcag atacttgaca attattttg gttacctact ccgcaaacta   7680
caaagtttta aggactcaac aataagttaa tgagacacag tgtttgcttt catggagctt   7740
acagtctgga ggggacaaag gcttaaacaa tactcatata attatatatg tgatcagtac   7800
aatgaaggag ctcagtgggg taaataagca ggaacctgaa cttgatctgt tccggagggc   7860
cacagaaggc ttccttgagg ccttgagaaa gtgatttgca tctgagttct gaaggattgt   7920
aagaggtaac tagggaaaaa gttgacagga agaggaaggg gatccagaca agaaacattt   7980
gcaaagatct tgaggcataa atgagcttga gacatctgga gaaactgagg aaaagtgaga   8040
```

gagtaggcag ggcctggagc cgcagagcca ttgctaacca tcctgtgtga gatatccccc 8100
attctgtagc tttattctca taaccctgct caattttctt tataacactt ctcacagatt 8160
tatatacgtg tttgtttttg ttatctgtct ctcccaccag accacagctc catgagagca 8220
aggtctttgc ttaccaatat atcactagca cttaaaacta tgcctggtac acagtaggtt 8280
cttaatatgt gttgaatata gccatcaaat tgatattgga tataattcaa tctgataaga 8340
tattttgaga tattaaagag tttttaactt gataccataa aaaaaaaaaa aaaaa 8395

<210> SEQ ID NO 30
<211> LENGTH: 679
<212> TYPE: PRT
<213> ORGANISM: Homo sapiens

<400> SEQUENCE: 30

Met Ser Ile Ile Met Lys Pro Arg Ser Arg Ser Thr Ser Ser Leu Arg
1 5 10 15

Thr Ala Glu Ala Val Cys Phe Asp Val Asp Asn Gly Thr Ser Ala Gly
20 25 30

Arg Ser Pro Leu Asp Pro Met Thr Ser Pro Gly Ser Gly Leu Ile Leu
35 40 45

Gln Ala Asn Phe Val His Ser Gln Arg Arg Glu Ser Phe Leu Tyr Arg
50 55 60

Ser Asp Ser Asp Tyr Asp Leu Ser Pro Lys Ser Met Ser Arg Asn Ser
65 70 75 80

Ser Ile Ala Ser Asp Ile His Gly Asp Asp Leu Ile Val Thr Pro Phe
85 90 95

Ala Gln Val Leu Ala Ser Leu Arg Thr Val Arg Asn Asn Phe Ala Ala
100 105 110

Leu Thr Asn Leu Gln Asp Arg Ala Pro Ser Lys Arg Ser Pro Met Cys
115 120 125

Asn Gln Pro Ser Ile Asn Lys Ala Thr Ile Thr Glu Glu Ala Tyr Gln
130 135 140

Lys Leu Ala Ser Glu Thr Leu Glu Glu Leu Asp Trp Cys Leu Asp Gln
145 150 155 160

Leu Glu Thr Leu Gln Thr Arg His Ser Val Ser Glu Met Ala Ser Asn
165 170 175

Lys Phe Lys Arg Met Leu Asn Arg Glu Leu Thr His Leu Ser Glu Met
180 185 190

Ser Arg Ser Gly Asn Gln Val Ser Glu Phe Ile Ser Asn Thr Phe Leu
195 200 205

Asp Lys Gln His Glu Val Glu Ile Pro Ser Pro Thr Gln Lys Glu Lys
210 215 220

Glu Lys Lys Lys Arg Pro Met Ser Gln Ile Ser Gly Val Lys Lys Leu
225 230 235 240

Met His Ser Ser Ser Leu Thr Asn Ser Ser Ile Pro Arg Phe Gly Val
245 250 255

Lys Thr Glu Gln Glu Asp Val Leu Ala Lys Glu Leu Glu Asp Val Asn
260 265 270

Lys Trp Gly Leu His Val Phe Arg Ile Ala Glu Leu Ser Gly Asn Arg
275 280 285

Pro Leu Thr Val Ile Met His Thr Ile Phe Gln Glu Arg Asp Leu Leu
290 295 300

Lys Thr Phe Lys Ile Pro Val Asp Thr Leu Ile Thr Tyr Leu Met Thr

-continued

```
305                 310                 315                 320

Leu Glu Asp His Tyr His Ala Asp Val Ala Tyr His Asn Asn Ile His
                325                 330                 335

Ala Ala Asp Val Val Gln Ser Thr His Val Leu Leu Ser Thr Pro Ala
            340                 345                 350

Leu Glu Ala Val Phe Thr Asp Leu Glu Ile Leu Ala Ala Ile Phe Ala
        355                 360                 365

Ser Ala Ile His Asp Val Asp His Pro Gly Val Ser Asn Gln Phe Leu
    370                 375                 380

Ile Asn Thr Asn Ser Glu Leu Ala Leu Met Tyr Asn Asp Ser Ser Val
385                 390                 395                 400

Leu Glu Asn His His Leu Ala Val Gly Phe Lys Leu Leu Gln Glu Glu
                405                 410                 415

Asn Cys Asp Ile Phe Gln Asn Leu Thr Lys Lys Gln Arg Gln Ser Leu
            420                 425                 430

Arg Lys Met Val Ile Asp Ile Val Leu Ala Thr Asp Met Ser Lys His
        435                 440                 445

Met Asn Leu Leu Ala Asp Leu Lys Thr Met Val Glu Thr Lys Lys Val
    450                 455                 460

Thr Ser Ser Gly Val Leu Leu Leu Asp Asn Tyr Ser Asp Arg Ile Gln
465                 470                 475                 480

Val Leu Gln Asn Met Val His Cys Ala Asp Leu Ser Asn Pro Thr Lys
                485                 490                 495

Pro Leu Gln Leu Tyr Arg Gln Trp Thr Asp Arg Ile Met Glu Glu Phe
            500                 505                 510

Phe Arg Gln Gly Asp Arg Glu Arg Glu Arg Gly Met Glu Ile Ser Pro
        515                 520                 525

Met Cys Asp Lys His Asn Ala Ser Val Glu Lys Ser Gln Val Gly Phe
    530                 535                 540

Ile Asp Tyr Ile Val His Pro Leu Trp Glu Thr Trp Ala Asp Leu Val
545                 550                 555                 560

His Pro Asp Ala Gln Asp Ile Leu Asp Thr Leu Glu Asp Asn Arg Glu
                565                 570                 575

Trp Tyr Gln Ser Thr Ile Pro Gln Ser Pro Ser Pro Ala Pro Asp Asp
            580                 585                 590

Pro Glu Glu Gly Arg Gln Gly Gln Thr Glu Lys Phe Gln Phe Glu Leu
        595                 600                 605

Thr Leu Glu Glu Asp Gly Glu Ser Asp Thr Glu Lys Asp Ser Gly Ser
    610                 615                 620

Gln Val Glu Glu Asp Thr Ser Cys Ser Asp Ser Lys Thr Leu Cys Thr
625                 630                 635                 640

Gln Asp Ser Glu Ser Thr Glu Ile Pro Leu Asp Glu Gln Val Glu Glu
                645                 650                 655

Glu Ala Val Gly Glu Glu Glu Glu Ser Gln Pro Glu Ala Cys Val Ile
            660                 665                 670

Asp Asp Arg Ser Pro Asp Thr
        675
```

<210> SEQ ID NO 31
<211> LENGTH: 26
<212> TYPE: DNA
<213> ORGANISM: Artificial Sequence
<220> FEATURE:
<223> OTHER INFORMATION: PDE4D9_forward primer -continued

<400> SEQUENCE: 31
atgagcatta ttatgaagcc aagatc 26

<210> SEQ ID NO 32
<211> LENGTH: 22
<212> TYPE: DNA
<213> ORGANISM: Artificial Sequence
<220> FEATURE:
<223> OTHER INFORMATION: PDE4D9_reverse primer

<400> SEQUENCE: 32
gtgccattgt ccacatcaaa ac 22

<210> SEQ ID NO 33
<211> LENGTH: 27
<212> TYPE: DNA
<213> ORGANISM: Artificial Sequence
<220> FEATURE:
<223> OTHER INFORMATION: PDE4D9 probe

<400> SEQUENCE: 33
ctacaagttc cctaaggact gcagagg 27

<210> SEQ ID NO 34
<211> LENGTH: 1435
<212> TYPE: DNA
<213> ORGANISM: Homo sapiens

<400> SEQUENCE: 34
ggcggggcct gcttctcctc agcttcaggc ggctgcgacg agccctcagg cgaacctctc 60
ggctttcccg cgcggcgccg cctcttgctg cgcctccgcc tcctcctctg ctccgccacc 120
ggcttcctcc tcctgagcag tcagcccgcg cgccggccgg ctccgttatg gcgacccgca 180
gccctggcgt cgtgattagt gatgatgaac caggttatga ccttgattta ttttgcatac 240
ctaatcatta tgctgaggat ttggaaaggg tgtttattcc tcatggacta attatggaca 300
ggactgaacg tcttgctcga gatgtgatga aggagatggg aggccatcac attgtagccc 360
tctgtgtgct caagggggc tataaattct ttgctgacct gctggattac atcaaagcac 420
tgaatagaaa tagtgataga tccattccta tgactgtaga ttttatcaga ctgaagagct 480
attgtaatga ccagtcaaca ggggacataa aagtaattgg tggagatgat ctctcaactt 540
taactggaaa gaatgtcttg attgtggaag atataattga cactggcaaa acaatgcaga 600
ctttgctttc cttggtcagg cagtataatc caaagatggt caaggtcgca agcttgctgg 660
tgaaaaggac cccacgaagt gttggatata agccagactt tgttggattt gaaattccag 720
acaagtttgt tgtaggatat gcccttgact ataatgaata cttcagggat ttgaatcatg 780
tttgtgtcat tagtgaaact ggaaaagcaa aatacaaagc ctaagatgag agttcaagtt 840
gagtttggaa acatctggag tcctattgac atcgccagta aaattatcaa tgttctagtt 900
ctgtggccat ctgcttagta gagctttttg catgtatctt ctaagaattt tatctgtttt 960
gtactttaga aatgtcagtt gctgcattcc taaactgttt atttgcacta tgagcctata 1020
gactatcagt tccctttggg cggattgttg tttaacttgt aaatgaaaaa attctcttaa 1080
accacagcac tattgagtga aacattgaac tcatatctgt aagaaataaa gagaagatat 1140
attagttttt taattggtat tttaattttt atatatgcag gaaagaatag aagtgattga 1200
atattgttaa ttataccacc gtgtgttaga aaagtaagaa gcagtcaatt ttcacatcaa 1260
agacagcatc taagaagttt tgttctgtcc tggaattatt ttagtagtgt ttcagtaatg 1320
ttgactgtat tttccaactt gttcaaatta ttaccagtga atctttgtca gcagttccct 1380
tttaaatgca aatcaataaa ttcccaaaaa tttaaaaaaa aaaaaaaaaa aaaaa 1435

<210> SEQ ID NO 35
<211> LENGTH: 218
<212> TYPE: PRT
<213> ORGANISM: Homo sapiens

<400> SEQUENCE: 35

Met Ala Thr Arg Ser Pro Gly Val Val Ile Ser Asp Asp Glu Pro Gly
1 5 10 15

Tyr Asp Leu Asp Leu Phe Cys Ile Pro Asn His Tyr Ala Glu Asp Leu
20 25 30

Glu Arg Val Phe Ile Pro His Gly Leu Ile Met Asp Arg Thr Glu Arg
35 40 45

Leu Ala Arg Asp Val Met Lys Glu Met Gly Gly His His Ile Val Ala
50 55 60

Leu Cys Val Leu Lys Gly Gly Tyr Lys Phe Phe Ala Asp Leu Leu Asp
65 70 75 80

Tyr Ile Lys Ala Leu Asn Arg Asn Ser Asp Arg Ser Ile Pro Met Thr
85 90 95

Val Asp Phe Ile Arg Leu Lys Ser Tyr Cys Asn Asp Gln Ser Thr Gly
100 105 110

Asp Ile Lys Val Ile Gly Gly Asp Asp Leu Ser Thr Leu Thr Gly Lys
115 120 125

Asn Val Leu Ile Val Glu Asp Ile Ile Asp Thr Gly Lys Thr Met Gln
130 135 140

Thr Leu Leu Ser Leu Val Arg Gln Tyr Asn Pro Lys Met Val Lys Val
145 150 155 160

Ala Ser Leu Leu Val Lys Arg Thr Pro Arg Ser Val Gly Tyr Lys Pro
165 170 175

Asp Phe Val Gly Phe Glu Ile Pro Asp Lys Phe Val Val Gly Tyr Ala
180 185 190

Leu Asp Tyr Asn Glu Tyr Phe Arg Asp Leu Asn His Val Cys Val Ile
195 200 205

Ser Glu Thr Gly Lys Ala Lys Tyr Lys Ala
210 215

<210> SEQ ID NO 36
<211> LENGTH: 24
<212> TYPE: DNA
<213> ORGANISM: Artificial Sequence
<220> FEATURE:
<223> OTHER INFORMATION: HPRT1_forward primer

<400> SEQUENCE: 36
gaggatttgg aaagggtgtt tatt 24

<210> SEQ ID NO 37
<211> LENGTH: 21
<212> TYPE: DNA
<213> ORGANISM: Artificial Sequence
<220> FEATURE:
<223> OTHER INFORMATION: HPRT1_reverse primer

<400> SEQUENCE: 37
acagagggct acaatgtgat g 21

-continued

<210> SEQ ID NO 38
<211> LENGTH: 26
<212> TYPE: DNA
<213> ORGANISM: Artificial Sequence
<220> FEATURE:
<223> OTHER INFORMATION: HPRT1 probe

<400> SEQUENCE: 38
acgtcttgct cgagatgtga tgaagg 26

<210> SEQ ID NO 39
<211> LENGTH: 1771
<212> TYPE: DNA
<213> ORGANISM: Homo sapiens

<400> SEQUENCE: 39
ggcggccagg ccgggcgcgg agtgggcgcg cggggccgga ggaggggcca gcgaccgcgg 60
caccgcctgt gcccgcccgc ccctccgcag ccgctactta agaggctcca gcgccggccc 120
cgccctagtg cgttacttac ctcgactctt agcttgtcgg ggacggtaac cgggacccgg 180
tgtctgctcc tgtcgccttc gcctcctaat ccctagccac tatgcgtgag tgcatctcca 240
tccacgttgg ccaggctggt gtccagattg gcaatgcctg ctgggagctc tactgcctgg 300
aacacggcat ccagcccgat ggccagatgc caagtgacaa gaccattggg ggaggagatg 360
actccttcaa caccttcttc agtgagacgg gcgctggcaa gcacgtgccc cgggctgtgt 420
ttgtagactt ggaacccaca gtcattgatg aagttcgcac tggcacctac cgccagctct 480
tccaccctga gcagctcatc acaggcaagg aagatgctgc caataactat gcccgagggc 540
actacaccat tggcaaggag atcattgacc ttgtgttgga ccgaattcgc aagctggctg 600
accagtgcac cggtcttcag ggcttcttgg ttttccacag ctttggtggg ggaactggtt 660
ctgggttcac ctccctgctc atggaacgtc tctcagttga ttatggcaag aagtccaagc 720
tggagttctc catttaccca gcaccccagg tttccacagc tgtagttgag ccctacaact 780
ccatcctcac cacccacacc accctggagc actctgattg tgccttcatg gtagacaatg 840
aggccatcta tgacatctgt cgtagaaacc tcgatatcga gcgcccaacc tacactaacc 900
ttaaccgcct tattagccag attgtgtcct ccatcactgc ttccctgaga tttgatggag 960
ccctgaatgt tgacctgaca gaattccaga ccaacctggt gccctacccc cgcatccact 1020
tccctctggc cacatatgcc cctgtcatct ctgctgagaa agcctaccat gaacagcttt 1080
ctgtagcaga gatcaccaat gcttgctttg agccagccaa ccagatggtg aaatgtgacc 1140
ctcgccatgg taaatacatg gcttgctgcc tgttgtaccg tggtgacgtg gttcccaaag 1200
atgtcaatgc tgccattgcc accatcaaaa ccaagcgcag catccagttt gtggattggt 1260
gccccactgg cttcaaggtt ggcatcaact accagcctcc cactgtggtg cctggtggag 1320
acctggccaa ggtacagaga gctgtgtgca tgctgagcaa caccacagcc attgctgagg 1380
cctgggctcg cctggaccac aagtttgacc tgatgtatgc caagcgtgcc tttgttcact 1440
ggtacgtggg tgaggggatg gaggaaggcg agttttcaga ggcccgtgaa gatatggctg 1500
cccttgagaa ggattatgag gaggttggtg tggattctgt tgaaggagag ggtgaggaag 1560
aaggagagga atactaatta tccattcctt ttggccctgc agcatgtcat gctcccagaa 1620
tttcagcttc agcttaactg acagacgtta aagctttctg gttagattgt tttcacttgg 1680
tgatcatgtc ttttccatgt gtacctgtaa tatttttcca tcatatctca aagtaaagtc 1740
attaacatca aaaaaaaaaa aaaaaaaaaa a 1771

<210> SEQ ID NO 40
<211> LENGTH: 451
<212> TYPE: PRT
<213> ORGANISM: Homo sapiens

<400> SEQUENCE: 40

```
Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
        275                 280                 285

Ala Glu Ile Thr Asn Ala Cys Phe Glu Pro Ala Asn Gln Met Val Lys
    290                 295                 300

Cys Asp Pro Arg His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                325                 330                 335

Thr Lys Arg Ser Ile Gln Phe Val Asp Trp Cys Pro Thr Gly Phe Lys
            340                 345                 350

Val Gly Ile Asn Tyr Gln Pro Pro Thr Val Val Pro Gly Gly Asp Leu
        355                 360                 365

Ala Lys Val Gln Arg Ala Val Cys Met Leu Ser Asn Thr Thr Ala Ile
```

-continued

```
    370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Val Asp Ser Val Glu Gly Glu Gly Glu Glu Glu Gly
        435                 440                 445

Glu Glu Tyr
    450


<210> SEQ ID NO 41
<211> LENGTH: 22
<212> TYPE: DNA
<213> ORGANISM: Artificial Sequence
<220> FEATURE:
<223> OTHER INFORMATION: TUBA1B_forward primer

<400> SEQUENCE: 41

tgactccttc aacaccttct tc                                              22


<210> SEQ ID NO 42
<211> LENGTH: 18
<212> TYPE: DNA
<213> ORGANISM: Artificial Sequence
<220> FEATURE:
<223> OTHER INFORMATION: TUBA1B_reverse primer

<400> SEQUENCE: 42

tgccagtgcg aacttcat                                                   18


<210> SEQ ID NO 43
<211> LENGTH: 24
<212> TYPE: DNA
<213> ORGANISM: Artificial Sequence
<220> FEATURE:
<223> OTHER INFORMATION: TUBA1B probe

<400> SEQUENCE: 43

ccgggctgtg tttgtagact tgga                                            24


<210> SEQ ID NO 44
<211> LENGTH: 5416
<212> TYPE: DNA
<213> ORGANISM: Homo sapiens

<400> SEQUENCE: 44

agtgggccgc catgttgtcg gagtgaaagg taagggggag cgagagcgcc agagagagaa      60

gatcgggggg ctgaaatcca tcttcatcct accgctccgc ccgtgttggt ggaatgagcg     120

ttgcatgtgt cttgaagaga aaagcagtgc tttggcagga ctctttcagc ccccacctga     180

aacatcaccc tcaagaacca gctaatccca acatgcctgt tgttttgaca tctggaacag     240

ggtcgcaagc gcagccacaa ccagctgcaa atcaggctct tgcagctggg actcactcca     300

gccctgtccc aggatctata ggagttgcag gccgttccca ggacgacgct atggtggact     360

acttctttca gaggcagcat ggtgagcagc ttgggggagg aggaagtgga ggaggcggct     420

ataataatag caaacatcga tggcctactg gggataacat tcatgcagaa catcaggtgc     480

gttccatgga tgaactgaat catgattttc aagcacttgc tctggaggga agagcgatgg     540
```

-continued

```
gagagcagct cttgccaggt aaaaagtttt gggaaacaga tgaatccagc aaagatggac    600
caaaaggaat attcctgggt gatcaatggc gagacagtgc ctggggaaca tcagatcatt    660
cagtttccca gccaatcatg gtgcagagaa gacctggtca gagtttccat gtgaacagtg    720
aggtcaattc tgtactgtcc ccacgatcgg agagtggggg actaggcgtt agcatggtgg    780
agtatgtgtt gagctcatcc ccgggcgatt cctgtctaag aaaaggagga tttggcccaa    840
gggatgcaga cagtgatgaa aacgacaaag gtgaaaagaa gaacaagggt acgtttgatg    900
gagataagct aggagatttg aaggaggagg gtgatgtgat ggacaagacc aatggtttac    960
cagtgcagaa tgggattgat gcagacgtca aagattttag ccgtacccct ggtaattgcc   1020
agaactctgc taatgaagtg gatcttctgg gtccaaacca gaatggttct gagggcttag   1080
cccagctgac cagcaccaat ggtgccaagc ctgtggagga tttctccaac atggagtccc   1140
agagtgtccc cttggacccc atggaacatg tgggcatgga gcctcttcag tttgattatt   1200
caggcacgca ggtacctgtg gactcagcag cagcaactgt gggacttttt gactacaatt   1260
ctcaacaaca gctgttccaa agacctaatg cgcttgctgt ccagcagttg acagctgctc   1320
agcagcagca gtatgcactg gcagctgctc atcagccgca catcggttta gctcccgctg   1380
cgtttgtccc caatccatac atcatcagcg ctgctccccc agggacggac ccctacacag   1440
ctggattggc tgcagcagcg acactaggcc cagctgtggt ccctcaccag tattatggag   1500
ttactccctg gggagtctac cctgccagtc ttttccagca gcaagctgcc gctgccgctg   1560
cagcaactaa ttcagctaat caacagacca ccccacaggc tcagcaagga cagcagcagg   1620
ttctccgtgg aggagccagc caacgtcctt tgaccccaaa ccagaaccag cagggacagc   1680
aaacggatcc ccttgtggca gctgcagcag tgaattctgc ccttgcattt ggacaaggtc   1740
tggcagcagg catgccaggt tatccggtgt tggctcctgc tgcttactat gaccaaactg   1800
gtgcccttgt agtgaatgca ggcgcgagaa atggtcttgg agctcctgtt cgacttgtag   1860
ctcctgcccc agtcatcatt agttcctcag ctgcacaagc agctgttgca gcagccgcag   1920
cttcagcaaa tggagcagct ggtggtcttg ctggaacaac aaatggacca tttcgccctt   1980
taggaacaca gcagcctcag ccccagcccc agcagcagcc caataacaac ctggcatcca   2040
gttctttcta cggcaacaac tctctgaaca gcaattcaca gagcagctcc ctcttctccc   2100
agggctctgc ccagcctgcc aacacatcct tgggattcgg aagtagcagt tctctcggcg   2160
ccaccctggg atccgccctt ggagggtttg gaacagcagt tgcaaactcc aacactggca   2220
gtggctcccg ccgtgactcc ctgactggca gcagtgacct ttataagagg acatcgagca   2280
gcttgacccc cattggacac agtttttata acggccttag cttttcctcc tctcctggac   2340
ccgtgggcat gcctctccct agtcagggac caggacattc acagacacca cctccttccc   2400
tctcttcaca tggatcctct tcaagcttaa acctgggagg actcacgaat ggcagtggaa   2460
gatacatctc tgctgctcca ggcgctgaag ccaagtaccg cagtgcaagc agcgcctcca   2520
gcctcttcag cccgagcagc actcttttct cttcctctcg tttgcgatat ggaatgtctg   2580
atgtcatgcc ttctggcagg agcaggcttt tggaagattt tcgaaacaac cggtacccca   2640
atttacaact gcgggagatt gctggacata taatggaatt ttcccaagac cagcatgggt   2700
ccagattcat tcagctgaaa ctggagcgtg ccacaccagc tgagcgccag cttgtcttca   2760
atgaaatcct ccaggctgcc taccaactca tggtggatgt gtttggtaat tacgtcattc   2820
agaagttctt tgaatttggc agtcttgaac agaagctggc tttggcagaa cggattcgag   2880
gccacgtcct gtcattggca ctacagatgt atggctgccg tgttatccag aaagctcttg   2940
```

agtttattcc ttcagaccag caggtaatta atgagatggt tcgggaacta gatggccatg 3000
tcttgaagtg tgtgaaagat cagaatggca atcacgtggt tcagaaatgc attgaatgtg 3060
tacagcccca gtctttgcaa tttatcatcg atgcgtttaa gggacaggta tttgccttat 3120
ccacacatcc ttatggctgc cgagtgattc agagaatcct ggagcactgt ctccctgacc 3180
agacactccc tattttagag gagcttcacc agcacacaga gcagcttgta caggatcaat 3240
atggaaatta tgtaatccaa catgtactgg agcacggtcg tcctgaggat aaaagcaaaa 3300
ttgtagcaga aatccgaggc aatgtacttg tattgagtca gcacaaattt gcaagcaatg 3360
ttgtggagaa gtgtgttact cacgcctcac gtacggagcg cgctgtgctc atcgatgagg 3420
tgtgcaccat gaacgacggt ccccacagtg ccttatacac catgatgaag gaccagtatg 3480
ccaactacgt ggtccagaag atgattgacg tggcggagcc aggccagcgg aagatcgtca 3540
tgcataagat ccggccccac atcgcaactc ttcgtaagta cacctatggc aagcacattc 3600
tggccaagct ggagaagtac tacatgaaga acggtgttga cttagggccc atctgtggcc 3660
cccctaatgg tatcatctga ggcagtgtca cccgctgttc cctcattccc gctgacctca 3720
ctggcccact ggcaaatcca accagcaacc agaaatgttc tagtgtagag tctgagacgg 3780
gcaagtggtt gctccaggat tactccctcc tccaaaaaag gaatcaaatc cacgagtgga 3840
aaagcctttg taaatttaat tttattacac ataacatgta ctattttttt taattgacta 3900
attgccctgc tgttttactg gtgtatagga tacttgtaca taggtaacca atgtacatgg 3960
gaggccacat attttgttca ctgttgtatc tatatttcac atgtggaaac tttcagggtg 4020
gttggtttaa caaaaaaaaa aagctttaaa aaaaaaagaa aaaaaggaaa aggtttttag 4080
ctcatttgcc tggccggcaa gttttgcaaa tagctcttcc ccacctcctc attttagtaa 4140
aaaacaaaca aaaacaaaaa aacctgagaa gtttgaattg tagttaaatg accccaaact 4200
ggcatttaac actgtttata aaaaatatat atatatatat atatatatat aatgaaaaag 4260
gtttcagagt tgctaaagct tcagtttgtg acattaagtt tatgaaattc taaaaaatgc 4320 ctttttgga gactatatta tgctgaagaa ggctgttcgt gaggaggaga tgcgagcacc 4380
cagaacgtct tttgaggctg ggcgggtgtg attgtttact gcctactgga tttttttcta 4440
ttaacattga aaggtaaaat ctgattattt agcatgagaa aaaaaaatcc aactctgctt 4500
ttggtcttgc ttctataaat atatagtgta tacttggtgt agactttgca tatatacaaa 4560
tttgtagtat tttcttgttt tgatgtctaa tctgtatcta taatgtaccc tagtagtcga 4620
acatactttt gattgtacaa ttgtacattt gtatacctgt aatgtaaatg tggagaagtt 4680
tgaatcaaca taaacacgtt ttttggtaag aaaagagaat tagccagccc tgtgcattca 4740
gtgtatattc tcacctttta tggtcgtagc atatagtgtt gtatattgta aattgtaatt 4800
tcaaccagaa gtaaattttt ttcttttgaa ggaataaatg ttctttatac agcctagtta 4860
atgtttaaaa agaaaaaaat agcttggttt tatttgtcat ctagtctcaa gtatagcgag 4920
attctttcta aatgttattc aagattgagt tctcactagt gtttttttaa tcctaaaaaa 4980
gtaatgtttt gattttgtga cagtcaaaag gacgtgcaaa agtctagcct tgcccgagct 5040
ttccttacaa tcagagcccc tctcaccttg taaagtgtga atcgcccttc ccttttgtac 5100
agaagatgaa ctgtattttg cattttgtct acttgtaagt gaatgtaaca tactgtcaat 5160
tttccttgtt tgaatataga attgtaacac tacacggtgt acatttccag agccttgtgt 5220
atatttccaa tgaacttttt tgcaagcaca cttgtaacca tatgtgtata attaacaaac 5280

-continued

```
ctgtgtatgc ttatgcctgg gcaactattt tttgtaactc ttgtgtagat tgtctctaaa   5340

caatgtgtga tctttatttt gaaaaataca gaactttgga atctgaaaaa aaaaaaaaaa   5400

aaaaaaaaaa aaaaaa                                                   5416
```

<210> SEQ ID NO 45
<211> LENGTH: 5410
<212> TYPE: DNA
<213> ORGANISM: Homo sapiens

<400> SEQUENCE: 45

```
agtgggccgc catgttgtcg gagtgaaagg taagggggag cgagagcgcc agagagagaa     60

gatcgggggg ctgaaatcca tcttcatcct accgctccgc ccgtgttggt ggaatgagcg    120

ttgcatgtgt cttgaagaga aaagcagtgc tttggcagga ctctttcagc ccccacctga    180

aacatcaccc tcaagaacca gctaatccca acatgcctgt tgttttgaca tctggaacag    240

ggtcgcaagc gcagccacaa ccagctgcaa atcaggctct tgcagctggg actcactcca    300

gccctgtccc aggatctata ggagttgcag gccgttccca ggacgacgct atggtggact    360

acttctttca gaggcagcat ggtgagcagc ttgggggagg aggaagtgga ggaggcggct    420

ataataatag caaacatcga tggcctactg ggataacat tcatgcagaa catcaggtgc    480

gttccatgga tgaactgaat catgattttc aagcacttgc tctggaggga agagcgatgg    540

gagagcagct cttgccaggt aaaaagtttt gggaaacaga tgaatccagc aaagatggac    600

caaaaggaat attcctgggt gatcaatggc gagacagtgc ctggggaaca tcagatcatt    660

cagtttccca gccaatcatg gtgcagagaa gacctggtca gagtttccat gtgaacagtg    720

aggtcaattc tgtactgtcc ccacgatcgg agagtggggg actaggcgtt agcatggtgg    780

agtatgtgtt gagctcatcc ccgggcgatt cctgtctaag aaaaggagga tttggcccaa    840

gggatgcaga cagtgatgaa aacgacaaag gtgaaaagaa gaacaagggt acgtttgatg    900

gagataagct aggagatttg aaggaggagg gtgatgtgat ggacaagacc aatggtttac    960

cagtgcagaa tgggattgat gcagacgtca aagattttag ccgtacccct ggtaattgcc   1020

agaactctgc taatgaagtg gatcttctgg gtccaaacca gaatggttct gagggcttag   1080

cccagctgac cagcaccaat ggtgccaagc ctgtggagga tttctccaac atggagtccc   1140

agagtgtccc cttggacccc atggaacatg tgggcatgga gcctcttcag tttgattatt   1200

caggcacgca ggtacctgtg gactcagcag cagcaactgt gggacttttt gactacaatt   1260

ctcaacaaca gctgttccaa agacctaatg cgcttgctgt ccagcagttg acagctgctc   1320

agcagcagca gtatgcactg gcagctgctc atcagccgca catcggttta gctcccgctg   1380

cgtttgtccc caatccatac atcatcagcg ctgctccccc agggacggac ccctacacag   1440

ctggattggc tgcagcagcg acactaggcc cagctgtggt ccctcaccag tattatggag   1500

ttactccctg gggagtctac cctgccagtc ttttccagca gcaagctgcc gctgccgctg   1560

cagcaactaa ttcagctaat caacagacca ccccacaggc tcagcaagga cagcagcagg   1620

ttctccgtgg aggagccagc caacgtcctt tgaccccaaa ccagaaccag cagggacagc   1680

aaacggatcc ccttgtggca gctgcagcag tgaattctgc ccttgcattt ggacaaggtc   1740

tggcagcagg catgccaggt tatccggtgt tggctcctgc tgcttactat gaccaaactg   1800

gtgcccttgt agtgaatgca ggcgcgagaa atggtcttgg agctcctgtt cgacttgtag   1860

ctcctgcccc agtcatcatt agttcctcag ctgcacaagc agctgttgca gcagccgcag   1920

cttcagcaaa tggagcagct ggtggtcttg ctggaacaac aaatggacca tttcgccctt   1980
```

-continued

```
taggaacaca gcagcctcag ccccagcccc agcagcagcc caataacaac ctggcatcca   2040
gttctttcta cggcaacaac tctctgaaca gcaattcaca gagcagctcc ctcttctccc   2100
agggctctgc ccagcctgcc aacacatcct tgggattcgg aagtagcagt tctctcggcg   2160
ccaccctggg atccgccctt ggagggtttg gaacagcagt tgcaaactcc aacactggca   2220
gtggctcccg ccgtgactcc ctgactggca gcagtgacct ttataagagg acatcgagca   2280
gcttgacccc cattggacac agtttttata acggccttag cttttcctcc tctcctggac   2340
ccgtgggcat gcctctccct agtcagggac caggacattc acagacacca cctccttccc   2400
tctcttcaca tggatcctct tcaagcttaa acctgggagg actcacgaat ggcagtggaa   2460
gatacatctc tgctgctcca ggcgctgaag ccaagtaccg cagtgcaagc agcgcctcca   2520
gcctcttcag cccgagcagc actcttttct cttcctctcg tttgcgatat ggaatgtctg   2580
atgtcatgcc ttctggcagg agcaggcttt tggaagattt tcgaaacaac cggtacccca   2640
atttacaact gcgggagatt gctggacata taatggaatt ttcccaagac cagcatgggt   2700
ccagattcat tcagctgaaa ctggagcgtg ccacaccagc tgagcgccag cttgtcttca   2760
atgaaatcct ccaggctgcc taccaactca tggtggatgt gtttggtaat tacgtcattc   2820
agaagttctt tgaatttggc agtcttgaac agaagctggc tttggcagaa cggattcgag   2880
gccacgtcct gtcattggca ctacagatgt atggctgccg tgttatccag aaagctcttg   2940
agtttattcc ttcagaccag cagaatgaga tggttcggga actagatggc catgtcttga   3000
agtgtgtgaa agatcagaat ggcaatcacg tggttcagaa atgcattgaa tgtgtacagc   3060
cccagtcttt gcaatttatc atcgatgcgt ttaagggaca ggtatttgcc ttatccacac   3120
atccttatgg ctgccgagtg attcagagaa tcctggagca ctgtctccct gaccagacac   3180
tccctatttt agaggagctt caccagcaca cagagcagct tgtacaggat caatatggaa   3240
attatgtaat ccaacatgta ctggagcacg gtcgtcctga ggataaaagc aaaattgtag   3300
cagaaatccg aggcaatgta cttgtattga gtcagcacaa atttgcaagc aatgttgtgg   3360
agaagtgtgt tactcacgcc tcacgtacgg agcgcgctgt gctcatcgat gaggtgtgca   3420
ccatgaacga cggtccccac agtgccttat acaccatgat gaaggaccag tatgccaact   3480
acgtggtcca gaagatgatt gacgtggcgg agccaggcca gcggaagatc gtcatgcata   3540
agatccggcc ccacatcgca actcttcgta agtacaccta tggcaagcac attctggcca   3600
agctggagaa gtactacatg aagaacggtg ttgacttagg gcccatctgt ggcccccccta   3660
atggtatcat ctgaggcagt gtcacccgct gttccctcat tcccgctgac ctcactggcc   3720
cactggcaaa tccaaccagc aaccagaaat gttctagtgt agagtctgag acgggcaagt   3780
ggttgctcca ggattactcc ctcctccaaa aaaggaatca aatccacgag tggaaaagcc   3840
tttgtaaatt taattttatt acacataaca tgtactattt tttttaattg actaattgcc   3900
ctgctgtttt actggtgtat aggatacttg tacataggta accaatgtac atgggaggcc   3960
acatattttg ttcactgttg tatctatatt tcacatgtgg aaactttcag ggtggttggt   4020
ttaacaaaaa aaaaaagctt taaaaaaaaa agaaaaaaag gaaaaggttt ttagctcatt   4080
tgcctggccg gcaagttttg caaatagctc ttccccacct cctcatttta gtaaaaaaca   4140
aacaaaaaca aaaaaacctg agaagtttga attgtagtta aatgacccca aactggcatt   4200
taacactgtt tataaaaaat atatatatat atatatatat atataatgaa aaaggtttca   4260
gagttgctaa agcttcagtt tgtgacatta agtttatgaa attctaaaaa atgcctttttt   4320
```

```
tggagactat attatgctga agaaggctgt tcgtgaggag gagatgcgag cacccagaac   4380

gtcttttgag gctgggcggg tgtgattgtt tactgcctac tggatttttt tctattaaca   4440

ttgaaaggta aaatctgatt atttagcatg agaaaaaaaa atccaactct gcttttggtc   4500

ttgcttctat aaatatatag tgtatacttg gtgtagactt tgcatatata caaatttgta   4560

gtattttctt gttttgatgt ctaatctgta tctataatgt accctagtag tcgaacatac   4620

ttttgattgt acaattgtac atttgtatac ctgtaatgta aatgtggaga agtttgaatc   4680

aacataaaca cgtttttttgg taagaaaaga gaattagcca gccctgtgca ttcagtgtat   4740

attctcacct tttatggtcg tagcatatag tgttgtatat tgtaaattgt aatttcaacc   4800

agaagtaaat tttttctttt tgaaggaata aatgttcttt atacagccta gttaatgttt   4860

aaaaagaaaa aaatagcttg gttttatttg tcatctagtc tcaagtatag cgagattctt   4920

tctaaatgtt attcaagatt gagttctcac tagtgttttt ttaatcctaa aaaagtaatg   4980

ttttgatttt gtgacagtca aaaggacgtg caaaagtcta gccttgcccg agctttcctt   5040

acaatcagag cccctctcac cttgtaaagt gtgaatcgcc cttccctttt gtacagaaga   5100

tgaactgtat tttgcatttt gtctacttgt aagtgaatgt aacatactgt caattttcct   5160

tgtttgaata tagaattgta acactacacg gtgtacattt ccagagcctt gtgtatattt   5220

ccaatgaact tttttgcaag cacacttgta accatatgtg tataattaac aaacctgtgt   5280

atgcttatgc ctgggcaact attttttgta actcttgtgt agattgtctc taaacaatgt   5340

gtgatcttta ttttgaaaaa tacagaactt tggaatctga aaaaaaaaaa aaaaaaaaaa   5400

aaaaaaaaaa                                                          5410
```

```
<210> SEQ ID NO 46
<211> LENGTH: 1188
<212> TYPE: PRT
<213> ORGANISM: Homo sapiens

<400> SEQUENCE: 46

Met Ser Val Ala Cys Val Leu Lys Arg Lys Ala Val Leu Trp Gln Asp
1               5                   10                  15

Ser Phe Ser Pro His Leu Lys His His Pro Gln Glu Pro Ala Asn Pro
            20                  25                  30

Asn Met Pro Val Val Leu Thr Ser Gly Thr Gly Ser Gln Ala Gln Pro
        35                  40                  45

Gln Pro Ala Ala Asn Gln Ala Leu Ala Ala Gly Thr His Ser Ser Pro
    50                  55                  60

Val Pro Gly Ser Ile Gly Val Ala Gly Arg Ser Gln Asp Asp Ala Met
65                  70                  75                  80

Val Asp Tyr Phe Phe Gln Arg Gln His Gly Glu Gln Leu Gly Gly Gly
                85                  90                  95

Gly Ser Gly Gly Gly Gly Tyr Asn Asn Ser Lys His Arg Trp Pro Thr
            100                 105                 110

Gly Asp Asn Ile His Ala Glu His Gln Val Arg Ser Met Asp Glu Leu
        115                 120                 125

Asn His Asp Phe Gln Ala Leu Ala Leu Glu Gly Arg Ala Met Gly Glu
    130                 135                 140

Gln Leu Leu Pro Gly Lys Lys Phe Trp Glu Thr Asp Glu Ser Ser Lys
145                 150                 155                 160

Asp Gly Pro Lys Gly Ile Phe Leu Gly Asp Gln Trp Arg Asp Ser Ala
                165                 170                 175
```

-continued

```
Trp Gly Thr Ser Asp His Ser Val Ser Gln Pro Ile Met Val Gln Arg
            180                 185                 190

Arg Pro Gly Gln Ser Phe His Val Asn Ser Glu Val Asn Ser Val Leu
        195                 200                 205

Ser Pro Arg Ser Glu Ser Gly Gly Leu Gly Val Ser Met Val Glu Tyr
    210                 215                 220

Val Leu Ser Ser Ser Pro Gly Asp Ser Cys Leu Arg Lys Gly Gly Phe
225                 230                 235                 240

Gly Pro Arg Asp Ala Asp Ser Asp Glu Asn Asp Lys Gly Glu Lys Lys
                245                 250                 255

Asn Lys Gly Thr Phe Asp Gly Asp Lys Leu Gly Asp Leu Lys Glu Glu
            260                 265                 270

Gly Asp Val Met Asp Lys Thr Asn Gly Leu Pro Val Gln Asn Gly Ile
        275                 280                 285

Asp Ala Asp Val Lys Asp Phe Ser Arg Thr Pro Gly Asn Cys Gln Asn
    290                 295                 300

Ser Ala Asn Glu Val Asp Leu Leu Gly Pro Asn Gln Asn Gly Ser Glu
305                 310                 315                 320

Gly Leu Ala Gln Leu Thr Ser Thr Asn Gly Ala Lys Pro Val Glu Asp
                325                 330                 335

Phe Ser Asn Met Glu Ser Gln Ser Val Pro Leu Asp Pro Met Glu His
            340                 345                 350

Val Gly Met Glu Pro Leu Gln Phe Asp Tyr Ser Gly Thr Gln Val Pro
        355                 360                 365

Val Asp Ser Ala Ala Ala Thr Val Gly Leu Phe Asp Tyr Asn Ser Gln
    370                 375                 380

Gln Gln Leu Phe Gln Arg Pro Asn Ala Leu Ala Val Gln Gln Leu Thr
385                 390                 395                 400

Ala Ala Gln Gln Gln Gln Tyr Ala Leu Ala Ala Ala His Gln Pro His
                405                 410                 415

Ile Gly Leu Ala Pro Ala Ala Phe Val Pro Asn Pro Tyr Ile Ile Ser
            420                 425                 430

Ala Ala Pro Pro Gly Thr Asp Pro Tyr Thr Ala Gly Leu Ala Ala Ala
        435                 440                 445

Ala Thr Leu Gly Pro Ala Val Val Pro His Gln Tyr Tyr Gly Val Thr
    450                 455                 460

Pro Trp Gly Val Tyr Pro Ala Ser Leu Phe Gln Gln Gln Ala Ala Ala
465                 470                 475                 480

Ala Ala Ala Ala Thr Asn Ser Ala Asn Gln Gln Thr Thr Pro Gln Ala
                485                 490                 495

Gln Gln Gly Gln Gln Gln Val Leu Arg Gly Gly Ala Ser Gln Arg Pro
            500                 505                 510

Leu Thr Pro Asn Gln Asn Gln Gln Gly Gln Gln Thr Asp Pro Leu Val
        515                 520                 525

Ala Ala Ala Ala Val Asn Ser Ala Leu Ala Phe Gly Gln Gly Leu Ala
    530                 535                 540

Ala Gly Met Pro Gly Tyr Pro Val Leu Ala Pro Ala Ala Tyr Tyr Asp
545                 550                 555                 560

Gln Thr Gly Ala Leu Val Val Asn Ala Gly Ala Arg Asn Gly Leu Gly
                565                 570                 575

Ala Pro Val Arg Leu Val Ala Pro Ala Pro Val Ile Ile Ser Ser Ser
            580                 585                 590

Ala Ala Gln Ala Ala Val Ala Ala Ala Ala Ala Ser Ala Asn Gly Ala
```

```
        595                 600                 605

Ala Gly Gly Leu Ala Gly Thr Thr Asn Gly Pro Phe Arg Pro Leu Gly
    610                 615                 620

Thr Gln Gln Pro Gln Pro Gln Pro Gln Gln Gln Pro Asn Asn Asn Leu
625                 630                 635                 640

Ala Ser Ser Ser Phe Tyr Gly Asn Asn Ser Leu Asn Ser Asn Ser Gln
                645                 650                 655

Ser Ser Ser Leu Phe Ser Gln Gly Ser Ala Gln Pro Ala Asn Thr Ser
            660                 665                 670

Leu Gly Phe Gly Ser Ser Ser Ser Leu Gly Ala Thr Leu Gly Ser Ala
        675                 680                 685

Leu Gly Gly Phe Gly Thr Ala Val Ala Asn Ser Asn Thr Gly Ser Gly
    690                 695                 700

Ser Arg Arg Asp Ser Leu Thr Gly Ser Ser Asp Leu Tyr Lys Arg Thr
705                 710                 715                 720

Ser Ser Ser Leu Thr Pro Ile Gly His Ser Phe Tyr Asn Gly Leu Ser
                725                 730                 735

Phe Ser Ser Ser Pro Gly Pro Val Gly Met Pro Leu Pro Ser Gln Gly
            740                 745                 750

Pro Gly His Ser Gln Thr Pro Pro Pro Ser Leu Ser Ser His Gly Ser
        755                 760                 765

Ser Ser Ser Leu Asn Leu Gly Gly Leu Thr Asn Gly Ser Gly Arg Tyr
    770                 775                 780

Ile Ser Ala Ala Pro Gly Ala Glu Ala Lys Tyr Arg Ser Ala Ser Ser
785                 790                 795                 800

Ala Ser Ser Leu Phe Ser Pro Ser Ser Thr Leu Phe Ser Ser Ser Arg
                805                 810                 815

Leu Arg Tyr Gly Met Ser Asp Val Met Pro Ser Gly Arg Ser Arg Leu
            820                 825                 830

Leu Glu Asp Phe Arg Asn Asn Arg Tyr Pro Asn Leu Gln Leu Arg Glu
        835                 840                 845

Ile Ala Gly His Ile Met Glu Phe Ser Gln Asp Gln His Gly Ser Arg
    850                 855                 860

Phe Ile Gln Leu Lys Leu Glu Arg Ala Thr Pro Ala Glu Arg Gln Leu
865                 870                 875                 880

Val Phe Asn Glu Ile Leu Gln Ala Ala Tyr Gln Leu Met Val Asp Val
                885                 890                 895

Phe Gly Asn Tyr Val Ile Gln Lys Phe Phe Glu Phe Gly Ser Leu Glu
            900                 905                 910

Gln Lys Leu Ala Leu Ala Glu Arg Ile Arg Gly His Val Leu Ser Leu
        915                 920                 925

Ala Leu Gln Met Tyr Gly Cys Arg Val Ile Gln Lys Ala Leu Glu Phe
    930                 935                 940

Ile Pro Ser Asp Gln Gln Val Ile Asn Glu Met Val Arg Glu Leu Asp
945                 950                 955                 960

Gly His Val Leu Lys Cys Val Lys Asp Gln Asn Gly Asn His Val Val
                965                 970                 975

Gln Lys Cys Ile Glu Cys Val Gln Pro Gln Ser Leu Gln Phe Ile Ile
            980                 985                 990

Asp Ala Phe Lys Gly Gln Val Phe  Ala Leu Ser Thr His  Pro Tyr Gly
        995                 1000                 1005

Cys Arg  Val Ile Gln Arg Ile  Leu Glu His Cys Leu  Pro Asp Gln
    1010                 1015                 1020
```

```
Thr Leu  Pro Ile Leu Glu Glu  Leu His Gln His Thr  Glu Gln Leu
    1025                 1030                 1035

Val Gln  Asp Gln Tyr Gly Asn  Tyr Val Ile Gln His  Val Leu Glu
    1040                 1045                 1050

His Gly  Arg Pro Glu Asp Lys  Ser Lys Ile Val Ala  Glu Ile Arg
    1055                 1060                 1065

Gly Asn  Val Leu Val Leu Ser  Gln His Lys Phe Ala  Ser Asn Val
    1070                 1075                 1080

Val Glu  Lys Cys Val Thr His  Ala Ser Arg Thr Glu  Arg Ala Val
    1085                 1090                 1095

Leu Ile  Asp Glu Val Cys Thr  Met Asn Asp Gly Pro  His Ser Ala
    1100                 1105                 1110

Leu Tyr  Thr Met Met Lys Asp  Gln Tyr Ala Asn Tyr  Val Val Gln
    1115                 1120                 1125

Lys Met  Ile Asp Val Ala Glu  Pro Gly Gln Arg Lys  Ile Val Met
    1130                 1135                 1140

His Lys  Ile Arg Pro His Ile  Ala Thr Leu Arg Lys  Tyr Thr Tyr
    1145                 1150                 1155

Gly Lys  His Ile Leu Ala Lys  Leu Glu Lys Tyr Tyr  Met Lys Asn
    1160                 1165                 1170

Gly Val  Asp Leu Gly Pro Ile  Cys Gly Pro Pro Asn  Gly Ile Ile
    1175                 1180                 1185


<210> SEQ ID NO 47
<211> LENGTH: 1186
<212> TYPE: PRT
<213> ORGANISM: Homo sapiens

<400> SEQUENCE: 47

Met Ser Val Ala Cys Val Leu Lys Arg Lys Ala Val Leu Trp Gln Asp
1               5                   10                  15

Ser Phe Ser Pro His Leu Lys His His Pro Gln Glu Pro Ala Asn Pro
            20                  25                  30

Asn Met Pro Val Val Leu Thr Ser Gly Thr Gly Ser Gln Ala Gln Pro
        35                  40                  45

Gln Pro Ala Ala Asn Gln Ala Leu Ala Ala Gly Thr His Ser Ser Pro
    50                  55                  60

Val Pro Gly Ser Ile Gly Val Ala Gly Arg Ser Gln Asp Asp Ala Met
65                  70                  75                  80

Val Asp Tyr Phe Phe Gln Arg Gln His Gly Glu Gln Leu Gly Gly Gly
                85                  90                  95

Gly Ser Gly Gly Gly Gly Tyr Asn Asn Ser Lys His Arg Trp Pro Thr
            100                 105                 110

Gly Asp Asn Ile His Ala Glu His Gln Val Arg Ser Met Asp Glu Leu
        115                 120                 125

Asn His Asp Phe Gln Ala Leu Ala Leu Glu Gly Arg Ala Met Gly Glu
    130                 135                 140

Gln Leu Leu Pro Gly Lys Lys Phe Trp Glu Thr Asp Glu Ser Ser Lys
145                 150                 155                 160

Asp Gly Pro Lys Gly Ile Phe Leu Gly Asp Gln Trp Arg Asp Ser Ala
                165                 170                 175

Trp Gly Thr Ser Asp His Ser Val Ser Gln Pro Ile Met Val Gln Arg
            180                 185                 190

Arg Pro Gly Gln Ser Phe His Val Asn Ser Glu Val Asn Ser Val Leu
```

```
        195                 200                 205

Ser Pro Arg Ser Glu Ser Gly Gly Leu Gly Val Ser Met Val Glu Tyr
    210                 215                 220

Val Leu Ser Ser Ser Pro Gly Asp Ser Cys Leu Arg Lys Gly Gly Phe
225                 230                 235                 240

Gly Pro Arg Asp Ala Asp Ser Asp Glu Asn Asp Lys Gly Glu Lys Lys
                245                 250                 255

Asn Lys Gly Thr Phe Asp Gly Asp Lys Leu Gly Asp Leu Lys Glu Glu
            260                 265                 270

Gly Asp Val Met Asp Lys Thr Asn Gly Leu Pro Val Gln Asn Gly Ile
        275                 280                 285

Asp Ala Asp Val Lys Asp Phe Ser Arg Thr Pro Gly Asn Cys Gln Asn
    290                 295                 300

Ser Ala Asn Glu Val Asp Leu Leu Gly Pro Asn Gln Asn Gly Ser Glu
305                 310                 315                 320

Gly Leu Ala Gln Leu Thr Ser Thr Asn Gly Ala Lys Pro Val Glu Asp
                325                 330                 335

Phe Ser Asn Met Glu Ser Gln Ser Val Pro Leu Asp Pro Met Glu His
            340                 345                 350

Val Gly Met Glu Pro Leu Gln Phe Asp Tyr Ser Gly Thr Gln Val Pro
        355                 360                 365

Val Asp Ser Ala Ala Ala Thr Val Gly Leu Phe Asp Tyr Asn Ser Gln
    370                 375                 380

Gln Gln Leu Phe Gln Arg Pro Asn Ala Leu Ala Val Gln Gln Leu Thr
385                 390                 395                 400

Ala Ala Gln Gln Gln Gln Tyr Ala Leu Ala Ala Ala His Gln Pro His
                405                 410                 415

Ile Gly Leu Ala Pro Ala Ala Phe Val Pro Asn Pro Tyr Ile Ile Ser
            420                 425                 430

Ala Ala Pro Pro Gly Thr Asp Pro Tyr Thr Ala Gly Leu Ala Ala Ala
        435                 440                 445

Ala Thr Leu Gly Pro Ala Val Val Pro His Gln Tyr Tyr Gly Val Thr
    450                 455                 460

Pro Trp Gly Val Tyr Pro Ala Ser Leu Phe Gln Gln Gln Ala Ala Ala
465                 470                 475                 480

Ala Ala Ala Ala Thr Asn Ser Ala Asn Gln Gln Thr Thr Pro Gln Ala
                485                 490                 495

Gln Gln Gly Gln Gln Gln Val Leu Arg Gly Gly Ala Ser Gln Arg Pro
            500                 505                 510

Leu Thr Pro Asn Gln Asn Gln Gln Gly Gln Gln Thr Asp Pro Leu Val
        515                 520                 525

Ala Ala Ala Ala Val Asn Ser Ala Leu Ala Phe Gly Gln Gly Leu Ala
    530                 535                 540

Ala Gly Met Pro Gly Tyr Pro Val Leu Ala Pro Ala Ala Tyr Tyr Asp
545                 550                 555                 560

Gln Thr Gly Ala Leu Val Val Asn Ala Gly Ala Arg Asn Gly Leu Gly
                565                 570                 575

Ala Pro Val Arg Leu Val Ala Pro Ala Pro Val Ile Ile Ser Ser Ser
            580                 585                 590

Ala Ala Gln Ala Ala Val Ala Ala Ala Ala Ala Ser Ala Asn Gly Ala
        595                 600                 605

Ala Gly Gly Leu Ala Gly Thr Thr Asn Gly Pro Phe Arg Pro Leu Gly
    610                 615                 620
```

```
Thr Gln Gln Pro Gln Pro Gln Pro Gln Gln Gln Pro Asn Asn Asn Leu
625                 630                 635                 640

Ala Ser Ser Ser Phe Tyr Gly Asn Asn Ser Leu Asn Ser Asn Ser Gln
                645                 650                 655

Ser Ser Ser Leu Phe Ser Gln Gly Ser Ala Gln Pro Ala Asn Thr Ser
            660                 665                 670

Leu Gly Phe Gly Ser Ser Ser Ser Leu Gly Ala Thr Leu Gly Ser Ala
        675                 680                 685

Leu Gly Gly Phe Gly Thr Ala Val Ala Asn Ser Asn Thr Gly Ser Gly
    690                 695                 700

Ser Arg Arg Asp Ser Leu Thr Gly Ser Ser Asp Leu Tyr Lys Arg Thr
705                 710                 715                 720

Ser Ser Ser Leu Thr Pro Ile Gly His Ser Phe Tyr Asn Gly Leu Ser
                725                 730                 735

Phe Ser Ser Ser Pro Gly Pro Val Gly Met Pro Leu Pro Ser Gln Gly
            740                 745                 750

Pro Gly His Ser Gln Thr Pro Pro Pro Ser Leu Ser Ser His Gly Ser
        755                 760                 765

Ser Ser Ser Leu Asn Leu Gly Gly Leu Thr Asn Gly Ser Gly Arg Tyr
    770                 775                 780

Ile Ser Ala Ala Pro Gly Ala Glu Ala Lys Tyr Arg Ser Ala Ser Ser
785                 790                 795                 800

Ala Ser Ser Leu Phe Ser Pro Ser Ser Thr Leu Phe Ser Ser Ser Arg
                805                 810                 815

Leu Arg Tyr Gly Met Ser Asp Val Met Pro Ser Gly Arg Ser Arg Leu
            820                 825                 830

Leu Glu Asp Phe Arg Asn Asn Arg Tyr Pro Asn Leu Gln Leu Arg Glu
        835                 840                 845

Ile Ala Gly His Ile Met Glu Phe Ser Gln Asp Gln His Gly Ser Arg
    850                 855                 860

Phe Ile Gln Leu Lys Leu Glu Arg Ala Thr Pro Ala Glu Arg Gln Leu
865                 870                 875                 880

Val Phe Asn Glu Ile Leu Gln Ala Ala Tyr Gln Leu Met Val Asp Val
                885                 890                 895

Phe Gly Asn Tyr Val Ile Gln Lys Phe Phe Glu Phe Gly Ser Leu Glu
            900                 905                 910

Gln Lys Leu Ala Leu Ala Glu Arg Ile Arg Gly His Val Leu Ser Leu
        915                 920                 925

Ala Leu Gln Met Tyr Gly Cys Arg Val Ile Gln Lys Ala Leu Glu Phe
    930                 935                 940

Ile Pro Ser Asp Gln Gln Asn Glu Met Val Arg Glu Leu Asp Gly His
945                 950                 955                 960

Val Leu Lys Cys Val Lys Asp Gln Asn Gly Asn His Val Val Gln Lys
                965                 970                 975

Cys Ile Glu Cys Val Gln Pro Gln Ser Leu Gln Phe Ile Ile Asp Ala
            980                 985                 990

Phe Lys Gly Gln Val Phe Ala Leu  Ser Thr His Pro Tyr  Gly Cys Arg
        995                 1000                1005

Val Ile  Gln Arg Ile Leu Glu  His Cys Leu Pro Asp  Gln Thr Leu
    1010                 1015                 1020

Pro Ile  Leu Glu Glu Leu His  Gln His Thr Glu Gln  Leu Val Gln
    1025                 1030                 1035
```

-continued

```
Asp Gln  Tyr Gly Asn Tyr Val  Ile Gln His Val Leu  Glu His Gly
    1040                1045                1050

Arg Pro  Glu Asp Lys Ser Lys  Ile Val Ala Glu Ile  Arg Gly Asn
    1055                1060                1065

Val Leu  Val Leu Ser Gln His  Lys Phe Ala Ser Asn  Val Val Glu
    1070                1075                1080

Lys Cys  Val Thr His Ala Ser  Arg Thr Glu Arg Ala  Val Leu Ile
    1085                1090                1095

Asp Glu  Val Cys Thr Met Asn  Asp Gly Pro His Ser  Ala Leu Tyr
    1100                1105                1110

Thr Met  Met Lys Asp Gln Tyr  Ala Asn Tyr Val Val  Gln Lys Met
    1115                1120                1125

Ile Asp  Val Ala Glu Pro Gly  Gln Arg Lys Ile Val  Met His Lys
    1130                1135                1140

Ile Arg  Pro His Ile Ala Thr  Leu Arg Lys Tyr Thr  Tyr Gly Lys
    1145                1150                1155

His Ile  Leu Ala Lys Leu Glu  Lys Tyr Tyr Met Lys  Asn Gly Val
    1160                1165                1170

Asp Leu  Gly Pro Ile Cys Gly  Pro Pro Asn Gly Ile  Ile
    1175                1180                1185
```

<210> SEQ ID NO 48
<211> LENGTH: 22
<212> TYPE: DNA
<213> ORGANISM: Artificial Sequence
<220> FEATURE:
<223> OTHER INFORMATION: PUM1_forward primer

<400> SEQUENCE: 48
gccagcttgt cttcaatgaa at 22

<210> SEQ ID NO 49
<211> LENGTH: 21
<212> TYPE: DNA
<213> ORGANISM: Artificial Sequence
<220> FEATURE:
<223> OTHER INFORMATION: PUM1_reverse primer

<400> SEQUENCE: 49
caaagccagc ttctgttcaa g 21

<210> SEQ ID NO 50
<211> LENGTH: 24
<212> TYPE: DNA
<213> ORGANISM: Artificial Sequence
<220> FEATURE:
<223> OTHER INFORMATION: PUM1 probe

<400> SEQUENCE: 50
atccaccatg agttggtagg cagc 24

<210> SEQ ID NO 51
<211> LENGTH: 1921
<212> TYPE: DNA
<213> ORGANISM: Homo sapiens

<400> SEQUENCE: 51
ggcggaagtg acattatcaa cgcgcgccag gggttcagtg aggtcgggca ggttcgctgt 60
ggcgggcgcc tgggccgccg gctgtttaac ttcgcttccg ctggcccata gtgatctttg 120
cagtgaccca gcatcactgt ttcttggcgt gtgaagataa cccaaggaat tgaggaagtt 180

```
gctgagaaga gtgtgctgga gatgctctag gaaaaaattg aatagtgaga cgagttccag    240
cgcaagggtt tctggtttgc caagaagaaa gtgaacatca tggatcagaa caacagcctg    300
ccaccttacg ctcagggctt ggcctcccct cagggtgcca tgactcccgg aatccctatc    360
tttagtccaa tgatgcctta tggcactgga ctgaccccac agcctattca gaacaccaat    420
agtctgtcta ttttggaaga gcaacaaagg cagcagcagc aacaacaaca gcagcagcag    480
cagcagcagc agcaacagca acagcagcag cagcagcagc agcagcagca gcagcagcag    540
cagcagcagc agcagcagca acaggcagtg gcagctgcag ccgttcagca gtcaacgtcc    600
cagcaggcaa cacagggaac ctcaggccag gcaccacagc tcttccactc acagactctc    660
acaactgcac ccttgccggg caccactcca ctgtatccct cccccatgac tcccatgacc    720
cccatcactc ctgccacgcc agcttcggag agttctggga ttgtaccgca gctgcaaaat    780
attgtatcca cagtgaatct tggttgtaaa cttgacctaa agaccattgc acttcgtgcc    840
cgaaacgccg aatataatcc caagcggttt gctgcggtaa tcatgaggat aagagagcca    900
cgaaccacgg cactgatttt cagttctggg aaaatggtgt gcacaggagc caagagtgaa    960
gaacagtcca gactggcagc aagaaaatat gctagagttg tacagaagtt gggttttcca   1020
gctaagttct tggacttcaa gattcagaat atggtgggga gctgtgatgt gaagtttcct   1080
ataaggttag aaggccttgt gctcacccac caacaattta gtagttatga gccagagtta   1140
tttcctggtt taatctacag aatgatcaaa cccagaattg ttctccttat ttttgtttct   1200
ggaaaagttg tattaacagg tgctaaagtc agagcagaaa tttatgaagc atttgaaaac   1260
atctacccta ttctaaaggg attcaggaag acgacgtaat ggctctcatg tacccttgcc   1320
tcccccaccc ccttcttttt tttttttaa acaaatcagt ttgttttggt acctttaaat   1380
ggtggtgttg tgagaagatg gatgttgagt tgcagggtgt ggcaccaggt gatgcccttc   1440
tgtaagtgcc caccgcggga tgccgggaag ggcattattt tgtgcactga gaacaccgcg   1500
cagcgtgact gtgagttgct cataccgtgc tgctatctgg gcagcgctgc ccatttattt   1560
atatgtagat tttaaacact gctgttgaca agttggtttg agggagaaaa ctttaagtgt   1620
taaagccacc tctataattg attggacttt ttaattttaa tgtttttccc catgaaccac   1680
agtttttata tttctaccag aaaagtaaaa atctttttta aaagtgttgt ttttctaatt   1740
tataactcct aggggttatt tctgtgccag acacattcca cctctccagt attgcaggac   1800
agaatatatg tgttaatgaa aatgaatggc tgtacatatt tttttctttc ttcagagtac   1860
tctgtacaat aaatgcagtt tataaaagtg ttagattgtt gttaaaaaaa aaaaaaaaaa   1920
a                                                                    1921
```

<210> SEQ ID NO 52
<211> LENGTH: 339
<212> TYPE: PRT
<213> ORGANISM: Homo sapiens

<400> SEQUENCE: 52

```
Met Asp Gln Asn Asn Ser Leu Pro Pro Tyr Ala Gln Gly Leu Ala Ser
1               5                   10                  15

Pro Gln Gly Ala Met Thr Pro Gly Ile Pro Ile Phe Ser Pro Met Met
            20                  25                  30

Pro Tyr Gly Thr Gly Leu Thr Pro Gln Pro Ile Gln Asn Thr Asn Ser
        35                  40                  45

Leu Ser Ile Leu Glu Glu Gln Gln Arg Gln Gln Gln Gln Gln Gln Gln
```

-continued

```
    50                  55                  60

Gln Gln Gln Gln Gln Gln Gln Gln Gln Gln Gln Gln Gln Gln Gln Gln
65                  70                  75                  80

Gln Gln Gln Gln Gln Gln Gln Gln Gln Gln Gln Gln Gln Gln Gln Ala
                85                  90                  95

Val Ala Ala Ala Ala Val Gln Gln Ser Thr Ser Gln Gln Ala Thr Gln
            100                 105                 110

Gly Thr Ser Gly Gln Ala Pro Gln Leu Phe His Ser Gln Thr Leu Thr
        115                 120                 125

Thr Ala Pro Leu Pro Gly Thr Thr Pro Leu Tyr Pro Ser Pro Met Thr
    130                 135                 140

Pro Met Thr Pro Ile Thr Pro Ala Thr Pro Ala Ser Glu Ser Ser Gly
145                 150                 155                 160

Ile Val Pro Gln Leu Gln Asn Ile Val Ser Thr Val Asn Leu Gly Cys
                165                 170                 175

Lys Leu Asp Leu Lys Thr Ile Ala Leu Arg Ala Arg Asn Ala Glu Tyr
            180                 185                 190

Asn Pro Lys Arg Phe Ala Ala Val Ile Met Arg Ile Arg Glu Pro Arg
        195                 200                 205

Thr Thr Ala Leu Ile Phe Ser Ser Gly Lys Met Val Cys Thr Gly Ala
    210                 215                 220

Lys Ser Glu Glu Gln Ser Arg Leu Ala Ala Arg Lys Tyr Ala Arg Val
225                 230                 235                 240

Val Gln Lys Leu Gly Phe Pro Ala Lys Phe Leu Asp Phe Lys Ile Gln
                245                 250                 255

Asn Met Val Gly Ser Cys Asp Val Lys Phe Pro Ile Arg Leu Glu Gly
            260                 265                 270

Leu Val Leu Thr His Gln Gln Phe Ser Ser Tyr Glu Pro Glu Leu Phe
        275                 280                 285

Pro Gly Leu Ile Tyr Arg Met Ile Lys Pro Arg Ile Val Leu Leu Ile
    290                 295                 300

Phe Val Ser Gly Lys Val Val Leu Thr Gly Ala Lys Val Arg Ala Glu
305                 310                 315                 320

Ile Tyr Glu Ala Phe Glu Asn Ile Tyr Pro Ile Leu Lys Gly Phe Arg
                325                 330                 335

Lys Thr Thr


<210> SEQ ID NO 53
<211> LENGTH: 23
<212> TYPE: DNA
<213> ORGANISM: Artificial Sequence
<220> FEATURE:
<223> OTHER INFORMATION: TBP_forward primer

<400> SEQUENCE: 53

gccaagaaga aagtgaacat cat                                           23


<210> SEQ ID NO 54
<211> LENGTH: 20
<212> TYPE: DNA
<213> ORGANISM: Artificial Sequence
<220> FEATURE:
<223> OTHER INFORMATION: TBP_reverse primer

<400> SEQUENCE: 54

atagggattc cgggagtcat                                               20
```

<210> SEQ ID NO 55
<211> LENGTH: 24
<212> TYPE: DNA
<213> ORGANISM: Artificial Sequence
<220> FEATURE:
<223> OTHER INFORMATION: TBP probe

<400> SEQUENCE: 55
tcagaacaac agcctgccac ctta 24

<210> SEQ ID NO 56
<211> LENGTH: 1852
<212> TYPE: DNA
<213> ORGANISM: Homo sapiens

<400> SEQUENCE: 56
accgccgaga ccgcgtccgc cccgcgagca cagagcctcg cctttgccga tccgccgccc 60
gtccacaccc gccgccagct caccatggat gatgatatcg ccgcgctcgt cgtcgacaac 120
ggctccggca tgtgcaaggc cggcttcgcg ggcgacgatg ccccccgggc cgtcttcccc 180
tccatcgtgg ggcgccccag gcaccagggc gtgatggtgg gcatgggtca gaaggattcc 240
tatgtgggcg acgaggccca gagcaagaga ggcatcctca ccctgaagta ccccatcgag 300
cacggcatcg tcaccaactg ggacgacatg gagaaaatct ggcaccacac cttctacaat 360
gagctgcgtg tggctcccga ggagcacccc gtgctgctga ccgaggcccc cctgaacccc 420
aaggccaacc gcgagaagat gacccagatc atgtttgaga ccttcaacac cccagccatg 480
tacgttgcta tccaggctgt gctatccctg tacgcctctg gccgtaccac tggcatcgtg 540
atggactccg gtgacggggt cacccacact gtgcccatct acgaggggta tgccctcccc 600
catgccatcc tgcgtctgga cctggctggc cgggacctga ctgactacct catgaagatc 660
ctcaccgagc gcggctacag cttcaccacc acggccgagc gggaaatcgt gcgtgacatt 720
aaggagaagc tgtgctacgt cgccctggac ttcgagcaag agatggccac ggctgcttcc 780
agctcctccc tggagaagag ctacgagctg cctgacggcc aggtcatcac cattggcaat 840
gagcggttcc gctgccctga ggcactcttc cagccttcct tcctgggcat ggagtcctgt 900
ggcatccacg aaactacctt caactccatc atgaagtgtg acgtggacat ccgcaaagac 960
ctgtacgcca acacagtgct gtctggcggc accaccatgt accctggcat tgccgacagg 1020
atgcagaagg agatcactgc cctggcaccc agcacaatga agatcaagat cattgctcct 1080
cctgagcgca agtactccgt gtggatcggc ggctccatcc tggcctcgct gtccaccttc 1140
cagcagatgt ggatcagcaa gcaggagtat gacgagtccg gcccctccat cgtccaccgc 1200
aaatgcttct aggcggacta tgacttagtt gcgttacacc ctttcttgac aaaacctaac 1260
ttgcgcagaa aacaagatga gattggcatg gctttatttg tttttttgt tttgttttgg 1320 ttttttttt ttttttggct tgactcagga tttaaaaact ggaacggtga aggtgacagc 1380
agtcggttgg agcgagcatc ccccaaagtt cacaatgtgg ccgaggactt tgattgcaca 1440
ttgttgtttt tttaatagtc attccaaata tgagatgcgt tgttacagga agtcccttgc 1500
catcctaaaa gccaccccac ttctctctaa ggagaatggc ccagtcctct cccaagtcca 1560
cacaggggag gtgatagcat tgctttcgtg taaattatgt aatgcaaaat ttttttaatc 1620
ttcgccttaa tacttttta ttttgtttta ttttgaatga tgagccttcg tgcccccct 1680 tcccccttt ttgtccccca acttgagatg tatgaaggct tttggtctcc ctgggagtgg 1740
gtggaggcag ccagggctta cctgtacact gacttgagac cagttgaata aaagtgcaca 1800

-continued

```
ccttaaaaat gaaaaaaaaa aaaaaaaaaa aaaaaaaaaa aaaaaaaaaa aa          1852


<210> SEQ ID NO 57
<211> LENGTH: 375
<212> TYPE: PRT
<213> ORGANISM: Homo sapiens

<400> SEQUENCE: 57

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365
```

```
Ile Val His Arg Lys Cys Phe
    370                 375


<210> SEQ ID NO 58
<211> LENGTH: 18
<212> TYPE: DNA
<213> ORGANISM: Artificial Sequence
<220> FEATURE:
<223> OTHER INFORMATION: ACTB_forward primer

<400> SEQUENCE: 58

ccaaccgcga gaagatga                                                    18


<210> SEQ ID NO 59
<211> LENGTH: 20
<212> TYPE: DNA
<213> ORGANISM: Artificial Sequence
<220> FEATURE:
<223> OTHER INFORMATION: ACTB_reverse primer

<400> SEQUENCE: 59

ccagaggcgt acagggatag                                                  20


<210> SEQ ID NO 60
<211> LENGTH: 23
<212> TYPE: DNA
<213> ORGANISM: Artificial Sequence
<220> FEATURE:
<223> OTHER INFORMATION: ACTB probe

<400> SEQUENCE: 60

ccatgtacgt tgctatccag gct                                              23


<210> SEQ ID NO 61
<211> LENGTH: 1229
<212> TYPE: DNA
<213> ORGANISM: Homo sapiens

<400> SEQUENCE: 61

gtctgacggg cgatggcgca gccaatagac aggagcgcta tccgcggttt ctgattggct      60

actttgttcg cattataaaa ggcacgcgcg ggcgcgaggc ccttctctcg ccaggcgtcc     120

tcgtggaagt gacatcgtct ttaaaccctg cgtggcaatc cctgacgcac cgccgtgatg     180

cccagggaag acagggcgac ctggaagtcc aactacttcc ttaagatcat ccaactattg     240

gatgattatc cgaaatgttt cattgtggga gcagacaatg tgggctccaa gcagatgcag     300

cagatccgca tgtcccttcg cgggaaggct gtggtgctga tgggcaagaa caccatgatg     360

cgcaaggcca tccgagggca cctggaaaac aacccagctc tggagaaact gctgcctcat     420

atccggggga atgtgggctt tgtgttcacc aaggaggacc tcactgagat cagggacatg     480

ttgctggcca ataaggtgcc agctgctgcc cgtgctggtg ccattgcccc atgtgaagtc     540

actgtgccag cccagaacac tggtctcggg cccgagaaga cctccttttt ccaggcttta     600

ggtatcacca ctaaaatctc caggggcacc attgaaatcc tgagtgatgt gcagctgatc     660

aagactggag acaaagtggg agccagcgaa gccacgctgc tgaacatgct caacatctcc     720

cccttctcct ttgggctggt catccagcag gtgttcgaca atggcagcat ctacaaccct     780

gaagtgcttg atatcacaga ggaaactctg cattctcgct tcctggaggg tgtccgcaat     840

gttgccagtg tctgtctgca gattggctac ccaactgttg catcagtacc ccattctatc     900

atcaacgggt acaaacgagt cctggccttg tctgtggaga cggattacac cttcccactt     960
```

```
gctgaaaagg tcaaggcctt cttggctgat ccatctgcct ttgtggctgc tgcccctgtg   1020

gctgctgcca ccacagctgc tcctgctgct gctgcagccc cagctaaggt tgaagccaag   1080

gaagagtcgg aggagtcgga cgaggatatg ggatttggtc tctttgacta atcaccaaaa   1140

agcaaccaac ttagccagtt ttatttgcaa aacaaggaaa taaaggctta cttctttaaa   1200

aagtaaaaaa aaaaaaaaaa aaaaaaaaa                                     1229
```

<210> SEQ ID NO 62
<211> LENGTH: 317
<212> TYPE: PRT
<213> ORGANISM: Homo sapiens

<400> SEQUENCE: 62

```
Met Pro Arg Glu Asp Arg Ala Thr Trp Lys Ser Asn Tyr Phe Leu Lys
1               5                   10                  15

Ile Ile Gln Leu Leu Asp Asp Tyr Pro Lys Cys Phe Ile Val Gly Ala
            20                  25                  30

Asp Asn Val Gly Ser Lys Gln Met Gln Gln Ile Arg Met Ser Leu Arg
        35                  40                  45

Gly Lys Ala Val Val Leu Met Gly Lys Asn Thr Met Met Arg Lys Ala
    50                  55                  60

Ile Arg Gly His Leu Glu Asn Asn Pro Ala Leu Glu Lys Leu Leu Pro
65                  70                  75                  80

His Ile Arg Gly Asn Val Gly Phe Val Phe Thr Lys Glu Asp Leu Thr
                85                  90                  95

Glu Ile Arg Asp Met Leu Leu Ala Asn Lys Val Pro Ala Ala Ala Arg
            100                 105                 110

Ala Gly Ala Ile Ala Pro Cys Glu Val Thr Val Pro Ala Gln Asn Thr
        115                 120                 125

Gly Leu Gly Pro Glu Lys Thr Ser Phe Phe Gln Ala Leu Gly Ile Thr
    130                 135                 140

Thr Lys Ile Ser Arg Gly Thr Ile Glu Ile Leu Ser Asp Val Gln Leu
145                 150                 155                 160

Ile Lys Thr Gly Asp Lys Val Gly Ala Ser Glu Ala Thr Leu Leu Asn
                165                 170                 175

Met Leu Asn Ile Ser Pro Phe Ser Phe Gly Leu Val Ile Gln Gln Val
            180                 185                 190

Phe Asp Asn Gly Ser Ile Tyr Asn Pro Glu Val Leu Asp Ile Thr Glu
        195                 200                 205

Glu Thr Leu His Ser Arg Phe Leu Glu Gly Val Arg Asn Val Ala Ser
    210                 215                 220

Val Cys Leu Gln Ile Gly Tyr Pro Thr Val Ala Ser Val Pro His Ser
225                 230                 235                 240

Ile Ile Asn Gly Tyr Lys Arg Val Leu Ala Leu Ser Val Glu Thr Asp
                245                 250                 255

Tyr Thr Phe Pro Leu Ala Glu Lys Val Lys Ala Phe Leu Ala Asp Pro
            260                 265                 270

Ser Ala Phe Val Ala Ala Ala Pro Val Ala Ala Ala Thr Thr Ala Ala
        275                 280                 285

Pro Ala Ala Ala Ala Ala Pro Ala Lys Val Glu Ala Lys Glu Glu Ser
    290                 295                 300

Glu Glu Ser Asp Glu Asp Met Gly Phe Gly Leu Phe Asp
305                 310                 315
```

<210> SEQ ID NO 63
<211> LENGTH: 317
<212> TYPE: PRT
<213> ORGANISM: Homo sapiens

<400> SEQUENCE: 63

```
Met Pro Arg Glu Asp Arg Ala Thr Trp Lys Ser Asn Tyr Phe Leu Lys
1               5                   10                  15

Ile Ile Gln Leu Leu Asp Asp Tyr Pro Lys Cys Phe Ile Val Gly Ala
            20                  25                  30

Asp Asn Val Gly Ser Lys Gln Met Gln Gln Ile Arg Met Ser Leu Arg
        35                  40                  45

Gly Lys Ala Val Val Leu Met Gly Lys Asn Thr Met Met Arg Lys Ala
    50                  55                  60

Ile Arg Gly His Leu Glu Asn Asn Pro Ala Leu Glu Lys Leu Leu Pro
65                  70                  75                  80

His Ile Arg Gly Asn Val Gly Phe Val Phe Thr Lys Glu Asp Leu Thr
                85                  90                  95

Glu Ile Arg Asp Met Leu Leu Ala Asn Lys Val Pro Ala Ala Ala Arg
            100                 105                 110

Ala Gly Ala Ile Ala Pro Cys Glu Val Thr Val Pro Ala Gln Asn Thr
        115                 120                 125

Gly Leu Gly Pro Glu Lys Thr Ser Phe Phe Gln Ala Leu Gly Ile Thr
    130                 135                 140

Thr Lys Ile Ser Arg Gly Thr Ile Glu Ile Leu Ser Asp Val Gln Leu
145                 150                 155                 160

Ile Lys Thr Gly Asp Lys Val Gly Ala Ser Glu Ala Thr Leu Leu Asn
                165                 170                 175

Met Leu Asn Ile Ser Pro Phe Ser Phe Gly Leu Val Ile Gln Gln Val
            180                 185                 190

Phe Asp Asn Gly Ser Ile Tyr Asn Pro Glu Val Leu Asp Ile Thr Glu
        195                 200                 205

Glu Thr Leu His Ser Arg Phe Leu Glu Gly Val Arg Asn Val Ala Ser
    210                 215                 220

Val Cys Leu Gln Ile Gly Tyr Pro Thr Val Ala Ser Val Pro His Ser
225                 230                 235                 240

Ile Ile Asn Gly Tyr Lys Arg Val Leu Ala Leu Ser Val Glu Thr Asp
                245                 250                 255

Tyr Thr Phe Pro Leu Ala Glu Lys Val Lys Ala Phe Leu Ala Asp Pro
            260                 265                 270

Ser Ala Phe Val Ala Ala Ala Pro Val Ala Ala Ala Thr Thr Ala Ala
        275                 280                 285

Pro Ala Ala Ala Ala Ala Pro Ala Lys Val Glu Ala Lys Glu Glu Ser
    290                 295                 300

Glu Glu Ser Asp Glu Asp Met Gly Phe Gly Leu Phe Asp
305                 310                 315
```

<210> SEQ ID NO 64
<211> LENGTH: 18
<212> TYPE: DNA
<213> ORGANISM: Artificial Sequence
<220> FEATURE:
<223> OTHER INFORMATION: RPLP0_forward primer

<400> SEQUENCE: 64
taaaccctgc gtggcaat 18

<210> SEQ ID NO 65
<211> LENGTH: 27
<212> TYPE: DNA
<213> ORGANISM: Artificial Sequence
<220> FEATURE:
<223> OTHER INFORMATION: RPLP0_reverse primer

<400> SEQUENCE: 65
acatttcgga taatcatcca atagttg 27

<210> SEQ ID NO 66
<211> LENGTH: 24
<212> TYPE: DNA
<213> ORGANISM: Artificial Sequence
<220> FEATURE:
<223> OTHER INFORMATION: RPLP0 probe

<400> SEQUENCE: 66
aagtagttgg acttccaggt cgcc 24

<210> SEQ ID NO 67
<211> LENGTH: 2458
<212> TYPE: DNA
<213> ORGANISM: Homo sapiens

<400> SEQUENCE: 67
cagaagaagg cagcgcccaa ggcgcatgcg cagcggtcac tcccgctgta tattaaggcg 60
ccggcgatcg cggcctgagg ctgctcccgg acaagggcaa cgagcgtttc gtttggactt 120
ctcgacttga gtgcccgcct ccttcgccgc cgcctctgca gtcctcagcg cagttatgcc 180
cagttcttcc cgctgtgggg acacgaccac ggaggaatcc ttgcttcagg gactcgggac 240
cctgctggac cccttcctcg ggtttagggg atgtggggac caggagaaag tcaggatccc 300
taagagtctt ccctgcctgg atggatgagt ggcttcttct ccacctagat tctttccaca 360
ggagccagca tacttcctga acatggagag tgttgttcgc cgctgcccat tcttatcccg 420
agtcccccag gcctttctgc agaaagcagg caaatctctg ttgttctatg cccaaaactg 480
ccccaagatg atggaagttg gggccaagcc agcccctcgg gcattgtcca ctgcagcagt 540
acactaccaa cagatcaaag aaacccctcc ggccagtgag aaagacaaaa ctgctaaggc 600
caaggtccaa cagactcctg atggatccca gcagagtcca gatggcacac agcttccgtc 660
tggacacccc ttgcctgcca caagccaggg cactgcaagc aaatgccctt tcctggcagc 720
acagatgaat cagagaggca gcagtgtctt ctgcaaagcc agtcttgagc ttcaggagga 780
tgtgcaggaa atgaatgccg tgaggaaaga ggttgctgaa acctcagcag gccccagtgt 840
ggttagtgtg aaaaccgatg gaggggatcc cagtggactg ctgaagaact tccaggacat 900
catgcaaaag caaagaccag aaagagtgtc tcatcttctt caagataact tgccaaaatc 960
tgtttccact tttcagtatg atcgtttctt tgagaaaaaa attgatgaga aaaagaatga 1020
ccacacctat cgagtttttta aaactgtgaa ccggcgagca cacatcttcc ccatggcaga 1080
tgactattca gactccctca tcaccaaaaa gcaagtgtca gtctggtgca gtaatgacta 1140
cctaggaatg agtcgccacc cacgggtgtg tggggcagtt atggacactt tgaaacaaca 1200
tggtgctggg gcaggtggta ctagaaatat ttctggaact agtaaattcc atgtggactt 1260
agagcgggag ctggcagacc tccatgggaa agatgccgca ctcttgtttt cctcgtgctt 1320
tgtggccaat gactcaaccc tcttcaccct ggctaagatg atgccaggct gtgagattta 1380

-continued

```
ctctgattct gggaaccatg cctccatgat ccaagggatt cgaaacagcc gagtgccaaa   1440

gtacatcttc cgccacaatg atgtcagcca cctcagagaa ctgctgcaaa gatctgaccc   1500

ctcagtcccc aagattgtgg catttgaaac tgtccattca atggatgggg cggtgtgccc   1560

actggaagag ctgtgtgatg tggcccatga gtttggagca atcaccttcg tggatgaggt   1620

ccacgcagtg gggctttatg gggctcgagg cggagggatt ggggatcggg atggagtcat   1680

gccaaaaatg gacatcattt ctggaacact tggcaaagcc tttggttgtg ttggagggta   1740

catcgccagc acgagttctc tgattgacac cgtacggtcc tatgctgctg gcttcatctt   1800

caccacctct ctgccaccca tgctgctggc tggagccctg gagtctgtgc ggatcctgaa   1860

gagcgctgag ggacgggtgc ttcgccgcca gcaccagcgc aacgtcaaac tcatgagaca   1920

gatgctaatg gatgccggcc tccctgttgt ccactgcccc agccacatca tccctgtgcg   1980

ggttgcagat gctgctaaaa acacagaagt ctgtgatgaa ctaatgagca gacataacat   2040

ctacgtgcaa gcaatcaatt accctacggt gccccgggga gaagagctcc tacggattgc   2100

ccccacccct caccacacac cccagatgat gaactacttc cttgagaatc tgctagtcac   2160

atggaagcaa gtggggctgg aactgaagcc tcattcctca gctgagtgca acttctgcag   2220

gaggccactg cattttgaag tgatgagtga aagagagaag tcctatttct caggcttgag   2280

caagttggta tctgctcagg cctgagcatg acctcaatta tttcacttaa ccccaggcca   2340

ttatcatatc cagatggtct tcagagttgt ctttatatgt gaattaagtt atattaaatt   2400

ttaatctata gtaaaaacat agtcctggaa ataaattctt gcttaaatgg tgaaaaaa     2458
```

<210> SEQ ID NO 68
<211> LENGTH: 2281
<212> TYPE: DNA
<213> ORGANISM: Homo sapiens

<400> SEQUENCE: 68

```
cagaagaagg cagcgcccaa ggcgcatgcg cagcggtcac tcccgctgta tattaaggcg     60

ccggcgatcg cggcctgagg ctgctcccgg acaagggcaa cgagcgtttc gtttggactt    120

ctcgacttga gtgcccgcct ccttcgccgc cgcctctgca gtcctcagcg cagtctttcc    180

acaggagcca gcatacttcc tgaacatgga gagtgttgtt cgccgctgcc cattcttatc    240

ccgagtcccc caggcctttc tgcagaaagc aggcaaatct ctgttgttct atgcccaaaa    300

ctgccccaag atgatggaag ttggggccaa gccagcccct cgggcattgt ccactgcagc    360

agtacactac caacagatca aagaaacccc tccggccagt gagaaagaca aaactgctaa    420

ggccaaggtc caacagactc ctgatggatc ccagcagagt ccagatggca cacagcttcc    480

gtctggacac cccttgcctg ccacaagcca gggcactgca agcaaatgcc ctttcctggc    540

agcacagatg aatcagagag gcagcagtgt cttctgcaaa gccagtcttg agcttcagga    600

ggatgtgcag gaaatgaatg ccgtgaggaa agaggttgct gaaacctcag caggccccag    660

tgtggttagt gtgaaaaccg atggagggga tcccagtgga ctgctgaaga acttccagga    720

catcatgcaa aagcaaagac cagaaagagt gtctcatctt cttcaagata acttgccaaa    780

atctgtttcc acttttcagt atgatcgttt ctttgagaaa aaaattgatg agaaaaagaa    840

tgaccacacc tatcgagttt ttaaaactgt gaaccggcga gcacacatct tccccatggc    900

agatgactat tcagactccc tcatcaccaa aaagcaagtg tcagtctggt gcagtaatga    960

ctacctagga atgagtcgcc acccacgggt gtgtggggca gttatggaca ctttgaaaca   1020

acatggtgct ggggcaggtg gtactagaaa tatttctgga actagtaaat tccatgtgga   1080
```

-continued

```
cttagagcgg gagctggcag acctccatgg gaaagatgcc gcactcttgt tttcctcgtg   1140

ctttgtggcc aatgactcaa ccctcttcac cctggctaag atgatgccag gctgtgagat   1200

ttactctgat tctgggaacc atgcctccat gatccaaggg attcgaaaca gccgagtgcc   1260

aaagtacatc ttccgccaca atgatgtcag ccacctcaga gaactgctgc aaagatctga   1320

cccctcagtc cccaagattg tggcatttga aactgtccat tcaatggatg gggcggtgtg   1380

cccactggaa gagctgtgtg atgtggccca tgagtttgga gcaatcacct tcgtggatga   1440

ggtccacgca gtggggcttt atggggctcg aggcggaggg attggggatc gggatggagt   1500

catgccaaaa atggacatca tttctggaac acttggcaaa gcctttggtt gtgttggagg   1560

gtacatcgcc agcacgagtt ctctgattga caccgtacgg tcctatgctg ctggcttcat   1620

cttcaccacc tctctgccac ccatgctgct ggctggagcc ctggagtctg tgcggatcct   1680

gaagagcgct gagggacggg tgcttcgccg ccagcaccag cgcaacgtca aactcatgag   1740

acagatgcta atggatgccg gcctccctgt tgtccactgc cccagccaca tcatccctgt   1800

gcgggttgca gatgctgcta aaaacacaga agtctgtgat gaactaatga gcagacataa   1860

catctacgtg caagcaatca attaccctac ggtgccccgg ggagaagagc tcctacggat   1920

tgcccccacc cctcaccaca caccccagat gatgaactac ttccttgaga atctgctagt   1980

cacatggaag caagtggggc tggaactgaa gcctcattcc tcagctgagt gcaacttctg   2040

caggaggcca ctgcattttg aagtgatgag tgaaagagag aagtcctatt tctcaggctt   2100

gagcaagttg gtatctgctc aggcctgagc atgacctcaa ttatttcact taaccccagg   2160

ccattatcat atccagatgg tcttcagagt tgtctttata tgtgaattaa gttatattaa   2220

attttaatct atagtaaaaa catagtcctg gaaataaatt cttgcttaaa tggtgaaaaa   2280

a                                                                   2281
```

<210> SEQ ID NO 69
<211> LENGTH: 640
<212> TYPE: PRT
<213> ORGANISM: Homo sapiens

<400> SEQUENCE: 69

```
Met Glu Ser Val Val Arg Arg Cys Pro Phe Leu Ser Arg Val Pro Gln
1               5                   10                  15

Ala Phe Leu Gln Lys Ala Gly Lys Ser Leu Leu Phe Tyr Ala Gln Asn
            20                  25                  30

Cys Pro Lys Met Met Glu Val Gly Ala Lys Pro Ala Pro Arg Ala Leu
        35                  40                  45

Ser Thr Ala Ala Val His Tyr Gln Gln Ile Lys Glu Thr Pro Pro Ala
    50                  55                  60

Ser Glu Lys Asp Lys Thr Ala Lys Ala Lys Val Gln Gln Thr Pro Asp
65                  70                  75                  80

Gly Ser Gln Gln Ser Pro Asp Gly Thr Gln Leu Pro Ser Gly His Pro
                85                  90                  95

Leu Pro Ala Thr Ser Gln Gly Thr Ala Ser Lys Cys Pro Phe Leu Ala
            100                 105                 110

Ala Gln Met Asn Gln Arg Gly Ser Ser Val Phe Cys Lys Ala Ser Leu
        115                 120                 125

Glu Leu Gln Glu Asp Val Gln Glu Met Asn Ala Val Arg Lys Glu Val
    130                 135                 140

Ala Glu Thr Ser Ala Gly Pro Ser Val Val Ser Val Lys Thr Asp Gly
```

-continued

```
145                 150                 155                 160

Gly Asp Pro Ser Gly Leu Leu Lys Asn Phe Gln Asp Ile Met Gln Lys
                165                 170                 175

Gln Arg Pro Glu Arg Val Ser His Leu Leu Gln Asp Asn Leu Pro Lys
            180                 185                 190

Ser Val Ser Thr Phe Gln Tyr Asp Arg Phe Phe Glu Lys Lys Ile Asp
        195                 200                 205

Glu Lys Lys Asn Asp His Thr Tyr Arg Val Phe Lys Thr Val Asn Arg
    210                 215                 220

Arg Ala His Ile Phe Pro Met Ala Asp Asp Tyr Ser Asp Ser Leu Ile
225                 230                 235                 240

Thr Lys Lys Gln Val Ser Val Trp Cys Ser Asn Asp Tyr Leu Gly Met
                245                 250                 255

Ser Arg His Pro Arg Val Cys Gly Ala Val Met Asp Thr Leu Lys Gln
            260                 265                 270

His Gly Ala Gly Ala Gly Gly Thr Arg Asn Ile Ser Gly Thr Ser Lys
        275                 280                 285

Phe His Val Asp Leu Glu Arg Glu Leu Ala Asp Leu His Gly Lys Asp
    290                 295                 300

Ala Ala Leu Leu Phe Ser Ser Cys Phe Val Ala Asn Asp Ser Thr Leu
305                 310                 315                 320

Phe Thr Leu Ala Lys Met Met Pro Gly Cys Glu Ile Tyr Ser Asp Ser
                325                 330                 335

Gly Asn His Ala Ser Met Ile Gln Gly Ile Arg Asn Ser Arg Val Pro
            340                 345                 350

Lys Tyr Ile Phe Arg His Asn Asp Val Ser His Leu Arg Glu Leu Leu
        355                 360                 365

Gln Arg Ser Asp Pro Ser Val Pro Lys Ile Val Ala Phe Glu Thr Val
    370                 375                 380

His Ser Met Asp Gly Ala Val Cys Pro Leu Glu Glu Leu Cys Asp Val
385                 390                 395                 400

Ala His Glu Phe Gly Ala Ile Thr Phe Val Asp Glu Val His Ala Val
                405                 410                 415

Gly Leu Tyr Gly Ala Arg Gly Gly Gly Ile Gly Asp Arg Asp Gly Val
            420                 425                 430

Met Pro Lys Met Asp Ile Ile Ser Gly Thr Leu Gly Lys Ala Phe Gly
        435                 440                 445

Cys Val Gly Gly Tyr Ile Ala Ser Thr Ser Ser Leu Ile Asp Thr Val
    450                 455                 460

Arg Ser Tyr Ala Ala Gly Phe Ile Phe Thr Thr Ser Leu Pro Pro Met
465                 470                 475                 480

Leu Leu Ala Gly Ala Leu Glu Ser Val Arg Ile Leu Lys Ser Ala Glu
                485                 490                 495

Gly Arg Val Leu Arg Arg Gln His Gln Arg Asn Val Lys Leu Met Arg
            500                 505                 510

Gln Met Leu Met Asp Ala Gly Leu Pro Val Val His Cys Pro Ser His
        515                 520                 525

Ile Ile Pro Val Arg Val Ala Asp Ala Ala Lys Asn Thr Glu Val Cys
    530                 535                 540

Asp Glu Leu Met Ser Arg His Asn Ile Tyr Val Gln Ala Ile Asn Tyr
545                 550                 555                 560

Pro Thr Val Pro Arg Gly Glu Glu Leu Leu Arg Ile Ala Pro Thr Pro
                565                 570                 575
```

```
His His Thr Pro Gln Met Met Asn Tyr Phe Leu Glu Asn Leu Leu Val
            580                 585                 590

Thr Trp Lys Gln Val Gly Leu Glu Leu Lys Pro His Ser Ser Ala Glu
        595                 600                 605

Cys Asn Phe Cys Arg Arg Pro Leu His Phe Glu Val Met Ser Glu Arg
    610                 615                 620

Glu Lys Ser Tyr Phe Ser Gly Leu Ser Lys Leu Val Ser Ala Gln Ala
625                 630                 635                 640


<210> SEQ ID NO 70
<211> LENGTH: 640
<212> TYPE: PRT
<213> ORGANISM: Homo sapiens

<400> SEQUENCE: 70

Met Glu Ser Val Val Arg Arg Cys Pro Phe Leu Ser Arg Val Pro Gln
1               5                   10                  15

Ala Phe Leu Gln Lys Ala Gly Lys Ser Leu Leu Phe Tyr Ala Gln Asn
            20                  25                  30

Cys Pro Lys Met Met Glu Val Gly Ala Lys Pro Ala Pro Arg Ala Leu
        35                  40                  45

Ser Thr Ala Ala Val His Tyr Gln Gln Ile Lys Glu Thr Pro Pro Ala
    50                  55                  60

Ser Glu Lys Asp Lys Thr Ala Lys Ala Lys Val Gln Gln Thr Pro Asp
65                  70                  75                  80

Gly Ser Gln Gln Ser Pro Asp Gly Thr Gln Leu Pro Ser Gly His Pro
                85                  90                  95

Leu Pro Ala Thr Ser Gln Gly Thr Ala Ser Lys Cys Pro Phe Leu Ala
            100                 105                 110

Ala Gln Met Asn Gln Arg Gly Ser Ser Val Phe Cys Lys Ala Ser Leu
        115                 120                 125

Glu Leu Gln Glu Asp Val Gln Glu Met Asn Ala Val Arg Lys Glu Val
    130                 135                 140

Ala Glu Thr Ser Ala Gly Pro Ser Val Val Ser Val Lys Thr Asp Gly
145                 150                 155                 160

Gly Asp Pro Ser Gly Leu Leu Lys Asn Phe Gln Asp Ile Met Gln Lys
                165                 170                 175

Gln Arg Pro Glu Arg Val Ser His Leu Leu Gln Asp Asn Leu Pro Lys
            180                 185                 190

Ser Val Ser Thr Phe Gln Tyr Asp Arg Phe Phe Glu Lys Lys Ile Asp
        195                 200                 205

Glu Lys Lys Asn Asp His Thr Tyr Arg Val Phe Lys Thr Val Asn Arg
    210                 215                 220

Arg Ala His Ile Phe Pro Met Ala Asp Asp Tyr Ser Asp Ser Leu Ile
225                 230                 235                 240

Thr Lys Lys Gln Val Ser Val Trp Cys Ser Asn Asp Tyr Leu Gly Met
                245                 250                 255

Ser Arg His Pro Arg Val Cys Gly Ala Val Met Asp Thr Leu Lys Gln
            260                 265                 270

His Gly Ala Gly Ala Gly Gly Thr Arg Asn Ile Ser Gly Thr Ser Lys
        275                 280                 285

Phe His Val Asp Leu Glu Arg Glu Leu Ala Asp Leu His Gly Lys Asp
    290                 295                 300

Ala Ala Leu Leu Phe Ser Ser Cys Phe Val Ala Asn Asp Ser Thr Leu
```

```
305                 310                 315                 320

Phe Thr Leu Ala Lys Met Met Pro Gly Cys Glu Ile Tyr Ser Asp Ser
                325                 330                 335

Gly Asn His Ala Ser Met Ile Gln Gly Ile Arg Asn Ser Arg Val Pro
            340                 345                 350

Lys Tyr Ile Phe Arg His Asn Asp Val Ser His Leu Arg Glu Leu Leu
        355                 360                 365

Gln Arg Ser Asp Pro Ser Val Pro Lys Ile Val Ala Phe Glu Thr Val
    370                 375                 380

His Ser Met Asp Gly Ala Val Cys Pro Leu Glu Glu Leu Cys Asp Val
385                 390                 395                 400

Ala His Glu Phe Gly Ala Ile Thr Phe Val Asp Glu Val His Ala Val
                405                 410                 415

Gly Leu Tyr Gly Ala Arg Gly Gly Gly Ile Gly Asp Arg Asp Gly Val
            420                 425                 430

Met Pro Lys Met Asp Ile Ile Ser Gly Thr Leu Gly Lys Ala Phe Gly
        435                 440                 445

Cys Val Gly Gly Tyr Ile Ala Ser Thr Ser Ser Leu Ile Asp Thr Val
    450                 455                 460

Arg Ser Tyr Ala Ala Gly Phe Ile Phe Thr Thr Ser Leu Pro Pro Met
465                 470                 475                 480

Leu Leu Ala Gly Ala Leu Glu Ser Val Arg Ile Leu Lys Ser Ala Glu
                485                 490                 495

Gly Arg Val Leu Arg Arg Gln His Gln Arg Asn Val Lys Leu Met Arg
            500                 505                 510

Gln Met Leu Met Asp Ala Gly Leu Pro Val Val His Cys Pro Ser His
        515                 520                 525

Ile Ile Pro Val Arg Val Ala Asp Ala Ala Lys Asn Thr Glu Val Cys
    530                 535                 540

Asp Glu Leu Met Ser Arg His Asn Ile Tyr Val Gln Ala Ile Asn Tyr
545                 550                 555                 560

Pro Thr Val Pro Arg Gly Glu Glu Leu Leu Arg Ile Ala Pro Thr Pro
                565                 570                 575

His His Thr Pro Gln Met Met Asn Tyr Phe Leu Glu Asn Leu Leu Val
            580                 585                 590

Thr Trp Lys Gln Val Gly Leu Glu Leu Lys Pro His Ser Ser Ala Glu
        595                 600                 605

Cys Asn Phe Cys Arg Arg Pro Leu His Phe Glu Val Met Ser Glu Arg
    610                 615                 620

Glu Lys Ser Tyr Phe Ser Gly Leu Ser Lys Leu Val Ser Ala Gln Ala
625                 630                 635                 640
```

<210> SEQ ID NO 71
<211> LENGTH: 17
<212> TYPE: DNA
<213> ORGANISM: Artificial Sequence
<220> FEATURE:
<223> OTHER INFORMATION: ALAS-1_forward primer

<400> SEQUENCE: 71
agccacatca tccctgt 17

<210> SEQ ID NO 72
<211> LENGTH: 22
<212> TYPE: DNA
<213> ORGANISM: Artificial Sequence
<220> FEATURE:
<223> OTHER INFORMATION: ALAS-1_reverse primer

<400> SEQUENCE: 72
cgtagatgtt atgtctgctc at 22

<210> SEQ ID NO 73
<211> LENGTH: 22
<212> TYPE: DNA
<213> ORGANISM: Artificial Sequence
<220> FEATURE:
<223> OTHER INFORMATION: ALAS-1 probe

<400> SEQUENCE: 73
tttagcagca tctgcaaccc gc 22

<210> SEQ ID NO 74
<211> LENGTH: 4543
<212> TYPE: DNA
<213> ORGANISM: Homo sapiens

<400> SEQUENCE: 74
atgcgtacgc tcgctggccc cgccccctag cgccgcggtc ggagccattt cgccgattcc 60
tccatgcgag ttgctgtgcg tttctctgtt gtctcggtag aaggccagag tcacacacgg 120
tcctaagagc tgggcaccag gaagcgaagg ctgatctgaa gaagacactt gaatcatggg 180
tgacgttaaa aattttctgt atgcctggtg tggcaaaagg aagatgaccc catcctatga 240
aattagagca gtggggaaca aaaacaggca gaaattcatg tgtgaggttc aggtggaagg 300
ttataattac actggcatgg gaaattccac caataaaaaa gatgcacaaa gcaatgctgc 360
cagagacttt gttaactatt tggttcgaat aaatgaaata aagagtgaag aagttccagc 420
ttttggggta gcatctccgc ccccacttac tgatactcct gacactacag caaatgctga 480
aggagattta ccaacaacca tgggaggacc tcttcctcca catctggctc tcaaagcaga 540
aaataattct gaggtagggg cctctggcta tggtgttcct gggcccacct gggaccgagg 600
agccaacttg aaggattact actcaagaaa ggaagaacaa gaagtgcaag cgactctaga 660
atcagaagaa gtggatttaa atgctgggct tcatggaaac tggaccttgg aaaatgctaa 720
agctcgtcta aaccaatatt ttcagaaaga aaagatccaa ggagaatata agtacaccca 780
agtgggtcct gatcacaaca ggagctttat tgcagaaatg accatttata tcaagcagct 840
gggcagaagg atttttgcac gagaacatgg atcaaataag aaattggcag cacagtcctg 900
tgccctgtca cttgtcagac aactgtacca tcttggagtg gttgaagctt actccggact 960
tacaaagaag aaggaaggag agacagtgga gccttacaaa gtaaacctct ctcaagattt 1020
agagcatcag ctgcaaaaca tcattcaaga gctaaatctt gagattttgc ccccgcctga 1080
agatccttct gtgccagttg cactcaacat tggcaaattg gctcagttcg aaccatctca 1140
gcgacaaaac caagtgggtg tggttccttg gtcacctcca caatccaact ggaatccttg 1200
gactagtagc aacattgatg aggggcctct ggcttttgct actccagagc aaataagcat 1260
ggacctcaag aatgaattga tgtaccagtt ggaacaggat catgatttgc aagcaatctt 1320
gcaggagaga gagttactgc ctgtgaagaa atttgaaagt gagattctgg aagcaatcag 1380
ccaaaattca gttgtcatta ttagaggggc tactggatgt gggaaaacca cacaggttcc 1440
ccagttcatt ctagatgact ttatccagaa tgaccgagca gcagagtgta acatcgtagt 1500
aactcagccc agaagaatca gtgcggtttc tgtggcagag cgagttgcat ttgaaagagg 1560

-continued agaagagcct ggaaaaagct gtggctacag cgttcgattt gagtctatac ttcctcgtcc 1620
tcatgccagt ataatgtttt gtactgtagg tgtgctcctg agaaaattag aagcaggcat 1680
tcgaggaatc agtcatgtaa ttgtagatga aatacatgaa agagatatta atactgactt 1740
ccttttggta gtactgcgtg atgttgttca ggcttatcct gaagttcgca ttgttcttat 1800
gtctgctact attgatacca gcatgttttg tgaatatttc ttcaattgcc ccatcattga 1860
agtttatggg aggacttacc cagttcaaga atattttctg gaagactgca ttcagatgac 1920
ccactttgtt cctccaccaa aagacaaaaa gaagaaggat aaggatgatg atggtggtga 1980
ggatgatgat gcaaattgca acttgatctg tggtgatgaa tatggtccag aaacaaggtt 2040
gagcatgtct caattgaacg aaaaggaaac tccttttgaa ctcatcgagg ctctacttaa 2100
gtacattgaa acccttaatg ttcctggagc tgtgttggtt tttttgcctg gctggaatct 2160
gatttatact atgcagaagc atttggaaat gaatccacat tttggaagcc atcggtatca 2220
gattctaccc ctgcattctc agattcctcg agaggaacag cgcaaagtgt ttgatccagt 2280
accagttgga gtaaccaagg ttattttgtc cacaaatatt gctgaaacaa gcattaccat 2340
aaacgatgtt gtttatgtca ttgactcctg caagcagaaa gtgaaactct tcactgctca 2400
caacaatatg accaactatg ctaccgtatg ggcatcaaaa acaaaccttg agcaacggaa 2460
agggcgagct ggccgagtac ggcctggatt ctgctttcac ctgtgcagcc gagctcgttt 2520
tgagagactt gaaacccaca tgacaccaga gatgttccga acaccattgc atgaaattgc 2580
tcttagcata aaacttctgc gtctaggagg aattggccaa tttctggcca aagcaattga 2640 acctcccccct ttggatgctg tgattgaagc agaacacact cttagagagc ttgatgcatt 2700
agatgccaat gatgagttga ctcctttggg acgaatcctg gctaaactcc ccattgagcc 2760
tcgttttggc aaaatgatga taatggggtg tattttctac gtgggagatg ctatctgtac 2820
cattgctgct gctacctgct ttccagagcc tttcatcaat gaaggaaagc ggctgggcta 2880
tatccatcga aattttgctg gaaacagatt ttctgatcac gtagcccttt tatcagtatt 2940
ccaagcctgg gatgatgcta gaatgggtgg agaagaagca gagatacgtt tttgtgagca 3000
caaaagactt aatatggcta cactaagaat gacctgggaa gccaaagttc agctcaaaga 3060
gattttgatt aattctgggt ttccagaaga ttgtttgttg acacaagtgt ttactaacac 3120
tggaccagat aataatttgg atgttgttat ctccctcctg gcctttggtg tgtaccccaa 3180
tgtatgctat cataaggaaa agaggaagat tctcaccact gaagggcgta atgcacttat 3240
ccacaaatca tctgttaatt gtccttttag tagccaagac atgaagtacc catctccctt 3300
ctttgtattt ggtgaaaaga ttcgaactcg agccatctct gctaaaggca tgactttagt 3360 caccccccctg cagttgcttc tctttgcctc caagaaagtc caatctgatg ggcagattgt 3420
gcttgtagat gactggatta aactgcaaat atctcatgaa gctgctgcct gtatcactgg 3480
tctccgggca gccatggagg ctttggttgt tgaagtaacc aaacaacctg ctatcatcag 3540
ccagttggac cccgtaaatg aacgtatgct gaacatgatc cgtcagatct ctagaccctc 3600
agctgctggt atcaacctta tgattggcag tacacggtat ggagatggtc cacgtcctcc 3660
caagatggcc cgatacgaca atggaagcgg atatagaagg ggaggttcta gttacagtgg 3720
tggaggctat ggcggtggct atagcagtgg aggctatggt agcggaggct atggtggcag 3780
cgccaactcc tttcgggcag gatatggtgc aggtgttggt ggaggctata gaggagtttc 3840
ccgaggtggc tttagaggca actctggagg agactacaga gggcctagtg gaggctacag 3900
aggatctggg ggattccagc gaggaggtgg tagggggggcc tatggaactg gctactttgg 3960
acagggaaga ggaggtggcg gctattaaaa cttggttatg tcagttcctg tgtgtagaca 4020
gtaaggaaaa aaaggcatgc tatgtgttac gtgtttttc cagtatgttt atttgccacc 4080
aaaaagtaaa tgcattttca cccattctgt ggttcattgt agtttaagga aaccaagcat 4140
atagatgcat tagtgatttt gtttatatta tgtaaaatat aacgatctct taaaaatacc 4200
acagtttgta ttttttcttt aaggagtaaa gatttgcctt taaataactt ggtattttcc 4260
tggctttcgt ttaatacaat agaaaataaa gtattacacc gaatacttgc cgtgtagttt 4320
gtttgttgac ctcgtatgtt agaaaatttt acaatgccag ctacatctgt tgattttaaa 4380
tgtcagagaa gttgtaccct gtttcaaaag tatactaagt gatactactt gtaatagaat 4440
aaatcatctt ggaattgaat tgttaccttt tgaagtaaat actggcaagt gcacaagcca 4500
cataaacctg aataaaactt ttgacctagg gttgaaaaaa aaa 4543

<210> SEQ ID NO 75
<211> LENGTH: 1270
<212> TYPE: PRT
<213> ORGANISM: Homo sapiens

<400> SEQUENCE: 75

Met Gly Asp Val Lys Asn Phe Leu Tyr Ala Trp Cys Gly Lys Arg Lys
1 5 10 15

Met Thr Pro Ser Tyr Glu Ile Arg Ala Val Gly Asn Lys Asn Arg Gln
20 25 30

Lys Phe Met Cys Glu Val Gln Val Glu Gly Tyr Asn Tyr Thr Gly Met
35 40 45

Gly Asn Ser Thr Asn Lys Lys Asp Ala Gln Ser Asn Ala Ala Arg Asp
50 55 60

Phe Val Asn Tyr Leu Val Arg Ile Asn Glu Ile Lys Ser Glu Glu Val
65 70 75 80

Pro Ala Phe Gly Val Ala Ser Pro Pro Pro Leu Thr Asp Thr Pro Asp
85 90 95

Thr Thr Ala Asn Ala Glu Gly Asp Leu Pro Thr Thr Met Gly Gly Pro
100 105 110

Leu Pro Pro His Leu Ala Leu Lys Ala Glu Asn Asn Ser Glu Val Gly
115 120 125

Ala Ser Gly Tyr Gly Val Pro Gly Pro Thr Trp Asp Arg Gly Ala Asn
130 135 140

Leu Lys Asp Tyr Tyr Ser Arg Lys Glu Glu Gln Glu Val Gln Ala Thr
145 150 155 160

Leu Glu Ser Glu Glu Val Asp Leu Asn Ala Gly Leu His Gly Asn Trp
165 170 175

Thr Leu Glu Asn Ala Lys Ala Arg Leu Asn Gln Tyr Phe Gln Lys Glu
180 185 190

Lys Ile Gln Gly Glu Tyr Lys Tyr Thr Gln Val Gly Pro Asp His Asn
195 200 205

Arg Ser Phe Ile Ala Glu Met Thr Ile Tyr Ile Lys Gln Leu Gly Arg
210 215 220

Arg Ile Phe Ala Arg Glu His Gly Ser Asn Lys Lys Leu Ala Ala Gln
225 230 235 240

Ser Cys Ala Leu Ser Leu Val Arg Gln Leu Tyr His Leu Gly Val Val
245 250 255

Glu Ala Tyr Ser Gly Leu Thr Lys Lys Lys Glu Gly Glu Thr Val Glu
260 265 270

```
Pro Tyr Lys Val Asn Leu Ser Gln Asp Leu Glu His Gln Leu Gln Asn
        275                 280                 285

Ile Ile Gln Glu Leu Asn Leu Glu Ile Leu Pro Pro Pro Glu Asp Pro
    290                 295                 300

Ser Val Pro Val Ala Leu Asn Ile Gly Lys Leu Ala Gln Phe Glu Pro
305                 310                 315                 320

Ser Gln Arg Gln Asn Gln Val Gly Val Val Pro Trp Ser Pro Pro Gln
                325                 330                 335

Ser Asn Trp Asn Pro Trp Thr Ser Ser Asn Ile Asp Glu Gly Pro Leu
            340                 345                 350

Ala Phe Ala Thr Pro Glu Gln Ile Ser Met Asp Leu Lys Asn Glu Leu
        355                 360                 365

Met Tyr Gln Leu Glu Gln Asp His Asp Leu Gln Ala Ile Leu Gln Glu
    370                 375                 380

Arg Glu Leu Leu Pro Val Lys Lys Phe Glu Ser Glu Ile Leu Glu Ala
385                 390                 395                 400

Ile Ser Gln Asn Ser Val Val Ile Ile Arg Gly Ala Thr Gly Cys Gly
                405                 410                 415

Lys Thr Thr Gln Val Pro Gln Phe Ile Leu Asp Asp Phe Ile Gln Asn
            420                 425                 430

Asp Arg Ala Ala Glu Cys Asn Ile Val Val Thr Gln Pro Arg Arg Ile
        435                 440                 445

Ser Ala Val Ser Val Ala Glu Arg Val Ala Phe Glu Arg Gly Glu Glu
    450                 455                 460

Pro Gly Lys Ser Cys Gly Tyr Ser Val Arg Phe Glu Ser Ile Leu Pro
465                 470                 475                 480

Arg Pro His Ala Ser Ile Met Phe Cys Thr Val Gly Val Leu Leu Arg
                485                 490                 495

Lys Leu Glu Ala Gly Ile Arg Gly Ile Ser His Val Ile Val Asp Glu
            500                 505                 510

Ile His Glu Arg Asp Ile Asn Thr Asp Phe Leu Leu Val Val Leu Arg
        515                 520                 525

Asp Val Val Gln Ala Tyr Pro Glu Val Arg Ile Val Leu Met Ser Ala
    530                 535                 540

Thr Ile Asp Thr Ser Met Phe Cys Glu Tyr Phe Phe Asn Cys Pro Ile
545                 550                 555                 560

Ile Glu Val Tyr Gly Arg Thr Tyr Pro Val Gln Glu Tyr Phe Leu Glu
                565                 570                 575

Asp Cys Ile Gln Met Thr His Phe Val Pro Pro Pro Lys Asp Lys Lys
            580                 585                 590

Lys Lys Asp Lys Asp Asp Asp Gly Gly Glu Asp Asp Asp Ala Asn Cys
        595                 600                 605

Asn Leu Ile Cys Gly Asp Glu Tyr Gly Pro Glu Thr Arg Leu Ser Met
    610                 615                 620

Ser Gln Leu Asn Glu Lys Glu Thr Pro Phe Glu Leu Ile Glu Ala Leu
625                 630                 635                 640

Leu Lys Tyr Ile Glu Thr Leu Asn Val Pro Gly Ala Val Leu Val Phe
                645                 650                 655

Leu Pro Gly Trp Asn Leu Ile Tyr Thr Met Gln Lys His Leu Glu Met
            660                 665                 670

Asn Pro His Phe Gly Ser His Arg Tyr Gln Ile Leu Pro Leu His Ser
        675                 680                 685
```

-continued

```
Gln Ile Pro Arg Glu Glu Gln Arg Lys Val Phe Asp Pro Val Pro Val
    690                 695                 700

Gly Val Thr Lys Val Ile Leu Ser Thr Asn Ile Ala Glu Thr Ser Ile
705                 710                 715                 720

Thr Ile Asn Asp Val Val Tyr Val Ile Asp Ser Cys Lys Gln Lys Val
                725                 730                 735

Lys Leu Phe Thr Ala His Asn Asn Met Thr Asn Tyr Ala Thr Val Trp
            740                 745                 750

Ala Ser Lys Thr Asn Leu Glu Gln Arg Lys Gly Arg Ala Gly Arg Val
        755                 760                 765

Arg Pro Gly Phe Cys Phe His Leu Cys Ser Arg Ala Arg Phe Glu Arg
    770                 775                 780

Leu Glu Thr His Met Thr Pro Glu Met Phe Arg Thr Pro Leu His Glu
785                 790                 795                 800

Ile Ala Leu Ser Ile Lys Leu Leu Arg Leu Gly Gly Ile Gly Gln Phe
                805                 810                 815

Leu Ala Lys Ala Ile Glu Pro Pro Pro Leu Asp Ala Val Ile Glu Ala
            820                 825                 830

Glu His Thr Leu Arg Glu Leu Asp Ala Leu Asp Ala Asn Asp Glu Leu
        835                 840                 845

Thr Pro Leu Gly Arg Ile Leu Ala Lys Leu Pro Ile Glu Pro Arg Phe
    850                 855                 860

Gly Lys Met Met Ile Met Gly Cys Ile Phe Tyr Val Gly Asp Ala Ile
865                 870                 875                 880

Cys Thr Ile Ala Ala Ala Thr Cys Phe Pro Glu Pro Phe Ile Asn Glu
                885                 890                 895

Gly Lys Arg Leu Gly Tyr Ile His Arg Asn Phe Ala Gly Asn Arg Phe
            900                 905                 910

Ser Asp His Val Ala Leu Leu Ser Val Phe Gln Ala Trp Asp Asp Ala
        915                 920                 925

Arg Met Gly Gly Glu Glu Ala Glu Ile Arg Phe Cys Glu His Lys Arg
    930                 935                 940

Leu Asn Met Ala Thr Leu Arg Met Thr Trp Glu Ala Lys Val Gln Leu
945                 950                 955                 960

Lys Glu Ile Leu Ile Asn Ser Gly Phe Pro Glu Asp Cys Leu Leu Thr
                965                 970                 975

Gln Val Phe Thr Asn Thr Gly Pro Asp Asn Asn Leu Asp Val Val Ile
            980                 985                 990

Ser Leu Leu Ala Phe Gly Val Tyr  Pro Asn Val Cys Tyr  His Lys Glu
        995                 1000                1005

Lys Arg  Lys Ile Leu Thr Thr  Glu Gly Arg Asn Ala  Leu Ile His
    1010                1015                1020

Lys Ser  Ser Val Asn Cys Pro  Phe Ser Ser Gln Asp  Met Lys Tyr
    1025                1030                1035

Pro Ser  Pro Phe Phe Val Phe  Gly Glu Lys Ile Arg  Thr Arg Ala
    1040                1045                1050

Ile Ser  Ala Lys Gly Met Thr  Leu Val Thr Pro Leu  Gln Leu Leu
    1055                1060                1065

Leu Phe  Ala Ser Lys Lys Val  Gln Ser Asp Gly Gln  Ile Val Leu
    1070                1075                1080

Val Asp  Asp Trp Ile Lys Leu  Gln Ile Ser His Glu  Ala Ala Ala
    1085                1090                1095

Cys Ile  Thr Gly Leu Arg Ala  Ala Met Glu Ala Leu  Val Val Glu
```

-continued

```
    1100                1105                1110

Val Thr  Lys Gln Pro Ala Ile  Ile Ser Gln Leu Asp  Pro Val Asn
    1115                1120                1125

Glu Arg  Met Leu Asn Met Ile  Arg Gln Ile Ser Arg  Pro Ser Ala
    1130                1135                1140

Ala Gly  Ile Asn Leu Met Ile  Gly Ser Thr Arg Tyr  Gly Asp Gly
    1145                1150                1155

Pro Arg  Pro Pro Lys Met Ala  Arg Tyr Asp Asn Gly  Ser Gly Tyr
    1160                1165                1170

Arg Arg  Gly Gly Ser Ser Tyr  Ser Gly Gly Gly Tyr  Gly Gly Gly
    1175                1180                1185

Tyr Ser  Ser Gly Gly Tyr Gly  Ser Gly Gly Tyr Gly  Gly Ser Ala
    1190                1195                1200

Asn Ser  Phe Arg Ala Gly Tyr  Gly Ala Gly Val Gly  Gly Gly Tyr
    1205                1210                1215

Arg Gly  Val Ser Arg Gly Gly  Phe Arg Gly Asn Ser  Gly Gly Asp
    1220                1225                1230

Tyr Arg  Gly Pro Ser Gly Gly  Tyr Arg Gly Ser Gly  Gly Phe Gln
    1235                1240                1245

Arg Gly  Gly Gly Arg Gly Ala  Tyr Gly Thr Gly Tyr  Phe Gly Gln
    1250                1255                1260

Gly Arg  Gly Gly Gly Gly Tyr
    1265                1270
```

PRE-SURGICAL RISK STRATIFICATION BASED ON PDE4D7 AND DHX9 EXPRESSION

CROSS-REFERENCE TO PRIOR APPLICATIONS

This application is the U.S. National Phase application under 35 U.S.C. § 371 of International Application No. PCT/EP2019/077549, filed on Oct. 11, 2019, which claims the benefit of European Patent Application No. 18199784.2, filed on Oct. 11, 2018. These applications are hereby incorporated by reference herein.

FIELD OF THE INVENTION

The invention relates to a method of pre-surgical risk stratification of a prostate cancer subject. Moreover, the invention relates to a diagnostic kit, to a use of the diagnostic kit in a method of pre-surgical risk stratification of a prostate cancer subject, to a use of a gene expression profile for phosphodiesterase 4D variant 7 (PDE4D7) and a gene expression profile for DExH-box helicase 9 (DHX9) in pre-surgical risk stratification of a prostate cancer subject, and to a corresponding computer program product.

BACKGROUND OF THE INVENTION

Cancer is a class of diseases in which a group of cells displays uncontrolled growth, invasion and sometimes metastasis. These three malignant properties of cancers differentiate them from benign tumors, which are self-limited and do not invade or metastasize. Prostate Cancer (PCa) is the most commonly-occurring non-skin malignancy in men, with an estimated 1.1 million new cases diagnosed world-wide in 2012 (see Ferlay J. et al., GLOBOCAN 2012 v1.0, Cancer Incidence and Mortality Worldwide: IARC CancerBase No. 11 [Internet], Lyon, France, International Agency for Research on Cancer, 2013).

Due to ageing populations, the incidence of PCa will further increase in the coming years (see Quon H. et al., "Dramatic increase in prostate cancer cases by 2021", BJU International, Vol. 108, No. 11, pages 1734 to 1738, 2011). Routine diagnosis by determination of blood levels of the prostate-specific antigen (PSA), digital rectal exam (DRE) and transrectal ultrasound analysis (TRUS) leads to significant first-line over-diagnosis of non-cancerous, benign prostate conditions (see Bangma C.H. et al., "Overdiagnosis and overtreatment of early detected prostate cancer", World Journal of Urology, Vol. 25, No. 1, pages 3 to 9, 2007, and Schroder F.H. et al., "Screening and Prostate-Cancer Mortality in a Randomized European Study", The New England Journal of Medicine, Vol. 360, No. 13, pages 1320 to 1328, 2009): of the approximately 1 million prostate biopsies annually performed in the U.S. alone to find about 250,000 new cases, about 75% are done unnecessarily, incurring both substantial complications (urosepsis, bleedings, urinary retention) in patients and total cost of >USD 2 billion (~USD 2,100 per biopsy procedure). At least 4 out of 100 men with a negative biopsy are likely to be hospitalized due to side-effects and 9 out of 10,000 biopsied patients are at risk of dying from the currently used procedure (see Nam R.K. et al., "Increasing hospital admission rates for urological complications after transrectal ultrasound guided biopsy", Journal of Urology, Vol. 183, No. 3, pages 963 to 968, 2010).

Of the approximately 250,000 newly detected PCa cases in the U.S. per year, about 200,000 are initially characterized as localized disease (see Snyder C.F. et al., "How does initial treatment choice affect short-term and long-term costs for clinically localized prostate cancer?", Cancer, Vol. 116, No. 23, pages 5391 to 5399, 2010, and Cooperberg M. R. et al., "Contemporary trends in low risk prostate cancer: risk assessment and treatment", Journal of Urology, Vol. 173, No. 3, Pt. 2, pages 14 to 19, 2007), i.e. as cancer confined to the prostate organ. This condition is to a certain extent curable by primary treatment approaches, such as radiation therapy or, in particular, the partial or total removal of the prostate by surgery (prostatectomy). However, these interventions typically come with serious side effects, particularly urinary incontinence and/or erectile dysfunctions as very frequent consequences of prostatectomy. Up to 50% of men undergoing radical prostatectomy develop urinary incontinence. Studies have shown that, one year after surgery, between 15% and 50% of men still report such problems. Erection problems likewise are serious side effects of radical prostatectomy (RP). Only about half of the operated men are able to regain some of their ability to have erections. Furthermore, all routinely applied treatments for localized PCa are expensive (typically in the order of USD 20-30,000) and incur total direct costs of USD 5 billion in the U.S. each year.

Among the 200,000 men in the United States with clinically localized disease at diagnosis, up to 50% have very-low- or low-risk cancer (see Bangma C. H. and Roobol M. J., "Defining and predicting indolent and low prostate cancer", Critical Reviews in Oncology/Hematology, Vol. 83, No. 2, pages 235 to 241, 2012). Accordingly, the NCCN (National Comprehensive Cancer Network) recently revised their PCa treatment guidelines to expand active surveillance (AS) as a gentle and convenient treatment alternative for patients with such low risk disease (see www.nccn.org). By referring appropriate patients to AS, the quality of life for such patients is significantly improved as compared with men having undergone primary treatment and the 5-year cost for AS is reported to be less than USD 10,000 per patient (see Snyder C. F. et al.).

Moreover, in case surgery (vs. AS) is selected as the treatment of choice for a given patient, it is of significant advantage to stratify for the extent of surgery according to the potential aggressiveness of the patient's tumor. For instance, nerve-sparing operation techniques could be more generally applied for men with predicted low-risk disease to minimize potency-related adverse effects of radical prostatectomy. Likewise, according to the European Association of Urology (EAU)'s latest Prostate Cancer Guidelines, extended lymph node dissection is recommended in case of a predicted high-risk cancer despite the fact that the procedure is complex, time-consuming and associated with higher complication rates as compared with more limited procedures (see Heidenreich A. et al., "Guidelines on Prostate Cancer", European Association of Urology, 2012). Consequently, while less limited lymph node dissection has shown to miss about 50% of lymph node metastases (see Heidenreich A. et al., "Extended pelvic lymphadenectomy in patients undergoing radical prostatectomy: high incidence of lymph node metastasis", Journal of Urology, Vol. 167, No. 4, pages 1681 to 1686, 2002, and Bader P. et al, "Is a limited lymph node dissection and adequate staging procedure for prostate cancer?", Journal of Urology, Vo. 168, No. 2, pages 514 to 518, 2002), the management of men with localized prostate cancer requires highly accurate pre-surgical predictions of the aggressiveness potential of an individual tumor to provide most optimal care for each patient.

WO 2014/028884 A2 discloses methods, systems and kits for the diagnosis, prognosis and determination of cancer progression of a cancer in a subject. Further disclosed are methods, systems and kits for determining the treatment modality of a cancer in a subject. The methods, systems and kits comprise expression-based analysis of biomarkers. Further disclosed are probe sets for use in assessing a cancer status in a subject.

SUMMARY OF THE INVENTION

It is an object of the invention to provide a method of pre-surgical risk stratification of a prostate cancer subject, which may allow making better pre-surgical predictions of the aggressiveness potential of an individual tumor. It is a further object of the invention to provide a diagnostic kit, a use of the diagnostic kit in a method of pre-surgical risk stratification of a prostate cancer subject, a use of a gene expression profile for phosphodiesterase 4D variant 7 (PDE4D7) and a gene expression profile for DExH-box helicase 9 (DHX9) in pre-surgical risk stratification of a prostate cancer subject, and a corresponding computer program product.

In a first aspect of the present invention, a method of pre-surgical risk stratification of a prostate cancer subject is presented, comprising:

determining a gene expression profile for phosphodiesterase 4D variant 7 (PDE4D7) in a biological sample obtained from the subject, determining a gene expression profile for DExH-box helicase 9 (DHX9) in the same or another biological sample obtained from the subject, and determining a pre-surgical prognostic risk score for the subject based on the gene expression profile for PDE4D7 and the gene expression profile for DHX9.

The cAMP signaling pathway is known to play an important role in both the development and progression of prostate cancer (see Merkle D. and Hoffmann R., "Roles of cAMP and cAMP-dependent protein kinase in the progression of prostate cancer: Cross-talk with the androgen receptor", Cellular Signalling, Vol. 23, No. 3, pages 507-515, 2011).

While a family of adenylate cyclases is responsible for the synthesis of cAMP, cyclic nucleotide phosphodiesterases (PDEs) appear to represent the only cellular mechanism for its destruction. PDEs provide both signal termination and, importantly, the compartmentalization of cAMP signaling within the 3D matrix of cells. This is achieved through the spatially discrete destruction of cAMP via sub-populations of distinct PDE isoforms sequestered by localized anchor proteins/signalosomes (see, for example, Conti M. and Beavo J., "Biochemistry and physiology of cyclic nucleotide phosphodiesterases: essential components in cyclic nucleotide signaling", Annual Review of Biochemistry, Vol. 76, pages 481-511, 2007). Thus changes in the expression and/or activity of distinct PDE isoforms can alter downstream signaling pathways during disease development and progression, providing potential targets for novel biomarkers and for targeted therapeutic intervention. Indeed, alterations in the expression of members of the cAMP-degrading PDE4 family appear to be associated with a number of different diseases, including stroke, acrodysostosis, schizophrenia, and COPD. Recently, it was shown that downregulation of a particular PDE4 isoform (PDE4D7) may have an impact on prostate cancer (see, for example, Böttcher R. et al., "Human phosphodiesterase 4D7 (PDE4D7) expression is increased in TMPRSS2-ERG positive primary prostate cancer and independently adds to a reduced risk of post-surgical disease progression", British Journal of Cancer, Vol. 113, No. 10, pages 1502-1511, 2015). PDE4D7 isoform is a so-called long isoform as it contains both the UCR1 and UCR2 regulatory domains. UCR1 is found in long, but not short, PDE4 isoforms and allows for regulation by various protein kinases, including PKA and MK2 and also determines the functional outcome of catalytic unit phosphorylation by ERK. Functionally, it provides part of the cellular desensitization system to cAMP and enables cross-talk between signaling pathways that lead to the activation of ERK and AMPK, for example.

Emerging evidence demonstrates that human helicases like DHX9 could act as hubs in the cellular networks to coordinate cellular stress responses to maintain cellular homeostasis for survival or to trigger cell death. Interestingly, it has recently been shown that a range of human cancer cell lines are susceptive to suppression of DHX9 helicase activity in vitro and in vivo. Gene expression profiling of tumor cells after DHX9 suppression revealed the de-regulation of a range of pathways involved in tumor development or progression. Further, DHX9 has lately been described as a major player in resolving R-loop-associated DNA damage which supports maintenance of genomic stability. Disruption of this process may lead to cancer development and progression due to rearrangements on the genomic level, a phenomenon that has been demonstrated in many cancers. These recent findings are very much supported by data created by the inventors, which show a significant association of DHX9 gene expression to time to prostate cancer relapse in a clinical prostate cancer patient cohort with longitudinal follow-up (unpublished data).

The inventors have identified and confirmed an interaction between PDE4D7 and the helicase DHX9 in prostate cancer cells. In addition, it could be shown that the N-terminal domain of DHX9 is phosphorylated in vitro by cAMP-dependent protein kinase A (PKA). This raises the question whether this post-translation modification by PKA has any regulatory influence on the activity or cellular localization of DHX9 and whether the interaction with PDE4D7 affects the phosphorylation by regulating cyclic AMP in the micro-domain of DHX9. By this, PDE4D7 as newly identified interactor of DHX9 might play a crucial role in controlling directly or indirectly the function of DHX9 in prostate cancer development.

By determining a pre-surgical prognostic risk score for a prostate cancer subject based on the gene expression profiles for both PDE4D7 and DHX9, additional molecular information representing the biology of the disease is obtained. The prognostic power of PDE4D7 and DHX9 is utilized in pre-surgical patient risk assessment by determining a pre-surgical prognostic risk score that is based on the gene expression profiles for both PDE4D7 and DHX9. This may allow for an improved stratification of the subject in a pre-surgical setting that may result in better primary treatment decisions. For instance, the pre-surgical prognostic risk score may allow to make better recommendations on whether to select active surveillance vs. active intervention, e.g., radical prostatectomy, for certain sub-populations of prostate cancer patients.

The term "phosphodiesterase 4D7" or "PDE4D7" refers to the splice variant 7 of the human phosphodiesterase PDE4D, i.e., the human phosphodiesterase PDE4D7 gene, for example, to the sequence as defined in NCBI Reference Sequence: NM_001165899.1, specifically, to the nucleotide sequence as set forth in SEQ ID NO:19, which corresponds to the sequence of the above indicated NCBI Reference Sequence of the PDE4D7 transcript, and also relates to the corresponding amino acid sequence for example as set forth in SEQ ID NO:20, which corresponds to the protein sequence defined in NCBI Protein Accession Reference Sequence NP_001159371.1 encoding the PDE4D7 polypeptide. The term "phosphodiesterase 4D7" or "PDE4D7" also relates to the amplicon that can be generated by the primer pair PDE4D7_forward (SEQ ID NO:21) and the PDE4D7_reverse (SEQ ID NO:22) and can be detected by probe SEQ ID NO:23.

The PDE4D7 polypeptide can also be detected with primer pair PDE4D7-2_forward (SEQ ID NO:24) and the PDE4D7_reverse (SEQ ID NO:25) and can be detected by probe SEQ ID NO:26.

The term "PDE4D7" also comprises nucleotide sequences showing a high degree of homology to PDE4D7, e.g., nucleic acid sequences being at least 75%, 80%, 85%, 90%, 91%, 92%, 93%, 94%, 95%, 96%, 97%, 98% or 99% identical to the sequence as set forth in SEQ ID NO:19 or amino acid sequences being at least 75%, 80%, 85%, 90%, 91%, 92%, 93%, 94%, 95%, 96%, 97%, 98% or 99% identical to the sequence as set forth in SEQ ID NO:20 or nucleic acid sequences encoding amino acid sequences being at least 75%, 80%, 85%, 90%, 91%, 92%, 93%, 94%, 95%, 96%, 97%, 98% or 99% identical to the sequence as set forth in SEQ ID NO:20 or amino acid sequences being encoded by nucleic acid sequences being at least 75%, 80%, 85%, 90%, 91%, 92%, 93%, 94%, 95%, 96%, 97%, 98% or 99% identical to the sequence as set forth in SEQ ID NO:19.

The term "DExH-box helicase 9" or "DHX9" refers to refers to the human DExH-box helicase 9 gene, for example, to the sequence as defined in NCBI Reference Sequence: NM_001357.4 (Ensembl: ENSG00000135829), specifically, to the nucleotide sequence as set forth in SEQ ID NO:74, which corresponds to the sequence of the above indicated NCBI Reference Sequence of the DHX9 transcript, and also relates to the corresponding amino acid sequence for example as set forth in SEQ ID NO:75, which corresponds to the protein sequence defined in NCBI Protein Accession Reference Sequence NP_001348.2 encoding the DHX9 polypeptide.

The term "DHX9" also comprises nucleotide sequences showing a high degree of homology to DHX9, e.g., nucleic acid sequences being at least 75%, 80%, 85%, 90%, 91%, 92%, 93%, 94%, 95%, 96%, 97%, 98% or 99% identical to the sequence as set forth in SEQ ID NO:74 or amino acid sequences being at least 75%, 80%, 85%, 90%, 91%, 92%, 93%, 94%, 95%, 96%, 97%, 98% or 99% identical to the sequence as set forth in SEQ ID NO:75 or nucleic acid sequences encoding amino acid sequences being at least 75%, 80%, 85%, 90%, 91%, 92%, 93%, 94%, 95%, 96%, 97%, 98% or 99% identical to the sequence as set forth in SEQ ID NO:75 or amino acid sequences being encoded by nucleic acid sequences being at least 75%, 80%, 85%, 90%, 91%, 92%, 93%, 94%, 95%, 96%, 97%, 98% or 99% identical to the sequence as set forth in SEQ ID NO:74.

The term "biological sample" or "sample obtained from a subject" refers to any biological material obtained via suitable methods known to the person skilled in the art from a subject, e.g., a prostate cancer patient. The biological sample used may be collected in a clinically acceptable manner, e.g., in a way that nucleic acids (in particular RNA) or proteins are preserved.

The biological sample(s) may include body tissue and/or a fluid, such as, but not limited to, blood, sweat, and urine. Furthermore, the biological sample may contain a cell extract derived from or a cell population including an epithelial cell, such as a cancerous epithelial cell or an epithelial cell derived from tissue suspected to be cancerous. The biological sample may contain a cell population derived from a glandular tissue, e.g., the sample may be derived from the prostate of a male subject. Additionally, cells may be purified from obtained body tissues and fluids if necessary, and then used as the biological sample. In some realizations, the sample may be a tissue sample, a urine sample, a urine sediment sample, a blood sample, a saliva sample, a semen sample, a sample including circulating tumor cells, extracellular vesicles, a sample containing prostate secreted exosomes, or cell lines or cancer cell line.

In one particular realization, biopsy or resections samples may be obtained and/or used. Such samples may include cells or cell lysates.

It is also conceivable that the content of a biological sample is submitted to an enrichment step. For instance, a sample may be contacted with ligands specific for the cell membrane or organelles of certain cell types, e.g., prostate cells, functionalized for example with magnetic particles. The material concentrated by the magnetic particles may subsequently be used for detection and analysis steps as described herein above or below.

Furthermore, cells, e.g., tumor cells, may be enriched via filtration processes of fluid or liquid samples, e.g., blood, urine, etc. Such filtration processes may also be combined with enrichment steps based on ligand specific interactions as described herein above.

The term "prostate cancer" refers to a cancer of the prostate gland in the male reproductive system, which occurs when cells of the prostate mutate and begin to multiply out of control. Typically, prostate cancer is linked to an elevated level of prostate-specific antigen (PSA). In one embodiment of the present invention the term "prostate cancer" relates to a cancer showing PSA levels above 4.0. In another embodiment the term relates to cancer showing PSA levels above 2.0. The term "PSA level" refers to the concentration of PSA in the blood in ng/ml. The term "non-progressive prostate cancer state" means that a sample of an individual does not show parameter values indicating "biochemical recurrence" and/or "clinical recurrence".

The term "progressive prostate cancer state" means that a sample of an individual shows parameter values indicating "biochemical recurrence" and/or "clinical recurrence".

The term "biochemical recurrence" generally refers to recurrent biological values of increased PSA indicating the presence of prostate cancer cells in a sample. However, it is also possible to use other markers that can be used in the detection of the presence or that rise suspicion of such presence.

The term "clinical recurrence" refers to the presence of clinical signs indicating the presence of tumor cells as measured, for example using in vivo imaging.

The term "prognosticating prostate cancer" as used herein refers to the prediction of the course or outcome of a diagnosed or detected prostate cancer, e.g., during a certain period of time, during a treatment or after a treatment. The term also refers to a determination of chance of survival or recovery from the disease, as well as to a prediction of the expected survival time of a subject. A prognosis may, specifically, involve establishing the likelihood for survival of a subject during a period of time into the future, such as 6 months, 1 year, 2 years, 3 years, 5 years, 10 years or any other period of time.

It is preferred that the gene expression profile for PDE4D7 and the gene expression profile for DHX9 are combined with a regression function that had been derived from a population of prostate cancer subjects.

Regression analysis helps one understand how the typical value of the dependent variable (or "criterion variable") changes when any one of the independent variables is varied, while the other independent variables are held fixed. This relationship between the dependent variable and the independent variables is captured in the regression function, which can be used to predict the dependent variable given the values of the independent variables. The dependent variable can be, for example, a binary variable, such as biochemical recurrence within 5 years after surgery. In this case, the regression is a logistic regression that is based on a logit function of the independent variables, which, here, comprise or consist of the gene expression profile for PDE4D7 and the gene expression profile for DHX9. By means of the regression function, an improved prediction of e.g. the 5-year risk of biochemical recurrence after surgery may be possible.

It is preferred that the method further comprises:

proposing a primary treatment for the subject based on the pre-surgical prognostic risk score, wherein the primary treatment is selected from the group consisting of: (i) at least a partial prostatectomy; (ii) an active therapy selected from radiation treatment, hormone therapy, chemotherapy, and a combination thereof; and (iii) active surveillance.

The various national and international guidelines recommend different treatments for a prostate cancer subject depending on the risk of future disease progression and life expectancy. For example, for men with very low and low risk prostate cancer active surveillance (AS) is generally recommended, whereas for high risk cancer a radical prostatectomy could be indicated. However, the known clinical risk descriptors do not delineate effectively either the extent of the disease or its aggressiveness for all patients. For instance, it has been found that in the National Comprehensive Cancer Network (NCCN) very low and low risk groups, there is a significant sub-group of patients population with a risk of 10 to 25% cancer recurrence after primary treatment. Likewise, it is known that in the intermediate risk group there is a sub-population with low risk of biochemical progression. By basing the proposing of a primary treatment for the subject on the pre-surgical prognostic risk score, better recommendations on e.g. whether to select active surveillance vs. active intervention, e.g., radical prostatectomy, may be made for certain sub-populations of prostate cancer patients.

It is further preferred that the method comprises:

normalizing the gene expression profile for PDE4D7 and/or the gene expression profile for DHX9 with respect to one or more reference genes selected from the group consisting of: *Homo sapiens* hypoxanthine phosphoribosyltransferase 1 (HPRT1), Tubulin-Alpha-1b (TUBA1B), *Homo sapiens* pumilio RNA-Binding Family Member (PUM1), and *Homo sapiens* TATA box binding protein (TBP), wherein the pre-surgical prognostic risk score is determined based on the normalized gene expression profile(s).

By normalizing the gene expression profile(s) with respect to one or more reference genes and by determining the pre-surgical prognostic risk score based on the normalized gene expression profile(s), variability in the determination of the pre-surgical prognostic risk score can be reduced. This enables differentiation between real variations in gene expression profiles and variations due to the measurement processes. In this respect, it has been found that HPRT1, TUBA1B, PUM1, and TBP are particularly well suited as reference genes for normalizing the PDE4D7 and/or DHX9 gene expression profile(s).

The gene expression profile(s) may be determined by detecting mRNA expression using one or more primers and/or probes and/or one or more sets thereof. Moreover, the gene expression profile(s) may be determined by an amplification based method and/or microarray analysis and/or RNA sequencing. The determining of the gene expression profile(s) may include performing Real-Time Quantitative Polymerase Chain Reaction (RT-qPCR) on RNA extracted from the biological sample. In other embodiments, the gene expression profile(S) are determined by RNA sequencing, conventional PCR (using, e.g., end point analysis by gel electrophoresis), or multiplex-PCR. In the case of RT-qPCR, the determining of the gene expression profile(s) may include determining a threshold cycle (Ct) value for PDE4D7 and/or DHX9 and each of the one or more reference genes. The PCR may be performed with at least one primer and/or probe for measuring a reference gene selected from HPRT1, TUBA1B, PUM1, and TBP. It is preferred that the one or more reference genes comprise at least two, or at least three, or all of HPRT1, TUBA1B, PUM1, and TBP.

Other reference genes which may be additionally or alternatively used for normalizing the PDE4D7 and/or DHX9 gene expression profile(s) include: *Homo sapiens* actin, beta, mRNA (ACTB); *Homo sapiens* 60S acidic ribosomal phosphoprotein P0 mRNA (RPLP0); Polymerase (RNA) II (DNA Directed) Polypeptide A, 220kDa (POLR2A); Beta-2-Microglobulin (B2M); and Aminolevulinate-Delta-Synthase (ALAS-1).

In some preferred embodiments, the normalized gene expression profile(s) for PDE4D7 and/or DHX9 are transformed to a predefined range of values, for example, a range of 1 to 5, using (a) suitable transform function(s). The transform function(s) has/have preferably been derived from the correspondingly normalized gene expression profile(s) e.g., the gene expression profile(s) normalized with respect to all of HPRT1, TUBA1B, PUM1, and TBP, for PDE4D7 and/or for DHX9, for biological samples derived from a population of prostate cancer subjects (which advantageously may be the same population as employed for deriving the regression function). In one preferred realization, a transform function can be a linear transformation that transform the normalized gene expression profile into the predefined range of values. Such a transformation can be determined by considering the frequency distribution of the normalized gene expression profile values for e.g. PDE4D7 (or for DHX9) for the biological samples of the population of prostate cancer subjects and by determining the transformation that transforms the frequency distribution into the desired range. By making use of such a transform function, the gene expression profile can be expressed in a way that is intuitive to a user, such as in a small positive value range. This is similar to other categories used in the clinical routine, e.g., in histo-pathology grading (Gleason) or multi-parametric MRI radiology scoring (PIRADS). In one particular realization, the transformed normalized gene expression profile is determined as follows:

$$\text{TNGEP}=(((\text{GENE\_norm}+A)*B)+1), \quad (1)$$

where "TNGEP" is the transformed normalized gene expression profile, "GENE_norm" is the normalized PDE4D7 or DHX9 gene expression profile value, and A and B are variables and are suitably chosen to map "GENE_norm" to the desired value range.

It is particularly preferred that the determining of the gene expression profile for PDE4D7 and/or the gene expression profile for DHX9 comprises performing RT-qPCR on RNA extracted from the biological sample(s), wherein a Cq value is determined for PDE4D7 and/or DHX9 and for each of the one or more reference genes, and wherein the determining of the pre-surgical risk score includes normalizing the Cq value for PDE4D7 and/or DHX9 using the Cq value for each of the one or more reference genes and computing the pre-surgical risk score based on the normalized Cq value(s).

For example, the normalized Cq value for PDE4D7 may be generated by applying the following:

$$N(Cqp_{PDE4D7})=Mean(Cq_{ref\_genes})-(Cq_{PDE4D7}), \qquad (2)$$

where $N(Cq_{PDE4D7})$ is the normalized genes expression profile value (quantification cycle, Cq) of PDE4D7, Mean $(Cq_{ref\_genes})$ is the arithmetic mean of the PCR Cq values of the one or more reference gene, and $Cq_{PDE4D7}$ is the PCR Cq value of PDE4D7. Likewise, the normalized Cq value for DHX9 may be generated by applying the following:

$$N(Cq_{DHX}9)=Mean(Cq_{ref\_genes})-(Cq_{DHX9}), \qquad (3)$$

where $N(Cq_{DHX9})$ is the normalized genes expression profile value (quantification cycle, Cq) of DHX9, $Mean(Cq_{ref\_genes})$ is the arithmetic mean of the PCR Cq values of the one or more reference gene, and $Cq_{DHX9}$ is the PCR Cq value of DHX9.

In a further aspect of the present invention, a diagnostic kit is presented, comprising:

at least one primer and/or probe for determining the gene expression profile for phosphodiesterase 4D variant 7 (PDE4D7) in a biological sample obtained from a prostate cancer subject;

at least one primer and/or probe for determining the gene expression profile for DExH-box helicase 9 (DHX9) in the same or another biological sample obtained from the subject; and optionally, at least one primer and/or probe for determining the gene expression profile for one or more reference genes selected from the group consisting of: *Homo sapiens* hypoxanthine phosphoribosyltransferase 1 (HPRT1), Tubulin-Alpha-1b (TUBA1B) *Homo sapiens* pumilio RNA-Binding Family Member (PUM1), and *Homo sapiens* TATA box binding protein (TBP);

wherein the diagnostic kit further comprises instructions for computing a pre-surgical prognostic risk score based on the gene expression profile for PDE4D7 and the gene expression profile for DHX9, the instructions being stored on a computer program product which, when executed by a computer, perform a method comprising:

determining the pre-surgical prognostic risk score for the subject based on the gene expression profile for PDE4D7 and the gene expression profile for DHX9 optionally, wherein the method comprises:

normalizing the gene expression profile for PDE4D7 and/or the gene expression profile for DHX9 with respect to the one or more reference genes, wherein the pre-surgical prognostic risk score is determined based on the normalized gene expression profile(s).

It is preferred that the instructions for computing the pre-surgical prognostic risk score comprise instructions for combining the gene expression profile for PDE4D7 and the gene expression profile for DHX9 with a regression function that had been derived from a population of prostate cancer subjects.

In a further aspect of the present invention, a use of the diagnostic kit as defined in claim 7 or 8 in a method of pre-surgical risk stratification of a prostate cancer subject is presented.

In a further aspect of the present invention, a use of a gene expression profile for phosphodiesterase 4D variant 7 (PDE4D7) and a gene expression profile for DExH-box helicase 9 (DHX9) in pre-surgical risk stratification of a prostate cancer subject is presented, comprising:

determining the gene expression profile for PDE4D7 in a biological sample obtained from the subject, determining the gene expression profile for DHX9 in the same or another biological sample obtained from the subject, and determining a pre-surgical prognostic risk score for the subject based on the gene expression profile for PDE4D7 and the gene expression profile for DHX9.

It is preferred that the gene expression profile for PDE4D7 and the gene expression profile for DHX9 are combined with a regression function that had been derived from a population of prostate cancer subjects.

In a further aspect of the present invention, a computer program product is presented comprising instructions which, when the program is executed by a computer, cause the computer to carry out a method comprising:

determining a pre-surgical prognostic risk score for a prostate cancer subject based on a gene expression profile for phosphodiesterase 4D variant 7 (PDE4D7) and a gene expression profile for DExH-box helicase 9 (DHX9), wherein the gene expression profile for PDE4D7 had been determined in a biological sample obtained from the subject and the gene expression profile for DHX9 had been determined in the same or another biological sample obtained from the subject.

It is preferred that the gene expression profile for PDE4D7 and the gene expression profile for DHX9 are combined with a regression function that had been derived from a population of prostate cancer subjects.

In further preferred embodiments, a post-surgical prognostic risk score for the subject is determined based on the pre-surgical prognostic risk score and the post-surgical clinical risk score CAPRA-S.

It is preferred that the pre-surgical prognostic risk score and the post-surgical clinical risk score CAPRA-S are combined with a regression function that had been derived from a population of prostate cancer subjects.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Overview of Pre-Surgical Risk Stratification

Figure 1:
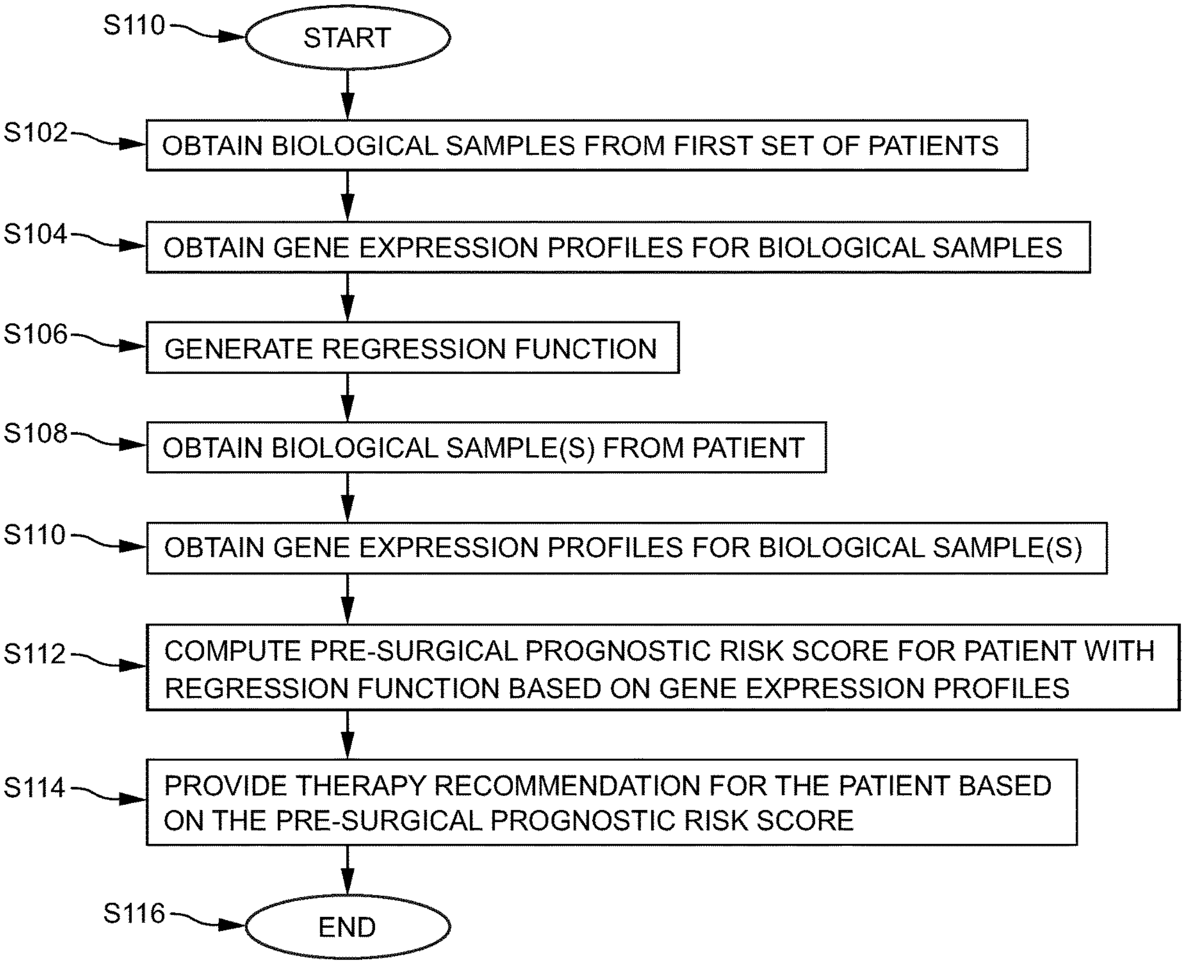
FIG. 1 shows schematically and exemplarily a flowchart of an embodiment of a method of pre-surgical risk stratification of a prostate cancer subject.

FIG. 1 shows schematically and exemplarily a flowchart of an embodiment of a method of pre-surgical risk stratification of a prostate cancer subject.

The method begins at step S100.

At step S102, one or more biological sample(s) is/are obtained from each of a first set of patients (subjects) diagnosed with prostate cancer. Preferably, monitoring prostate cancer has been performed for these prostate cancer patients over a period of time, such as at least one year, or at least two years, or about five years, after obtaining the biological sample.

At step S104, gene expression profiles for PDE4D7 and for DHX9 are obtained for a same or different biological sample(s) obtained from each of the first set of patients, e.g., by performing RT-qPCR (real-time quantitative PCR) on RNA extracted from each biological sample. The exemplary gene expression profiles include an expression level (e.g., value) for PDE4D7 and for DHX9 which can be normalized using value(s) for each of a set of reference genes, such as HPRT1, TUBA1B, PUM1, and/or TBP. In one realization, the gene expression profile value of PDE4D7 and of DHX9 is normalized to with respect to one or more reference genes selected from the group consisting of HPRT1, TUBA1B, PUM1, and TBP, e.g., at least one, or at least two, or at least three, or, preferably, all of these reference genes.

At step S106, a regression function for assigning a pre-surgical prognostic risk score is determined, based on the gene expression profiles for PDE4D7 and for DHX9 obtained for at least some of the biological samples obtained for the first set of patients and respective results obtained from the monitoring. In one possible realization, the normalized gene expression profile(s) for PDE4D7 and/or DHX9 are first transformed into a predefined range of values, such as the above-mentioned range of 1 to 5, using (a) suitable transform function(s). As mentioned above, such a transformation can be determined by considering the frequency distribution of the normalized gene expression profile values for e.g. PDE4D7 (or for DHX9) for biological samples of a population of prostate cancer subjects (here, the first set of patients) and by determining the transformation that transforms the frequency distribution into the desired range. In one particular realization, the normalized transformed gene expression profile value(s) is/are determined as specified in Eq. (1) above.

At step S108, one or more biological sample(s) is/are obtained from a patient (subject or individual). The patient can be a new patient or one of the first set.

At step S110, gene expression profiles are obtained for PDE4D7 and DHX9, e.g., by performing PCR on the biological sample. In one realization, the gene expression profile values of PDE4D7 and of DHX9 are normalized to with respect to one or more reference genes selected from the group consisting of HPRT1, TUBA1B, PUM1, and TBP, e.g., at least one, or at least two, or at least three, or, preferably, all of these reference genes. This is substantially the same as in step S104. Moreover, the normalized gene expression profile(s) for PDE4D7 and/or DHX9 can be pretransformed as described with respect to step S106.

Other reference genes which may be additionally or alternatively used in steps S104 and S110 include: *Homo*

*sapiens* actin, beta, mRNA (ACTB); *Homo sapiens* 60S acidic ribosomal phosphoprotein P0 mRNA (RPLP0); Polymerase (RNA) II (DNA Directed) Polypeptide A, 220 kDa (POLR2A); Beta-2-Microglobulin (B2M); and Aminolevulinate-Delta-Synthase (ALAS-1).

At step S112, a pre-surgical prognostic risk score is determined for the patient with the regression function based on the gene expression profiles for PDE4D7 and DHX9. This will be described in more detail later in the description. To make the pre-surgical prognostic score intuitive for the user, it may also be determined such that its values fall into a predefined value range, such as the range from 1 to 5. This can either be achieved already with the regression function itself or by means of a suitable subsequent transformation that transforms the output values of the regression function into the desired value range. Again, this is similar to other categories used in the clinical routine, e.g., in histo-pathology grading (Gleason) or multi-parametric MRI radiology scoring (PIRADS).

At S114, a therapy recommendation may be provided, e.g., to the patient or his or her guardian, to a doctor, or to another healthcare worker, based on the pre-surgical prognostic risk score. To this end, the pre-surgical prognostic risk score may be categorized into one of a predefined set of risk groups, based on the value of the pre-surgical prognostic risk score. Providing a therapy recommendation may include one or more of: a) proposing a therapy for the patient based on the assigned risk group, with at least two of the risk groups being associated with different therapies, b) computing a disease progression risk prediction of the patient before or after prostate surgery; and c) computing a therapy response prediction for the patient before or after prostate surgery. Example therapies include at least a partial prostatectomy, an active therapy selected from radiation treatment, chemotherapy, and a combination thereof, and observation alone, i.e., without performing prostatectomy or active therapy (i.e., active surveillance).

The method ends at S116.

Each of the risk groups may be associated with a respective proposed therapy, which differs in its aggressiveness. Each proposed therapy may be based on the results of the patients from the first set that were assigned to that risk group and is one which is predicted to provide the least aggressive therapy which does not exceed a threshold clinical risk for development of prostate cancer. In some cases, this enables a new patient to be assigned to a risk group associated with a less aggressive proposed therapy than would be the case for other risk profiling methods, such as that using the Gleason score, the NCCN risk categories, or the pre-surgical CAPRA score.

In one embodiment, the gene expression profiles at steps S104 and S110 are determined by detecting mRNA expression using one or more primers and/or probes and/or one or more sets thereof.

A detailed description of PDE4D7, DHX9 and the one or more reference genes including their Transcript ID (NCBI RefSeq) and the corresponding amino acid sequences for the primer pair and probe are shown in TABLE 1. This table also shows, for each gene, a sense primer, and antisense primer, and a probe sequence that specifically binds to the amplicon.

TABLE 1

| Exemplary primer and probe nucleic acid sequences | | | | | |
|---|---|---|---|---|---|
| Gene Name | Exemplary NCBI RefSeq | Exemplary Protein Accession | Sense Primer | Antisense primer | Probe Sequence |
| PDE4D7 | NM_001165899.1 (SEQ ID NO: 19) | NP_001159371.1 (SEQ ID NO: 20) | GAACATTCAACGAC CAACCA (SEQ ID NO: 21) CGCTGATTGCTATCA CTTCTGC (SEQ ID NO: 24) | TGCCATTGTCCACATC AAAA (SEQ ID NO: 22) GTCGTTGACTGTGGAC AAAATTTG (SEQ ID NO: 25) | CTGCCGCTGATTGCT ATCACTTCTGCA (SEQ ID NO: 23) TTCCCTTGGATCCCA TGACCAGCCCATAAG GGAA (SEQ ID NO: 26) |
| DHX9 | NM_001357.4 (SEQ ID NO: 74) | NP_001348.2 (SEQ ID NO: 75) | to be individually designed | to be individually designed | to be individually designed |
| HPRT1 | NM_000194.2 (SEQ ID NO: 34) | NP_000185.1 (SEQ ID NO: 35) | GAGGATTTGGAAAGG GTGTTTATT (SEQ ID NO: 36) | ACAGAGGGCTACAATG TGATG (SEQ ID NO: 37) | ACGTCTTGCTCGAGA TGTGATGAAGG (SEQ ID NO: 38) |
| TUBA1B | NM_006082.2 (SEQ ID NO: 39) | NP_006073.2 (SEQ ID NO: 40) | TGACTCCTTCAACAC CTTCTTC (SEQ ID NO: 41) | TGCCAGTGCGAACTTC AT (SEQ ID NO: 42) | CCGGGCTGTGTTTGT AGACTTGGA (SEQ ID NO: 43) |
| PUM1 | NM_001020658.1 (SEQ ID NO: 44); NM_014676.2 (SEQ ID NO: 45) | NP_001018494.1 (SEQ ID NO: 46); NP_055491.1 (SEQ ID NO: 47) | GCCAGCTTGTCTTCA ATGAAAT (SEQ ID NO: 48) | CAAAGCCAGCTTCTGT TCAAG (SEQ ID NO: 49) | ATCCACCATGAGTTG GTAGGCAGC (SEQ ID NO: 50) |
| TBP | NM_003194.4 (SEQ ID NO: 51) | NP_003185.1 (SEQ ID NO: 52) | GCCAAGAAGAAAGTG AACATCAT (SEQ ID NO: 53) | ATAGGGATTCCGGGAG TCAT (SEQ ID NO: 54) | TCAGAACAACAGCCT GCCACCTTA (SEQ ID NO: 55) |
| ACTB | NM_001101.3 (SEQ ID NO: 56) | NP_001092.1 (SEQ ID NO: 57) | CCAACCGCGAGAAGA TGA (SEQ ID NO: 58) | CCAGAGGCGTACAGGG ATAG (SEQ ID NO: 59) | CCATGTACGTTGCTA TCCAGGCT (SEQ ID NO: 60) |
| RPLP0 | NM_001002.3 (SEQ ID NO: 61) | NP_444505.1/ NP_000993.1 (SEQ ID NO: 62/63) | TAAACCCTGCGTGGC AAT (SEQ ID NO: 64) | ACATTTCGGATAATCA TCCAATAGTTG (SEQ ID NO: 65) | AAGTAGTTGGACTTC CAGGTCGCC (SEQ ID NO: 66) |
| ALAS-1 | NM_000688.5/ NM_199166.2 (SEQ ID NO: 67/68) | NP_000679.1/ NP_954635.1 (SEQ ID NO: 69/70) | AGCCACATCATCCCT GT (SEQ ID NO: 71) | CGTAGATGTTATGTCT GCTCAT (SEQ ID NO: 72) | TTTAGCAGCATCTGC AACCCGC (SEQ ID NO: 73) |

Instead of using RT-qPCR, the gene expression profiles for PDE4D7 and/or DHX9 at steps S104 and S110 may be determined in other embodiments by other means, for example, by performing RNA next-generation sequencing (NGS RNAseq) according to standard methods (Illumina, Inc.). In this case, the described transformations to a pre-defined value range may also be performed on the gene expression profile(s) provided by NGS RNAseq.

To explore the prognostic power of PDE4D7 and DHX9 in pre-surgical patient risk assessment, the correlation to disease recurrence was investigated.

A combination model based on the gene expression profiles of PDE4D7 and DHX9 was developed in a surgery cohort and the model was validated for different longitudinal clinical outcomes. The results show that the combination of the gene expression profiles for both PDE4D7 and DHX9 in an improved pre-surgical prognostic risk score may allow for better patient stratification in order to optimize primary treatment decisions.

EXAMPLES

Patient Cohort and Samples

A radical prostatectomy (RP) patient cohort, with the demographics shown in TABLE 2, was employed. For the RP patient cohort, a small biopsy punch (approximately 1 millimeter by 2 millimeters) of tissue was collected of a representative tumor area from the resected prostate from 575 patients who had been consecutively operated on between 2000 and 2004 at a single high-volume clinical center in Germany.

TABLE 2

| Demographics of the radical prostatectomy (RP) patient cohort | | |
|---|---|---|
| Surgery: 2000-2004 | Parameter | RP cohort (#575) |
| Demographic & Clinical | Age (at RP) | 41.3-79.2 (62.7) |
| Range | Preoperative PSA | 0.18-120.0 (7.1) |
| (median) | Percentage tumor in biopsy | 0.2-80.0 (10.3) |

TABLE 2-continued

Demographics of the radical prostatectomy (RP) patient cohort

| Surgery: 2000-2004 | Parameter | RP cohort (#575) |
|---|---|---|
| | Prostate Volume | 9-244 (42) |
| | PSA density | 0.01-24.0 (0.18) |
| CAPRA-S Risk Category | Low Risk (CAPRA-S 0-2) | 275 (47.8%) |
| No. of patients | Intermediate Risk (CAPRA-S 3-5) | 220 (38.3%) |
| (percentage) | High Risk (CAPRA-S >5) | 80 (13.9%) |
| Post-Surgery Pathology | Pathology Gleason 3 + 3 (GG1) | 190 (33%) |
| No. of patients | Pathology Gleason 3 + 4 (GG2) | 288 (50.1%) |
| (percentage) | Pathology Gleason 4 + 3 (GG3) | 73 (12.7%) |
| | Pathology Gleason >=4 + 4 (≥GG4) | 24 (4.2%) |
| | pT2 | 331 (57.6%) |
| | pT3 | 244 (42.4%) |
| | pT4 | 0 (0%) |
| | Positive Surgical Margins | 211 (36.7%) |
| | Extra-Capsular Extension (=T3a) | 151 (26.3%) |
| | Positive Seminal Vesicle Invasion | 95 (16.5%) |
| | Positive Lymph Node Invasion | 20 (3.5%) |
| Follow-up | Mean | 104.3 |
| Months | IQR median | 120 |
| Outcome | <5 y BCR | 184/512 (35.9%) |
| No. of events/ | <10 y BCR | 228/428 (53.3%) |
| total no. of patients | <5 y CR | 49/503 (9.7%) |
| (percentage) | <10 y CR | 64/356 (18.0%) |
| Salvage Treatment | <5 y SRT | 141/506 (27.9%) |
| No. of events/ | <10 y SRT | 178/405 (44.0%) |
| total no. of patients | <5 y SADT | 79/498 (15.9%) |
| (percentage) | <10 y SADT | 118/370 (31.9%) |
| Mortality | <5 y PCSS | 14/483 (2.9%) |
| No. of events/ | <10 y PCSS | 26/321 (8.1%) |
| total no. of patients | <5 y OS | 27/496 (5.4%) |
| (percentage) | <10 y OS | 54/349 (15.5%) |

For patient age, preoperative PSA, percentage of tumor in biopsy, prostate volume, and PSA density, the minimum and maximum values in the cohort are shown, while the median values are depicted in parentheses. For the CAPRA-S risk categories, the number of patients and percentage per risk group are shown. Post-surgical pathology is represented by the pathology Gleason scores and Gleason grade groups, the pathology stages, the surgical margin status after prostatectomy, the tumor invasion status of the seminal vesicles and pelvic lymph nodes (by number and percentage of patients). In this respect, it is noted that the extracapsular extension was not provided as a primary parameter but was derived from pathology stage pT3a. The follow-up demonstrates the mean and median follow-up periods in months after surgery for all patients. The outcome category illustrates the cumulative 5- and 10-year biochemical recurrence (BCR) and clinical recurrence to metastases (CR) post-surgical primary treatment. The treatment category lists the cumulative 5- and 10-year start to salvage radiation therapy (SRT) or salvage androgen deprivation therapy (SADT) after surgery. Mortality is shown as prostate cancer specific survival (PCSS) as well as overall survival (OS). For all outcomes, the number of men experiencing the outcome per total number of men with the respective 5- or 10-year follow are shown, wherein the percentage of events is given in parentheses.

Laboratory Methods

All used laboratory methods including oligonucleotide primers and probes for RT-qPCR (quantitative real-time PCR), RNA extraction, and quality control and procedures to include/discard samples from the statistical analysis were as described previously in Böttcher R. et al. or, in the case of DHX9, were based on RNA next-generation sequencing (NGS RNAseq) according to standard methods (Illumina, Inc.). The primers and probes used for the RT-qPCR to measure the genes of interest as well as the reference genes are also given in TABLE 1. In the case of NGS RNAseq, the resulting FastQ files were aligned to the human genome and processed according to standard methods. For each gene a gene expression value in the form of a TPM (transcript per kilobase million as obtained.

RESULTS

Logistic Regression Modeling of PDE4D7 and DHX9 Expression

The expression values for PDE4D7 and DHX9 were used in logistic regression modeling to create a combination model. As shown in TABLE 1 below, the dependent variable was taken as the 5-year biochemical recurrence (BCR) after prostate cancer surgery in a sub-cohort of 481 patients (169 events; 35.14%) of the RP patient cohort with complete 5-year outcome histories. The logit(p) regression function was transformed to p=1/(1+^(-logit(p)) in order to calculate the probability p for an individual patient to experience a biochemical relapse within 5 years after surgery. TABLES 2 to 6 show the results of the logistic regression modeling to combine the expression values of PDE4D7 and DHX9. TABLE 1 describes the inputs for the logistic regression modeling in terms of cohort size (#481) and the number of positive cases with 5-year biochemical recurrence (BCR) and negative cases without 5-year BCR. TABLE 2 provides information about the model fit and TABLE 3 outlines the coefficients (or weights) of the regression model with the respective statistics. TABLE 4 gives an overview on the odds ratios for PDE4D7 and DHX9 while TABLES 5 and 6 outline the data of a classification table and a ROC curve analysis for the "PDE4D7 & DHX9" regression model.

TABLE 1

| Input of the logistic regression modeling. | |
|---|---|
| Dependent Y | 5-year biochemical recurrence (BCR) |
| Method | Enter |
| Sample Size | 481 |
| Positive cases[a] | 169 (35.14%) |
| Negative cases[b] | 312 (64.86%) |

[a]5-year BCR = 1
[b]5-year BCR = 0

TABLE 2

| Overall model fit. | |
|---|---|
| Null model - 2 Log Likelihood | 623.645 |
| Full model - 2 Log Likelihood | 557.901 |
| Chi-squared | 65.744 |
| DF | 2 |
| Significance level | P < 0.0001 |
| Cox & Snell $R^2$ | 0.1278 |
| Nagelkerte $R^2$ | 0.1758 |

TABLE 3

Coefficients and standard errors.

| Variable | Coefficient | Std. error | Wald | P |
|---|---|---|---|---|
| PDE4D7 | −0.98799 | 0.17158 | 33.1574 | <0.0001 |
| DHX9 | −0.75891 | 0.17095 | 19.7082 | <0.0001 |
| Constant | 7.96032 | 1.38277 | 33.1409 | <0.0001 |

TABLE 4

Odd ratios and 95% confidence intervals.

| Variable | Odds ratio | 95% CI |
|---|---|---|
| PDE4D7 | 0.3723 | 0.2660 to 0.5212 |
| DHX9 | 0.4682 | 0.3349 to 0.6545 |

TABLE 5

Classification table (cut-off value p = 0.5).

| | Predicted group | | |
|---|---|---|---|
| Actual group | 0 | 1 | Percent correct |
| Y = 0 | 277 | 35 | 88.78% |
| Y = 1 | 116 | 53 | 31.36% |
| Percentage of cases correctly classified | | | 68.61% |

TABLE 6

| ROC curve analysis. | |
|---|---|
| Area under the ROC curve (AUC) | 0.713 |
| Standard error | 0.0241 |
| 95% confidence interval | 0.670 to 0.753 |

Validation of the Combination Model for Different Longitudinal Clinical Outcomes The combination model was tested to predict various clinically relevant endpoints after surgery, like biochemical recurrence (BCR), clinical recurrence (progression to local and/or distant metastases) (CR), and prostate cancer specific death. The prognostic power of the combination model was compared to the prognostic power of just PDE4D7 or DHX9 for the same various clinically relevant endpoints.

Figure 2:
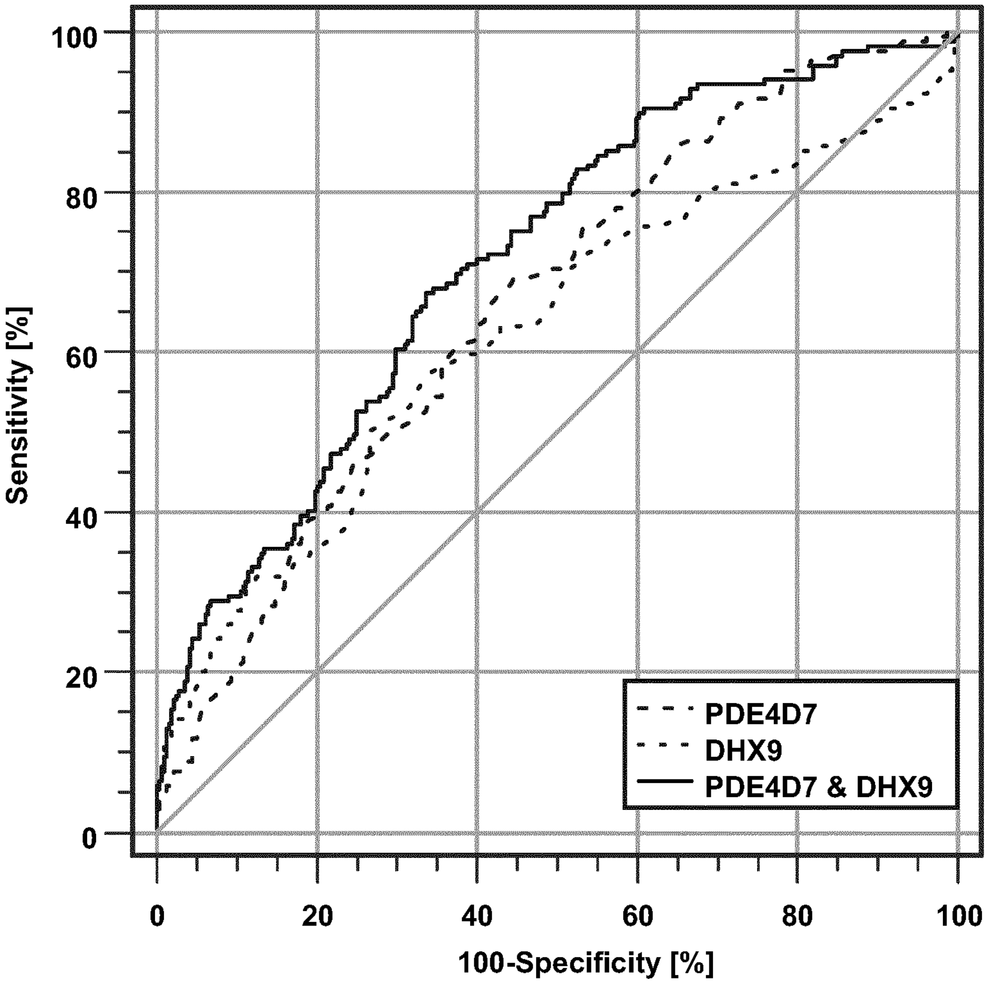
FIG. 2 shows results of a ROC curve analysis of 5-year biochemical recurrence (BCR) after prostate cancer surgery in the RP patient cohort.

FIG. 2 shows results of a ROC curve analysis of 5-year biochemical recurrence (BCR) after prostate cancer surgery for a sub-cohort (#481) of patients of the RP patient cohort with complete 5-year follow-up (see also TABLE 7). As detailed in TABLE 8, the 5-year AUCs (area under the curve) were calculated as 0.659 for PDE4D7 alone, as 0.624 for DHX9 alone, and as 0.713 for the combination model (indicated as "PDE4D7 & DHX9" in FIG. 2 and TABLE 8). The standard error was 0.0254 (PDE4D7), 0.0280 (DHX9) and 0.0242(PDE4D7 & DHX9), respectively, the 95% confidence interval was 0.615 to 0.702 (PDE4D7), 0.579 to 0.667 (DHX9) and 0.670 to 0.753 (PDE4D7 & DHX9), respectively. TABLE 9 shows a pairwise comparison of the ROC curves. As can be seen, the AUCs of PDE4D7 alone and of the combination model PDE4D7 & DHX9 were tested to be significantly different (p=0.0022). The same held true even in a slightly more significant manner for the AUCs of DHX9 alone and of the combination model PDE4D7 & DHX9 (p=0.0008).

TABLE 7

| Sub-cohort. | |
|---|---|
| Variable 1 | PDE4D7 |
| Variable 2 | DHX9 |
| Variable 3 | PDE4D7 & DHX9 |
| Classification variable | 5 year BCR |
| Sample Size | 481 |
| Positive cases[a] | 169 (35.14%) |
| Negative cases[b] | 312 (64.86%) |

[a]5-year BCR = 1
[b]5-year BCR = 0

TABLE 8

ROC curve analysis.

| Variable | AUC | Std. error[c] | 95% CI[d] |
|---|---|---|---|
| PDE4D7 | 0.659 | 0.0254 | 0.615 to 0.702 |
| DHX9 | 0.624 | 0.0280 | 0.579 to 0.667 |
| PDE4D7 & DHX9 | 0.713 | 0.0242 | 0.670 to 0.753 |

[c]DeLong E.R. et al., "Comparing the areas under two or more correlated receiver operating characteristic curves: a nonparameteric approach", Biometrics, Vol. 44, No. 3, pages 837 to 845, 1988.
[b]Binomial exact

TABLE 9

| Pairwise comparison of ROC curves. | |
|---|---|
| PDE4D7~DHX9 | |
| Difference between areas | 0.0352 |
| Standard error[c] | 0.0392 |
| 95% confidence interval | −0.0416 to 0.112 |
| z statistic | 0.899 |
| Significance level | p = 0.3687 |
| PDE4D7~PDE4D7 & DHX9 | |
| Difference between areas | 0.0538 |
| Standard error[c] | 0.0176 |
| 95% confidence interval | 0.0193 to 0.0883 |
| z statistic | 3.058 |
| Significance level | p = 0.0022 |
| DHX9~PDE4D7 & DHX9 | |
| Difference between areas | 0.0890 |
| Standard error[c] | 0.0265 |
| 95% confidence interval | 0.0372 to 0.141 |

TABLE 9-continued

| Pairwise comparison of ROC curves. | |
|---|---|
| z statistic | 3.365 |
| Significance level | p = 0.0008 |

[c]DeLong E.R. et al.

Figure 3:
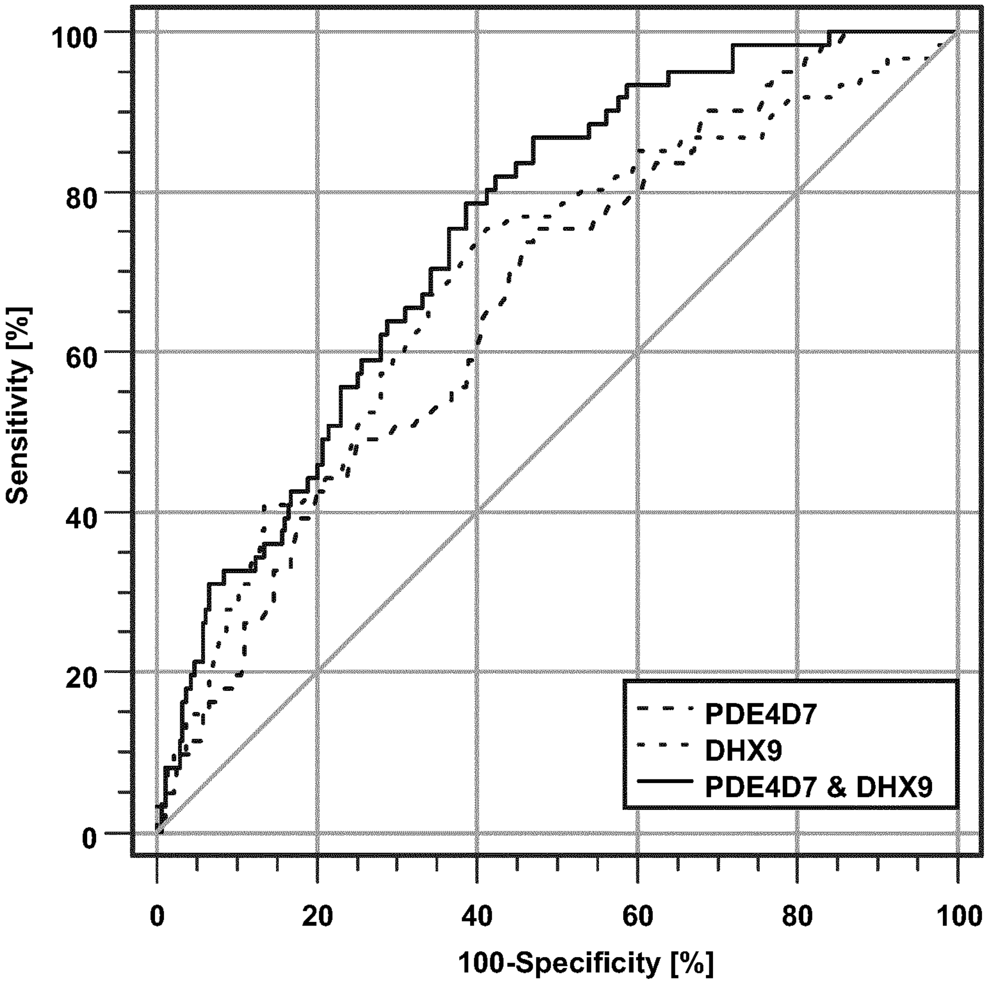
FIG. 3 shows results of a ROC curve analysis of 10-year clinical recurrence (CR) after prostate cancer surgery in the RP patient cohort.

FIG. 3 shows results of a ROC curve analysis of 10-year clinical recurrence (CR) after prostate cancer surgery for a sub-cohort (#335) of patients of the RP patient cohort with complete 10-year follow-up (see also TABLE 10). As detailed in TABLE 11, the 10-year AUCs (area under the curve) were calculated as 0.666 for PDE4D7 alone, as 0.691 for DHX9 alone, and as 0.748 for the combination model (indicated as "PDE4D7 & DHX9" in FIG. 3 and TABLE 11). The standard error was 0.0364 (PDE4D7), 0.0384 (DHX9) and 0.0314 (PDE4D7 & DHX9), respectively, the 95% confidence interval was 0.613 to 0.717 (PDE4D7), 0.639 to 0.740 (DHX9) and 0.698 to 0.794 (PDE4D7 & DHX9), respectively. TABLE 12 shows a pairwise comparison of the ROC curves. As can be seen, the AUCs of PDE4D7 alone and of the combination model PDE4D7 & DHX9 were tested to be significantly different (p=0.0039).

TABLE 10

| Sub-cohort. | |
|---|---|
| Variable 1 | PDE4D7 |
| Variable 2 | DHX9 |
| Variable 3 | PDE4D7 & DHX9 |
| Classification variable | 10 year clinical recurrence (CR) |
| Sample Size | 335 |
| Positive cases[a] | 61 (18.21%) |
| Negative cases[b] | 274 (81.79%) |

[a]10-year CR = 1
[b]10-year CR = 0

TABLE 11

ROC curve analysis.

| Variable | AUC | Std. error[c] | 95% CI[d] |
|---|---|---|---|
| PDE4D7 | 0.666 | 0.0364 | 0.613 to 0.717 |
| DHX9 | 0.691 | 0.0384 | 0.639 to 0.740 |
| PDE4D7 & DHX9 | 0.748 | 0.0314 | 0.698 to 0.794 |

[c]DeLong E.R. et al.
[d]Binomial exact

TABLE 12

| Pairwise comparison of ROC curves. | |
|---|---|
| **PDE4D7~DHX9** | |
| Difference between areas | 0.0249 |
| Standard error[c] | 0.0573 |
| 95% confidence interval | −0.0873 to 0.137 |
| z statistic | 0.435 |
| Significance level | p = 0.6635 |
| **PDE4D7~PDE4D7 & DHX9** | |
| Difference between areas | 0.0816 |
| Standard error[c] | 0.0283 |
| 95% confidence interval | 0.0262 to 0.137 |
| z statistic | 2.888 |
| Significance level | p = 0.0039 |

TABLE 12-continued

| Pairwise comparison of ROC curves. | |
|---|---|
| **DHX9~PDE4D7 & DHX9** | |
| Difference between areas | 0.0567 |
| Standard error[c] | 0.0361 |
| 95% confidence interval | −0.0141 to 0.128 |
| z statistic | 1.569 |
| Significance level | p = 0.1166 |

[c]DeLong E.R. et al.

Figure 4:
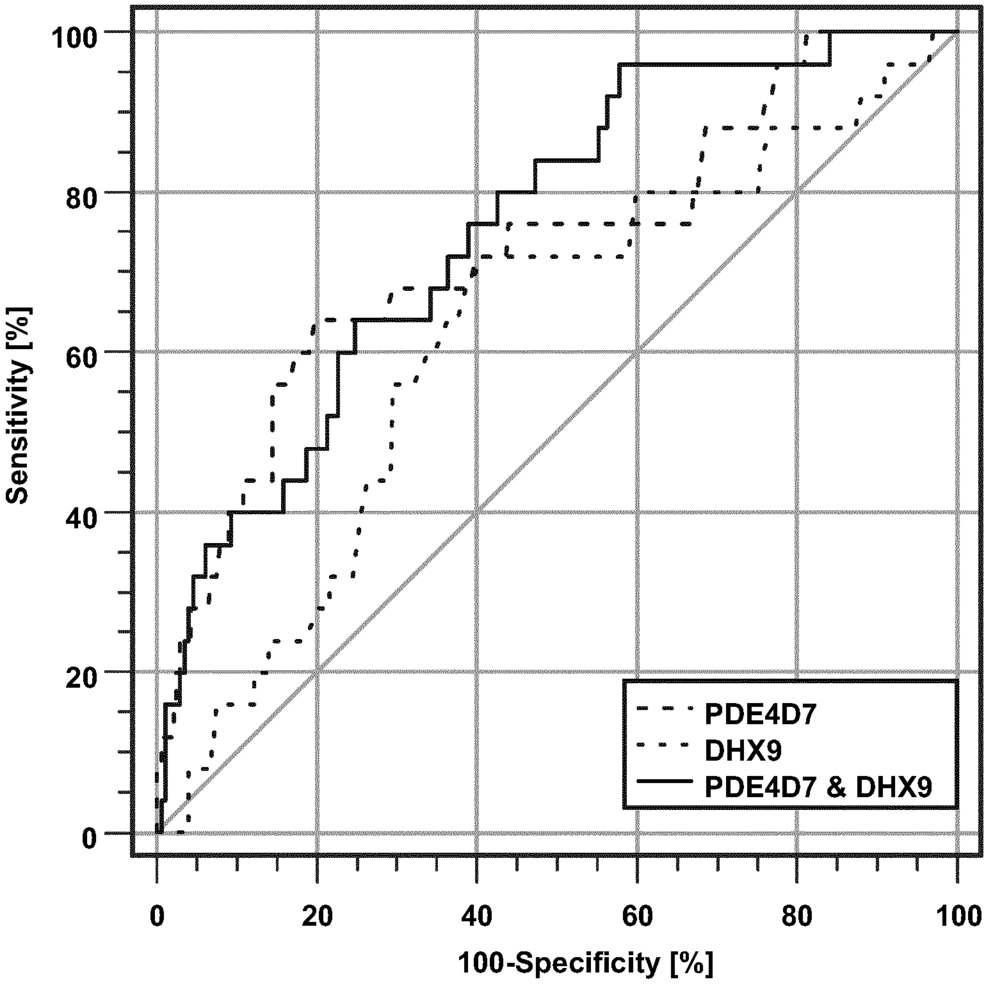
FIG. 4 shows results of a ROC curve analysis of 10-year prostate cancer specific death after prostate cancer surgery in the RP patient cohort.

FIG. 4 shows results of a ROC curve analysis of 10-year prostate cancer specific death after prostate cancer surgery for a sub-cohort (#302) of patients of the RP patient cohort with complete 10-year follow-up (see also TABLE 13). As detailed in TABLE 14, the 10-year AUCs (area under the curve) were calculated as 0.729 for PDE4D7 alone, as 0.622 for DHX9 alone, and as 0.754 for the combination model (indicated as "PDE4D7 & DHX9" in FIG. 4 and TABLE 14). The standard error was 0.0588 (PDE4D7), 0.0593 (DHX9) and 0.0481 (PDE4D7 & DHX9), respectively, the 95% confidence interval was 0.676 to 0.779 (PDE4D7), 0.564 to 0.676 (DHX9) and 0.702 to 0.802 (PDE4D7 & DHX9), respectively. TABLE 15 shows a pairwise comparison of the ROC curves. As can be seen, the AUCs of DHX9 alone and of the combination model PDE4D7 & DHX9 were tested to be significantly different (p=0.0403).

TABLE 13

| Sub-cohort. | |
|---|---|
| Variable 1 | PDE4D7 |
| Variable 2 | DHX9 |
| Variable 3 | PDE4D7 & DHX9 |
| Classification variable | 10-year prostate cancer specific death |
| Sample Size | 302 |
| Positive cases[a] | 25 (8.28%) |
| Negative cases[b] | 277 (91.72%) |

[a]10-year PCSS = 1
[b]10-year PCSS = 0

TABLE 14

ROC curve analysis.

| Variable | AUC | Std. error[c] | 95% CI[d] |
|---|---|---|---|
| PDE4D7 | 0.729 | 0.0588 | 0.676 to 0.779 |
| DHX9 | 0.622 | 0.0593 | 0.564 to 0.676 |
| PDE4D7 & DHX9 | 0.754 | 0.0481 | 0.702 to 0.802 |

[c]DeLong E.R. et al.
[d]Binomial exact

TABLE 15

| Pairwise comparison of ROC curves. | |
|---|---|
| **PDE4D7~DHX9** | |
| Difference between areas | 0.108 |
| Standard error[c] | 0.0909 |
| 95% confidence interval | −0.0702 to 0.286 |
| z statistic | 1.188 |
| Significance level | p = 0.2349 |
| **PDE4D7~PDE4D7 & DHX9** | |
| Difference between areas | 0.0249 |
| Standard error[c] | 0.0356 |
| 95% confidence interval | −0.0448 to 0.0946 |

TABLE 15-continued

| Pairwise comparison of ROC curves. | |
|---|---|
| z statistic | 0.700 |
| Significance level | p = 0.4836 |
| DHX9~PDE4D7 & DHX9 | |
| Difference between areas | 0.133 |
| Standard error[c] | 0.0648 |
| 95% confidence interval | 0.00585 to 0.260 |
| z statistic | 2.050 |
| Significance level | p = 0.0403 |

[c]DeLong E.R. et al.

The provided results demonstrate that the use of the combination logistic regression model of PDE4D7 with DHX9 gene expression values to predict 5-year post-surgical biochemical recurrence improves the area under the curve (AUC) in ROC analysis between 2.5% (for prostate cancer specific death as endpoint) and 8% (for clinical recurrence as endpoint) compared to using PDE4D7 alone as a prognostic marker.

Figure 5:
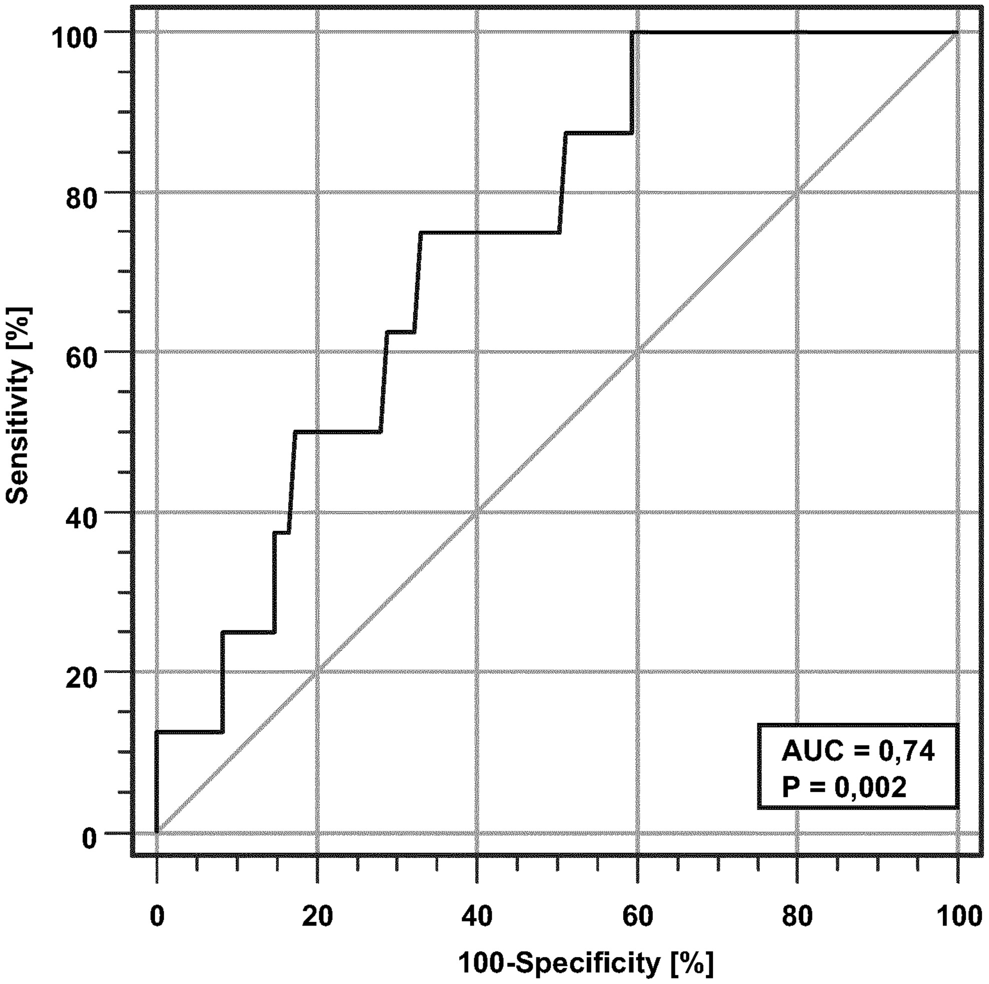
FIG. 5 shows results of independent testing of a combination model to predict metastases after prostate cancer surgery.

INdependent Testing of the Combination Model to Predict Metastases after Prostate Cancer Surgery in an Independent Data Set FIG. 5 shows an independent testing of the combination model (indicated as "PDE4D7 & DHX9" in TABLE 16) to predict metastases after prostate cancer surgery in an independent data set (data from Taylor B.S. et al., "Integrative genomic profiling of human prostate cancer", Cancer Cell, Vol. 18, No. 1, pages 11 to 22, 2010). As detailed in TABLE 16, the metastasis class AUC (area unter the curve) was calculated as 0.736 for PDE4D7 & DHX9. The standard error was 0.0777, the 95% confidence interval was 0.651 to 0.809.

TABLE 16

| Independent data set. | |
|---|---|
| Variable | PDE4D7 & DHX9 |
| Classification variable | Metastasis class |
| Sample Size | 129 |
| Positive cases[a] | 8 (6.20%) |
| Negative cases[b] | 121 (93.8%) |
| Disease prevalence (%) | unknown |

[a]Metastasis class = 1
[b]Metastasis class = 0

TABLE 17

| ROC curve analysis. | |
|---|---|
| AUC | 0.736 |
| Standard error[c] | 0.0777 |
| 95% confidence interval[d] | 0.651 to 0.809 |
| z statistic | 3.029 |
| Significance level | p = 0.024 |

[c]DeLong E.R. et al.
[d]Binomial exact

TABLE 18

| Youden index. | |
|---|---|
| Youden index J | 0.4194 |
| Associated criterion | >−1.16 |
| Sensitivity | 75.00 |
| Specificity | 66.94 |

Logistic Regression Modeling of the PDE4D7 & DHX9 Combination Model with the Post-Surgical Clinical Risk Score Capra-s to Predict Post-Surgical Metastases The PDE4D7 & DHX9 combination model and the post-surgical clinical risk score CAPRA-S were used in an additional logistic regression modeling to create a further combination model (indicated as "PDE4D7 & DHX9 & CAPRA-S" in the following). As shown in TABLE 19 below, the dependent variable was taken as the metastasis class after prostate cancer surgery in the independent data from Tayler B.S. et al. (see above). The logit(p) regression function was transformed to p=1/(1+e^(-logit(p)) in order to calculate the probability p for an individual patient to experience metastases after surgery. TABLES 20 to 26 show the results of the logistic regression modeling to combine PDE4D7 & DHX9 and the CAPRA-S score. TABLE 19 describes the inputs for the logistic regression modeling in terms of sample size (#129) and the number of positive cases with metastases and negative cases without metastases. TABLE 20 provides information about the model fit and TABLE 21 outlines the coefficients (or weights) of the regression model with the respective statistics. TABLE 22 gives an overview on the odds ratios for PDE4D7 & DHX9 and the CAPRA-S score while TABLES 23 and 24 show the results of the calibration testing of the regression model (according to the Hosmer & Lemeshow test). Finally, TABLES 25 and 26 outline the data of a classification table and a ROC curve analysis for the "PDE4D7 & DHX9 & CAPRA-S" regression model.

TABLE 19

| Input of the logistic regression modeling. | |
|---|---|
| Dependent Y | Metastasis class |
| Method | Enter |
| Sample Size | 129 |
| Positive cases[a] | 8 (6.20%) |
| Negative cases[b] | 121 (93.8%) |

[a]Metastasis class = 1
[b]Metastasis class = 0

TABLE 20

| Overall model fit. | |
|---|---|
| Null model - 2 Log Likelihood | 59.979 |
| Full model - 2 Log Likelihood | 49.989 |
| Chi-squared | 9.990 |
| DF | 2 |
| Significance level | p = 0.0068 |
| Cox & Snell $R^2$ | 0.0745 |
| Nagelkerte $R^2$ | 0.2004 |

TABLE 21

Coefficients and standard errors.

| Variable | Coefficient | Std. error | Wald | P |
|---|---|---|---|---|
| PDE4D7 & DHX9 | 0.77252 | 0.42392 | 3.3208 | 0.0684 |
| CAPRA-S score | 0.25375 | 0.12488 | 4.1290 | 0.0422 |
| Constant | −2.80880 | 0.87165 | 10.3837 | 0.0013 |

TABLE 22

| Odd ratios and 95% confidence intervals. | | |
|---|---|---|
| Variable | Odds ratio | 95% CI |
| PDE4D7 & DHX9 | 2.1652 | 0.9433 to 4.9699 |
| CAPRA-S score | 1.2888 | 1.0090 to 1.6463 |

TABLE 23

| Hosmer & Lemeshow test. | |
|---|---|
| Chi-squared | 2.9654 |
| DF | 8 |
| Significance level | p = 0.9365 |

TABLE 24

Contingency table for Hosmer & Lemeshow test.

| | Y = 0 | | Y = 1 | | |
|---|---|---|---|---|---|
| Group | Observed | Expected | Observed | Expected | Total |
| 1 | 13 | 12.928 | 0 | 0.072 | 13 |
| 2 | 13 | 12.863 | 0 | 0.137 | 13 |
| 3 | 13 | 12.776 | 0 | 0.224 | 13 |
| 4 | 13 | 12.696 | 0 | 0.304 | 13 |
| 5 | 12 | 12.615 | 1 | 0.385 | 13 |
| 6 | 13 | 12.499 | 0 | 0.501 | 13 |
| 7 | 12 | 12.292 | 1 | 0.708 | 13 |
| 8 | 12 | 12.040 | 1 | 0.960 | 13 |
| 9 | 12 | 11.433 | 1 | 1.567 | 13 |
| 10 | 8 | 8.857 | 4 | 3.143 | 12 |

TABLE 25

Classification table (cut-off value p = 0.5).

| | Predicted group | | |
|---|---|---|---|
| Actual group | 0 | 1 | Percent correct |
| Y = 0 | 120 | 1 | 99.17% |
| Y = 1 | 8 | 0 | 0.00% |
| Percentage of cases correctly classified | | | 93.02% |

TABLE 26

| ROC curve analysis. | |
|---|---|
| AUC | 0.713 |
| Standard error[c] | 0.0241 |
| 95% confidence interval[d] | 0.670 to 0.753 |

Figure 6:
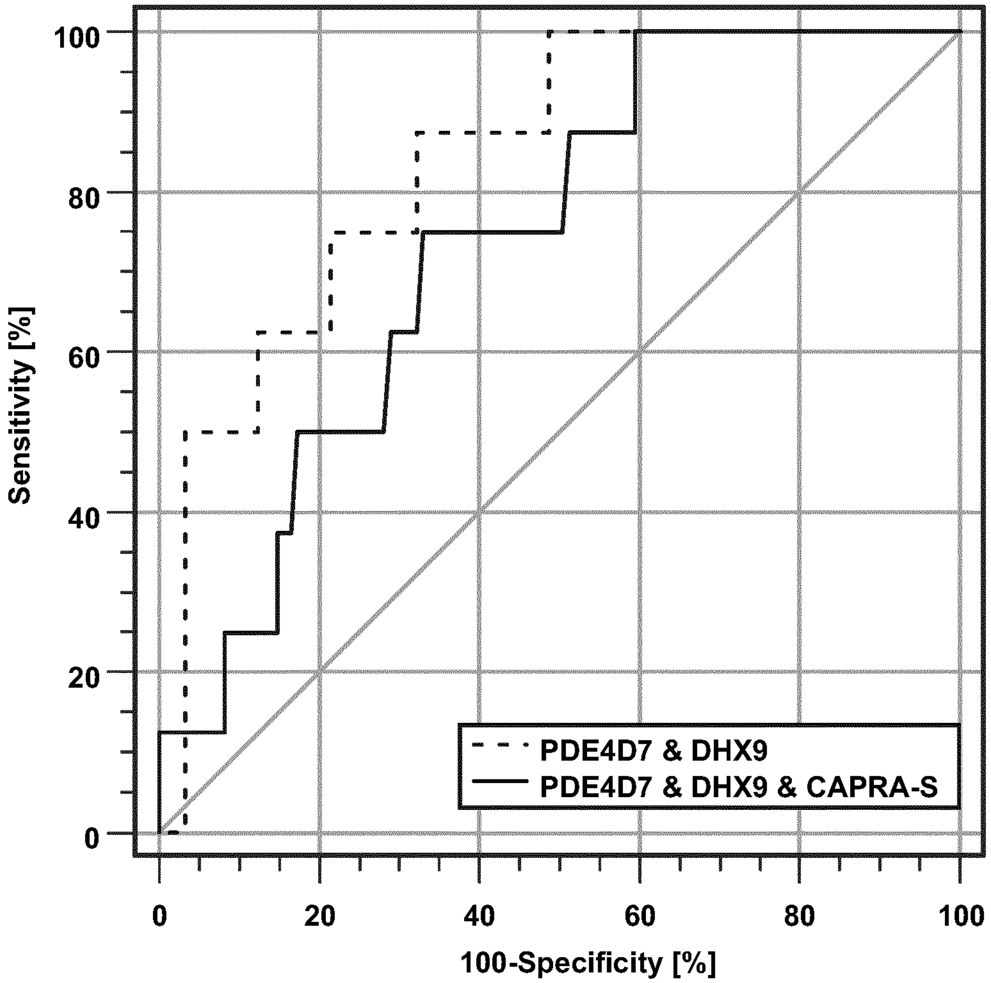
FIG. 6 shows results of PDE4D7 & DHX9 and PDE4D7 & DHX9 & CAPRA-S combination models to predict metastases after prostate cancer surgery.

FIG. 6 shows a ROC analysis of the PDE4D7 & DHX9 and PDE4D7 & DHX9 & CAPRA-S combination models to predict metastases after prostate cancer surgery (data from Taylor B. S. et al., "Integrative genomic profiling of human prostate cancer", Cancer Cell, Vol. 18, No. 1, pages 11 to 22, 2010). As detailed in TABLE 28, the metastasis class AUCs (area under the curve) were calculated as 0.736 for PDE4D7 & DHX9 alone and as 0.840 for PDE4D7 & DHX9 & CAPRA-S. The standard error was 0.0777 (PDE4D7 & DHX9) and 0.0636 (PDE4D7 & DHX9 & CAPRA-S), respectively, the 95% confidence interval was 0.651 to 0.809 (PDE4D7 & DHX9) and 0.765 to 0.899 (PDE4D7 & DHX9 & CAPRA-S), respectively. TABLE 29 shows a pairwise comparison of the ROC curves. As can be seen, the AUCs of PDE4D7 & DHX9 alone and of the combination model PDE4D7 & DHX9 & CAPRA-S were tested to be significantly different (p=0.0323) by a difference in AUC of 0,104 (or 10,4%).

TABLE 27

| Independent data set. | |
|---|---|
| Variable 1 | PDE4D7 & DHX9 |
| Variable 2 | PDE4D7 & DHX9 & CAPRA-S |
| Classification variable | Metastasis class |
| Sample Size | 129 |
| Positive cases[a] | 8 (6.20%) |
| Negative cases[b] | 121 (93.8%) |
| Disease prevalence (%) | unknown |

[a]Metastasis class = 1
[b]Metastasis class = 0

TABLE 28

ROC curve analysis.

| Variable | AUC | Std. error[c] | 95% CI[d] |
|---|---|---|---|
| PDE4D7 & DHX9 | 0.736 | 0.0777 | 0.651 to 0.809 |
| PDE4D7 & DHX9 & CAPRA-S | 0.840 | 0.0636 | 0.765 to 0.899 |

[c]DeLong E.R. et al.
[d]Binomial exact

TABLE 29

| Pairwise comparison of ROC curves. PDE4D7 & DHX9~PDE4D7 & DHX9 & CAPRA-S | |
|---|---|
| Difference between areas | 0.104 |
| Standard error[c] | 0.0487 |
| 95% confidence interval | 0.00881 to 0.200 |
| z statistic | 2.141 |
| Significance level | p = 0.0323 |

[c]DeLong E.R. et al.

Discussion

Treatment decisions in primary, localized prostate cancer are largely subject to a combination of the risk of future disease progression and life expectancy. The provided data illustrate that the use of a combination of PDE4D7 and DHX9 in a pre-surgical risk score adds value compared to using PDE4D7 as a prognostic marker alone. Thus, DHX9 may be adding prognostic value to PDE4D7 in clinical prediction models for disease specific outcomes like post-surgical progression to biochemical relapse or clinical recurrence to metastases as well as to the prediction of cancer specific survival to support treatment decision making.

Other variations to the disclosed realizations can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

One or more steps of the method illustrated in FIG. 1 may be implemented in a computer program product that may be executed on a computer. The computer program product may comprise a non-transitory computer-readable recording medium on which a control program is recorded (stored), such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other non-transitory medium from which a computer can read and use.

Alternatively, the one or more steps of the method may be implemented in transitory media, such as a transmittable carrier wave in which the control program is embodied as a data signal using transmission media, such as acoustic or light waves, such as those generated during radio wave and infrared data communications, and the like.

The exemplary method may be implemented on one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like. In general, any device, capable of implementing a finite state machine that is in turn capable of implementing the flowchart shown in FIG. 1, can be used to implement one or more steps of the method of risk stratification for therapy selection in a patient with prostate cancer is illustrated. As will be appreciated, while the steps of the method may all be computer implemented, in some embodiments one or more of the steps may be at least partially performed manually.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

While the invention has described so far based on the gene expression profile for PDE4D7, which can include an expression level (e.g., value) for PDE4D7 which can be normalized using value(s) for each of a set of reference genes, the gene expression profile may further include expression information from other PDE4D variants. For example, the other PDE4D variant(s) may include one or more of PDE4D1, PDE4D2, PDE4D3, PDE4D4, PDE4D5, PDE4D6, PDE4D8 and PDE4D9. The diagnostic kit may then additionally comprise at least one primer and/or probe for determining the gene expression profile for each of the other PDE4D variant(s) in the biological sample obtained from the prostate cancer subject. Preferably, however, only the gene expression profile for PDE4D7, in particular, an expression level (e.g., value) for PDE4D7 which can be normalized using value(s) for each of a set of reference genes, is employed.

The term "phosphodiesterase 4D1" or "PDE4D1" relates to the splice variant 1 of the human phosphodiesterase PDE4D, i.e., the human phosphodiesterase PDE4D1 gene, for example, to the sequence as defined in NCBI Reference Sequence: NM_001197222.1, specifically, to the nucleotide sequence as set forth in SEQ ID NO:1, which corresponds to the sequence of the above indicated NCBI Reference Sequence of the PDE4D1 transcript, and also relates to the corresponding amino acid sequence for example as set forth in SEQ ID NO:2, which corresponds to the protein sequence defined in NCBI Protein Accession Reference Sequence NP_001184151.1 encoding the PDE4D1 polypeptide. The term "phosphodiesterase 4D1" or "PDE4D1" also relates to the amplicon that can be generated by the primer pair PDE1D1D2_forward (SEQ ID NO:3) and the PDE1D1D2_reverse (SEQ ID NO:4) and can be detected by probe SEQ ID NO:5.

The term "phosphodiesterase 4D2" or "PDE4D2" refers to the splice variant 2 of the human phosphodiesterase PDE4D, i.e., the human phosphodiesterase PDE4D2 gene, for example, to the sequence as defined in NCBI Reference Sequence: NM_001197221.1, specifically, to the nucleotide sequence as set forth in SEQ ID NO:6, which corresponds to the sequence of the above indicated NCBI Reference Sequence of the PDE4D2 transcript, and also relates to the corresponding amino acid sequence for example as set forth in SEQ ID NO:7, which corresponds to the protein sequence defined in NCBI Protein Accession Reference Sequence NP_001184150.1 encoding the PDE4D2 polypeptide.

The term "phosphodiesterase 4D3" or "PDE4D3" refers to the splice variant 3 of the human phosphodiesterase PDE4D, i.e., the human phosphodiesterase PDE4D3 gene, for example, to the sequence as defined in NCBI Reference Sequence: NM_006203.4, specifically, to the nucleotide sequence as set forth in SEQ ID NO:8, which corresponds to the sequence of the above indicated NCBI Reference Sequence of the PDE4D3 transcript, and also relates to the corresponding amino acid sequence for example as set forth in SEQ ID NO:9, which corresponds to the protein sequence defined in NCBI Protein Accession Reference Sequence NP_006194.2 encoding the PDE4D3 polypeptide.

The term "phosphodiesterase 4D4" or "PDE4D4" refers to the splice variant 4 of the human phosphodiesterase PDE4D, i.e., the human phosphodiesterase PDE4D4 gene, for example, to the sequence as defined in NCBI Reference Sequence: NM_001104631.1, specifically, to the nucleotide sequence as set forth in SEQ ID NO:10, which corresponds to the sequence of the above indicated NCBI Reference Sequence of the PDE4D4 transcript, and also relates to the corresponding amino acid sequence for example as set forth in SEQ ID NO:11, which corresponds to the protein sequence defined in NCBI Protein Accession Reference Sequence NP_001098101.1 encoding the PDE4D4 polypeptide.

The term "phosphodiesterase 4D5" or "PDE4D5" refers to the splice variant 5 of the human phosphodiesterase PDE4D, i.e., the human phosphodiesterase PDE4D5 gene, for example, to the sequence as defined in NCBI Reference Sequence: NM_001197218.1, specifically, to the nucleotide sequence as set forth in SEQ ID NO:12, which corresponds to the sequence of the above indicated NCBI Reference Sequence of the PDE4D5 transcript, and also relates to the corresponding amino acid sequence for example as set forth in SEQ ID NO:13, which corresponds to the protein sequence defined in NCBI Protein Accession Reference Sequence NP_001184147.1 encoding the PDE4D5 polypeptide. The term "phosphodiesterase 4D5" or "PDE4D5" also relates to the amplicon that can be generated by the primer pair PDE4D5_forward (SEQ ID NO:14) and the PDE4D5_reverse (SEQ ID NO:15) and can be detected by probe SEQ ID NO:16.

The term "phosphodiesterase 4D6" or "PDE4D6" refers to the splice variant 6 of the human phosphodiesterase PDE4D, i.e., the human phosphodiesterase PDE4D6 gene, for example, to the sequence as defined in NCBI Reference Sequence: NM_001197223.1, specifically, to the nucleotide sequence as set forth in SEQ ID NO:17, which corresponds to the sequence of the above indicated NCBI Reference Sequence of the PDE4D6 transcript, and also relates to the corresponding amino acid sequence for example as set forth in SEQ ID NO:18, which corresponds to the protein sequence defined in NCBI Protein Accession Reference Sequence NP_001184152.1 encoding the PDE4D6 polypeptide.

The term "phosphodiesterase 4D8" or "PDE4D8" relates to the splice variant 8 of the human phosphodiesterase PDE4D, i.e., the human phosphodiesterase PDE4D8 gene, for example, to the sequence as defined in NCBI Reference Sequence: NM_001197219.1, specifically, to the nucleotide sequence as set forth in SEQ ID NO:27, which corresponds to the sequence of the above indicated NCBI Reference Sequence of the PDE4D8 transcript, and also relates to the corresponding amino acid sequence for example as set forth in SEQ ID NO:28, which corresponds to the protein sequence defined in NCBI Protein Accession Reference Sequence NP_001184148.1 encoding the PDE4D8 polypeptide.

The term "phosphodiesterase 4D9" or "PDE4D9" relates to the splice variant 9 of the human phosphodiesterase PDE4D, i.e., the human phosphodiesterase PDE4D9 gene, for example, to the sequence as defined in NCBI Reference Sequence: NM_001197220.1, specifically, to the nucleotide sequence as set forth in SEQ ID NO:29, which corresponds to the sequence of the above indicated NCBI Reference Sequence of the PDE4D9 transcript, and also relates to the corresponding amino acid sequence for example as set forth in SEQ ID NO:30 which corresponds to the protein sequence defined in NCBI Protein Accession Reference Sequence NP_001184149.1 encoding the PDE4D9 polypeptide. The term "phosphodiesterase 4D9" or "PDE4D9" also relates to the amplicon that can be generated by the primer pair PDE4D9_forward (SEQ ID NO:31) and the PDE4D9_reverse (SEQ ID NO:32) and can be detected by probe SEQ ID NO:33.

The terms "PDE4D1," "PDE4D2," "PDE4D3," "PDE4D4," "PDE4D5," "PDE4D6," "PDE4D8," and "PDE4D9" also comprises nucleotide sequences showing a high degree of homology to PDE4D1, PDE4D2, PDE4D3, PDE4D4, PDE4D5, PDE4D6, PDE4D8 and PDE4D9 respectively, e.g., nucleic acid sequences being at least 75%, 80%, 85%, 90%, 91%, 92%, 93%, 94%, 95%, 96%, 97%, 98% or 99% identical to the sequence as set forth in SEQ ID NOs: 1, 6, 8, 10, 12, 17, 27 or 29 respectively or amino acid sequences being at least 75%, 80%, 85%, 90%, 91%, 92%, 93%, 94%, 95%, 96%, 97%, 98% or 99% identical to the sequence as set forth in SEQ ID NO:2, 7, 9, 11, 13, 18, 28 or 30 respectively or nucleic acid sequences encoding amino acid sequences being at least 75%, 80%, 85%, 90%, 91%, 92%, 93%, 94%, 95%, 96%, 97%, 98% or 99% identical to the sequence as set forth in SEQ ID NO:2, 7, 9, 11, 13, 18, 28 or 30 or amino acid sequences being encoded by nucleic acid sequences being at least 75%, 80%, 85%, 90%, 91%, 92%, 93%, 94%, 95%, 96%, 97%, 98% or 99% identical to the sequence as set forth in SEQ ID NO:1, 6, 8, 10, 12, 17, 27 or 29.

Any reference signs in the claims should not be construed as limiting the scope.

The invention relates to a method of pre-surgical risk stratification of a prostate cancer subject, comprising determining a gene expression profile for phosphodiesterase 4D variant 7 (PDE4D7) in a biological sample obtained from the subject, determining a gene expression profile for DExH-box helicase 9 (DHX9) in the same or another biological sample obtained from the subject, and determining a pre-surgical prognostic risk score for the subject based on the gene expression profile for PDE4D7 and the gene expression profile for DHX9. This may allow for an improved stratification of the subject in a pre-surgical setting that may result in better primary treatment decisions. For instance, the pre-surgical prognostic risk score may allow to make better recommendations on whether to select active surveillance vs. active intervention, e.g., radical prostatectomy, for certain sub-populations of prostate cancer patients.

The invention claimed is:

1. A method of pre-surgical risk stratification of a prostate cancer subject, prior to the prostate cancer subject undergoing any prostate surgery, comprising:

determining a gene expression profile for phosphodiesterase 4D variant 7 (PDE4D7) in a biological sample obtained from the prostate cancer subject;

determining a gene expression profile for DExH-box helicase 9 (DHX9) in the same or another biological sample obtained from the prostate cancer subject; and determining a pre-surgical prognostic risk score for the prostate cancer subject based on the gene expression profile for PDE4D7 and the gene expression profile for DHX9, wherein the determined pre-surgical prognostic risk score for the subject stratifies the prostate cancer subject into a high risk group comprising a high risk of disease progression for the prostate cancer subject; and administering a primary treatment for the prostate cancer subject based on the pre-surgical prognostic risk score stratifying the prostate cancer subject into a high risk group comprising a high risk of disease progression for the prostate cancer subject, wherein the primary treatment is selected from the group consisting of: (i) at least a partial prostatectomy; (ii) an active therapy selected from radiation treatment, hormone therapy, chemotherapy; and (iii) a combination thereof.

2. The method as defined in claim 1, wherein the gene expression profile for PDE4D7 and the gene expression profile for DHX9 are combined with a regression function that had been derived from a population of prostate cancer subjects.

3. The method as defined in claim 1, further comprising:

proposing a primary treatment for the prostate cancer subject based on the pre-surgical prognostic risk score indicating a high risk of disease progression for the prostate cancer subject.

4. The method as defined in claim 1, further comprising:

normalizing the gene expression profile for PDE4D7 and/or the gene expression profile for DHX9 with respect to one or more reference genes selected from the group consisting of: *Homo sapiens* hypoxanthine phosphoribosyltransferase 1 (HPRT1), Tubulin-Alpha-1b (TUBA1B), *Homo sapiens pumilio* RNA-Binding Family Member (PUM1), and *Homo sapiens* TATA box binding protein (TBP), wherein the pre-surgical prognostic risk score is determined based on the normalized gene expression profile(s).

5. The method as defined in claim 4, wherein the one or more reference genes comprise at least two, or at least three, or all of HPRT1, TUBA1B, PUM1, and TBP.

6. The method as defined in claim 5, wherein the determining of the gene expression profile for PDE4D7 and/or the gene expression profile for DHX9 comprises performing RT-qPCR on RNA extracted from the biological sample(s), wherein a Cq value is determined for PDE4D7 and/or DHX9 and for each of the one or more reference genes, and wherein the determining of the pre-surgical risk score includes normalizing the Cq value for PDE4D7 and/or DHX9 using the Cq value for each of the one or more reference genes and computing the pre-surgical risk score based on the normalized Cq value(s).

7. A method for using a gene expression profile for phosphodiesterase 4D variant 7 (PDE4D7) and a gene expression profile for DExH-box helicase 9 (DHX9) in pre-surgical risk stratification of a prostate cancer subject prior to the prostate cancer subject undergoing any prostate surgery, the method comprising:

determining the gene expression profile for PDE4D7 in a biological sample obtained from the prostate cancer subject;

determining the gene expression profile for DHX9 in the same or another biological sample obtained from the prostate cancer subject;

determining a pre-surgical prognostic risk score for the prostate cancer subject based on the gene expression profile for PDE4D7 and the gene expression profile for DHX9, wherein the determined pre-surgical prognostic risk score for the subject stratifies the prostate cancer subject into a high risk group comprising a high risk of disease progression for the prostate cancer subject; and administering a primary treatment for the prostate cancer subject based on the pre-surgical prognostic risk score stratifying the prostate cancer subject into a high risk group comprising a high risk of disease progression for the prostate cancer subject, wherein the primary treatment is selected from the group consisting of: (i) at least a partial prostatectomy; (ii) an active therapy selected from radiation treatment, hormone therapy, chemotherapy; and (iii) a combination thereof.

8. The method of claim 7, wherein determining a pre-surgical prognostic risk score for the prostate cancer subject based on the gene expression profile for PDE4D7 and the gene expression profile for DHX9 comprises combining the gene expression profiles using a regression function derived from a population of prostate cancer subjects.

* * * * *